US010434213B2

(12) United States Patent
Van Dyke et al.

(10) Patent No.: US 10,434,213 B2
(45) Date of Patent: Oct. 8, 2019

(54) CONTROLLED DELIVERY SYSTEM

(75) Inventors: Mark E. Van Dyke, Winston-Salem, NC (US); Justin M. Saul, Winston-Salem, NC (US); Thomas L. Smith, Winston-Salem, NC (US); Roche de Guzman, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 28 days.

(21) Appl. No.: 13/042,126

(22) Filed: Mar. 7, 2011

(65) Prior Publication Data

US 2011/0217356 A1 Sep. 8, 2011

Related U.S. Application Data

(60) Provisional application No. 61/311,003, filed on Mar. 5, 2010.

(51) Int. Cl.
| | |
|---|---|
| *A61L 27/18* | (2006.01) |
| *A61L 15/26* | (2006.01) |
| *C08L 89/04* | (2006.01) |
| *A61L 15/44* | (2006.01) |
| *A61L 15/60* | (2006.01) |
| *A61L 27/52* | (2006.01) |
| *A61L 27/54* | (2006.01) |
| *C07K 14/47* | (2006.01) |

(52) U.S. Cl.
CPC .............. *A61L 27/18* (2013.01); *A61L 15/26* (2013.01); *A61L 15/44* (2013.01); *A61L 15/60* (2013.01); *A61L 27/52* (2013.01); *A61L 27/54* (2013.01); *C07K 14/4741* (2013.01); *A61L 2300/252* (2013.01)

(58) Field of Classification Search
None
See application file for complete search history.

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 1,214,299 A | 1/1917 | Grosvenor et al. | |
| 2,434,688 A | 1/1948 | Evans | |
| 2,445,028 A | 7/1948 | Jones et al. | |
| 2,517,572 A | 8/1950 | Jones et al. | |
| 2,814,851 A | 12/1957 | Hervey | |
| 3,033,755 A | 5/1962 | Jacobi | |
| 3,642,498 A | 2/1972 | Anker | |
| 3,655,416 A | 4/1972 | Vinson et al. | |
| 4,178,361 A | 12/1979 | Cohen et al. | |
| 4,357,274 A | 11/1982 | Werner et al. | |
| 4,423,032 A | 12/1983 | Abe et al. | |
| 4,495,173 A | 1/1985 | Matsunaga et al. | |
| 4,570,629 A | 2/1986 | Widra | |
| 4,751,074 A | 6/1988 | Matsunaga et al. | |
| 4,895,722 A | 1/1990 | Abe et al. | |
| 4,959,213 A | 9/1990 | Brod et al. | |
| 5,047,249 A | 9/1991 | Rothman et al. | |
| 5,300,285 A | 4/1994 | Halloran et al. | |
| 5,320,796 A | 6/1994 | Harashima et al. | |
| 5,358,935 A | 10/1994 | Smith et al. | |
| 5,634,945 A | 6/1997 | Pernia et al. | |
| 5,679,819 A | 10/1997 | Jones et al. | |
| 5,763,583 A | 6/1998 | Arai et al. | |
| 5,932,552 A | 8/1999 | Blanchard et al. | |
| 5,948,432 A | 9/1999 | Timmons et al. | |
| 5,972,335 A * | 10/1999 | Ferguson ............. | A61K 39/395 424/141.1 |
| 6,110,487 A | 8/2000 | Timmons et al. | |
| 6,124,265 A | 9/2000 | Timmons et al. | |
| 6,159,495 A | 12/2000 | Timmons et al. | |
| 6,159,496 A | 12/2000 | Blanchard et al. | |
| 6,165,496 A | 12/2000 | Timmons et al. | |
| 6,268,454 B1 | 7/2001 | Song et al. | |
| 6,270,791 B1 | 8/2001 | Van Dyke et al. | |
| 6,270,793 B1 | 8/2001 | Van Dyke et al. | |
| 6,274,155 B1 | 8/2001 | Van Dyke et al. | |
| 6,274,163 B1 | 8/2001 | Blanchard et al. | |
| 6,316,598 B1 | 11/2001 | Van Dyke et al. | |
| 6,371,984 B1 | 4/2002 | Van Dyke et al. | |
| 6,379,690 B2 | 4/2002 | Blanchard et al. | |
| 6,432,435 B1 | 8/2002 | Timmons et al. | |

(Continued)

FOREIGN PATENT DOCUMENTS

| | | |
|---|---|---|
| DE | 184915 | 12/1905 |
| DE | 22643 | 10/1907 |

(Continued)

OTHER PUBLICATIONS

Zilberman et al., "Antibiotic-eluting medical devices for various applications" Journal of Controlled Release, 2008, vol. 130, pp. 202-215.*
Pillemer, L., E. E. Ecker, and J. R. Wells. "The specificity of keratins." The Journal of experimental medicine 69.2 (1939): 191.*
Belcarz, Anna, et al. "Covalent coating of hydroxyapatite by keratin stabilizes gentamicin release." Journal of Biomedical Materials Research Part B: Applied Biomaterials 89.1 (2009): 102-113.*
Rogers et al., Int Rev Cytol 251: 209-263 (2006) (Year: 2006).*
Fujii et al., J Biol Macromol 13: 92-106 (2013) (Year: 2013).*
Belcarz et al., Journal of Biomedical Materials Research Part B: Applied Biomaterials, 89: 102-113 (2009) (Year: 2009).*
Hill et al., Biomaterials 21: 585-593 (2010) (Year: 2010).*
Pillemer et al., The Journal of Experimental Medicine 69: 191-197 (1939) (Year: 1939).*
Zilberman et al., J Controlled Release 130: 202-215 (2008) (Year: 2008).*

(Continued)

*Primary Examiner* — Alton N Pryor
(74) *Attorney, Agent, or Firm* — Myers Bigel, P.A.

(57) ABSTRACT

Provided herein are keratin compositions (e.g., keratin gels, scaffolds, particulates, and the like) including a compound of interest, useful for release and/or delivery of the compound of interest (e.g., in vivo or in vitro). In some embodiments, the composition is a composition formulated for controlled release of the compound of interest.

25 Claims, 7 Drawing Sheets

(56) References Cited

U.S. PATENT DOCUMENTS

| | | | |
|---|---|---|---|
| 6,461,628 B1* | 10/2002 | Blanchard | A61K 8/042 424/402 |
| 6,544,548 B1 | 4/2003 | Siller-Jackson et al. | |
| 7,439,012 B2 | 10/2008 | Van Dyke | |
| 7,892,573 B2 | 2/2011 | Van Dyke | |
| 8,021,830 B2 | 9/2011 | Van Dyke | |
| 8,258,093 B2 | 9/2012 | Van Dyke | |
| 8,273,702 B2 | 9/2012 | Van Dyke | |
| 8,299,013 B2 | 10/2012 | Van Dyke | |
| 2007/0166348 A1 | 7/2007 | Van Dyke | |
| 2008/0038327 A1* | 2/2008 | Kelly et al. | 424/445 |
| 2008/0274165 A1* | 11/2008 | Van Dyke | A61K 38/015 424/447 |
| 2009/0004242 A1 | 1/2009 | Van Dyke | |
| 2009/0047260 A1 | 2/2009 | Van Dyke | |
| 2010/0197021 A1 | 8/2010 | Van Dyke | |
| 2011/0137329 A1 | 6/2011 | Van Dyke | |
| 2011/0300193 A1 | 12/2011 | Van Dyke | |

FOREIGN PATENT DOCUMENTS

| | | | |
|---|---|---|---|
| EP | 0468797 A2 | 1/1992 | |
| EP | 0 540 357 A2 | 5/1993 | |
| GB | 531446 A | 1/1941 | |
| GB | 2 241 253 A | 8/1991 | |
| JP | 52-148581 A | 12/1977 | |
| JP | 53-016091 A | 2/1978 | |
| JP | 54-137064 A | 10/1979 | |
| JP | 55-051095 A | 4/1980 | |
| JP | 56-030909 A | 3/1981 | |
| JP | Sho 55-98256 | 2/1982 | |
| JP | S57-109797 | 7/1982 | |
| JP | 1-174528 | 7/1989 | |
| JP | 2-051533 A | 2/1990 | |
| JP | 3-011099 A | 1/1991 | |
| JP | 4-082561 A | 3/1992 | |
| JP | 4-091138 A | 3/1992 | |
| JP | Hei 4-189833 | 7/1992 | |
| JP | 5-285374 A | 11/1993 | |
| JP | 5-285375 A | 11/1993 | |
| JP | 5-320358 A | 12/1993 | |
| JP | 6-100600 A | 4/1994 | |
| JP | 6-116300 A | 4/1994 | |
| JP | 6-336499 A | 12/1994 | |
| JP | 9-227565 A | 9/1997 | |
| JP | 10-291998 A | 11/1998 | |
| JP | 10-291999 A | 11/1998 | |
| JP | 10-337466 | 12/1998 | |
| JP | 2000-191792 A | 7/2000 | |
| JP | 2001-087754 A | 4/2001 | |
| JP | 2001-114647 A | 4/2001 | |
| NL | 51000577 | 12/1941 | |
| RU | 2 106 154 C1 | 3/1998 | |
| RU | 2 108 079 C1 | 4/1998 | |
| WO | WO 91-02538 A1 | 3/1991 | |
| WO | WO 93/10827 A1 | 6/1993 | |
| WO | WO 93/12819 A1 | 7/1993 | |
| WO | WO 98/08550 A1 | 3/1998 | |
| WO | WO 99/26570 A1 | 6/1999 | |
| WO | WO 99/26595 A1 | 6/1999 | |
| WO | WO 99/51175 A1 | 10/1999 | |
| WO | WO 00/76437 A1 | 12/2000 | |
| WO | WO 01/19283 A2 | 3/2001 | |
| WO | WO 01/19305 A1 | 3/2001 | |
| WO | WO 01/64033 A2 | 9/2001 | |
| WO | WO 02/45508 A1 | 6/2002 | |
| WO | WO 03/011894 A1 | 2/2003 | |
| WO | WO 03/064449 A2 | 8/2003 | |
| WO | WO 03/086491 A2 | 10/2003 | |
| WO | WO 2006135362 A1 * | 12/2006 | A61K 9/0095 |
| WO | WO-2006135362 A1 * | 12/2006 | A61K 9/0095 |
| WO | WO 2007/050387 A2 | 3/2007 | |
| WO | WO 2008/070091 A1 | 6/2008 | |
| WO | WO 2008/130607 A2 | 10/2008 | |

OTHER PUBLICATIONS

International Search Report and Written Opinion, PCT/US11/27397, dated Apr. 29, 2011.

Gillis, J.N.; et al; "Selective retention of oxygen using chromatographic columns containing metal chelate polymers."; Analytical Chemistry; vol. 57(8), 1985, pp. 1572-1577.

Goddard, D.R. et al; "A Study on Keratin."; Journal of Biological Chemistry; vol. 106, 1934, pp. 605-614.

Gough, K.H. et al; "Amino acid sequences of alpha-helical segments from S-carboxymethylkerateine-A. Complete sequence of a type-I segment."; Biochemical Journal; vol. 173 (2), 1978, pp. 373-385.

Green, M.R.; Basketter, D.A.; Couchman, J.R.; Rees, D.A.; "Distribution and number of epidermal growth factor receptors in skin is related to epithelial cell growth.;" Developmental Biology; vol. 100, 1983, pp. 506-512.

Greven, R.; et al.; "Morphological origin of the S-carboxymethyl kerateines of wool."; Textile Research Journal vol. 56; 1986, pp. 523-526.

Grotendorst, G.R.; et al.; "Novel transforming growth factor β response element controls the expression of the connective tissue growth factor gene."; Cell Growth and Differentiation; vol. 7, 1996, pp. 469-480.

Han, C.H.; et al; "Effect of glycerol addition on the structure and properties of soluble wool keratose films."; Journal of the Korean Fiber Society; vol. 37,No. 8, 2000, pp. 442-447.

Hanukoglu, I.; et al.; "The cDNA sequence of a human epidermal keratin: Divergence of the sequence but conservation of structure among intermediate filament proteins." Cell; vol. 31, 1982, pp. 243-252.

Happey, F.; "Polycrystralline structure of wool." Nature; No. 4218, 1950, pp. 397-398.

Happey, F.; Wormell, R. L.; "Regenerated keratin fibers from wool." Journal Textile Inst.; vol. 40, 1949, pp. T855-69.

Happey, F.; Wormell, R. L.; "Regenerated keratin fibers."; Nature ; vol. 163, 1949, p. 18.

Harding, H.W.J.; et al; "Enzymic conversion of arginine to citrulline in a hair protein precusor."; Proceedings of the Australian Biochemical Society; ; vol. 9, 1976, pp. 18.

Harding, H.W.J.; Rogers, G.E.; "Formation of ε (y-Glutamyl) lysine cross-link in hair proteins. Investigation of transamidases in hair follicles." The Journal of Biochemistry; vol. 11, No. 15, 1972 pp. 2858-2863.

Hardy, M.H.; "The Secret life of the hair follicle."; Trends in Genetics; vol. 8, No. 2, 1992, pp. 55-60.

Harrap, B.S.; et al; "Soluble derivatives of feather keratin. (I) Isolation, fractionation and amiino acid composition." Biochemistry Journal; vol. 92, 1964, pp. 8-18.

Harris, M.; et al.; "Testing for oxidation damage of wool by alkali solubility." The Textile Manufacturer; vol. 63, 1937, pp. 36,37.

Hewish, D.R.; et al; "In vitro growth and differentiation of epithelial cells derived from post-embryonic hair follicles."; Australian Journal of Biological Sciences; vol. 35, No. 1, 1982, pp. 103-109.

Hiroshi, S.; et al; "Differential Thermal Analysis of component proteins from wool." Institute for Chemical Research, Kyoto University, Uji, Kyoto; vol. 38, 1982, pp. 517-522.

Hogg, D.M.; et al; "Amino acid sequences of alpha-helical segments from S-carboxymethylkerateine-A. Tryptic and chymotryptic peptides from a type II segment"; Biochemical Journal; vol. 173(2), 1978, pp. 353-363.

Horn, J.C.; Speakman, P.T.; "Relative molecular masses of reduced wool keratin polypeptides" Biochemistry Society Transcript, vol. 14, 1986, pp. 333, 334.

Hu, J.; et al; "Preparation of stable solution of keratin from human hair and structure and properties of the cast film."; Gaofenzi Cailiao Kexue Yu Gongcheng; vol. 18 (2), 2002, pp. 131-133.

Humphries, M.; "Protein-silicone copolymers."; Cosmetics News; vol. 16, No. 92, 1993, pp. 313-318.

Hynd, P.I.; et al; "Amino acid transport in wool and hair follicles."; Experimental Dermatology; vol. 8, 1999, pp. 325-326.

Hübner, G.; et al.; "Strong induction of activin expression after injury suggests an important role of activin in wound repair.";

(56) References Cited

OTHER PUBLICATIONS

Developmental Biology; vol. 173, 1996, pp. 490-498.
Igarashi, A.; et al.; "Regulation of connective tissue growth factor gene expression in human skin fibroblasts and during wound repair." Molecular Biology of the Cell; vol. 4, 1993, pp. 637-645.
Ikkai, F.; et al; "Dynamic light scattering and circular dichroism studies on heat-induced gelation of hard-keratin protein aqueous solutions."; Biomacromolecules, vol. 3, No. 3, 2002, pp. 482-487.
Ito, H.; et al; "Biocompatability of denatured keratins from wool."; Kobunshi Ronbunshu; vol. 39(4), 1982, pp. 249-256.
Iwatsuki, K.; Viac, J.; Reano, A; Morera, A; Staquet, M.J.; Thivolet, J.; Monier, J.C.; "Comparative studies on the naturally ocurring antikeratin antibodies in human sera."; The Journal of Investigative Dermatology; vol. 87, No. 2, 1986, pp. 179-184.
Jahoda, C.A.B.; et al.; "Dermal-Epidermal Interactions: Adult Follicle-derived cell populations and hair growth."; Dermatologic Clinics; vol. 14, No. 4 1996, pp. 573-583.
Jenkins, B.J. ; et al; "Isolation and characterization of a sheep cysteine-rich cuticle keratin pseudogene."; DNA Sequence; vol. 3, 1992, pp. 181-184.
Jenkins, B.J. et al; "Differential expression of genes encoding a cysteine-rich keratin in the hair cuticle."; Journal of Investigative Dermatology; vol. 103, 1994, pp. 310-317.
Jezowska-Trezebiatowska, B.; et al; "New cobalt (II) complexes, reversibly binding oxygen in aqueous solution."; Bulletin de l'Academie Polonaise des Sciences, Serie des Sciences Chimiques; vol. 20 (3), 1972, pp. 187-192.
Johnson, P.C.; et al; "Oxidative metabolism and blood flow regulation: The search for the missing link."; Journal of Vascular Research; vol. 37 (1) 2000, pp. 83.
Jones, C.M.; et al.; "Involvement of Bone Morphogenetic Protein-4 (BMP-4) and Vgr-1 in morphogenesis and neurogenesis in the mouse."; Development; vol. 111, 1991, pp. 531-542.
Jones, L.N.; "Studies on Microfibrils from alpha-Keratin."; Biochimica et Biophysica Acta ; vol. 446. 1976, pp. 515-524.
Jones, L.N.; et al; "Studies of developing human hair shaft cells in vitro."; Journal of Investigative Dermatology; vol. 90, No. 1, 1988, pp. 58-64.
Jozefowicz, M.; Jozefonvicz, J; "Functional Polymers and Cells"; Biomaterials; vol. 16, No. 4, 1988, pp. 831-870.
Katoh, K.; et al; "Multi-functionalization of fiber made of natural polymer."; Aichi-ken Sangayo Gijutsu Kenkyusho Kenkyu Hokoku; vol. 1, 2002, pp. 174-177.
Katsuumi, K.; Ito, M; Kazama, T.; Sato, Y.; "Two dimensional electrophoretic analysis of human hair keratins, especially hair matrix proteins." Archives of Dermatological Research; vol. 281, 1989, pp. 495-501.
Kawano, Y.; et al; "Film and gel of keratins."; Kagaku to Seibutsu; vol. 13 (5), 1975, pp. 291-292.
Kemp, D.J. et al; "Differentiation of avian keratinocytes. Characterization and relationships of the keratin proteins of adult and embryonic feathers and scales."; Biochemistry; vol. 11, No. 6, 1972, pp. 969-975.
Kemp, D.J.; Rodgers, G.E.; "Immunological and immunofluorescent studies on keratin of the hair follicle."; Journal of Cell Science; vol. 7, 1970, pp. 273-283.
Kikkawa, M.; et al; "Solubilization of keratin. Solubilization of feather keratin by oxidation with performic acid."; Hikaku Kagaku,(Leather Chemistry) vol. 20(3), 1974, pp. 151-162.
Klement, V.; et al; "The use of computer-analysis for the quantification of 2-D electrophoretic hair keratin patterns—a pilot study."; Journal of the Forensic Science Society; vol. 24, No. 4, 1984, pp. 440.
Koga, J. et al.; "FTIR study on structural transformation of keratin films induced by stretching."; Journal of Applied polymer Science; vol. 37, 1989, pp. 2131-2140.
Kothapalli, D.; et al.; "Transforming growth factor β induces anchorage-independent growth of NRK fibroblast via a connective tissue growth factor-dependent signaling pathway." Cell Growth and Differentiation; vol. 8, 1997, pp. 61-68.
Kowalska, K.; et al; "New bacterial peptides isolated from structural proteins (keratin of porcine bristle)."; Peptides; Proceedings of the European Peptide Symposium, 25th, 1998, pp. 792-793.
Kozlowski, H.; et al; "Nickel (II) complexes with sulfhydryl containing pepetides. Potentiometric and spectroscopic studies."; Journal of Inorganic Biochemistry; vol. 29 (3), 1987, pp. 187-197.
Kuczek, E.S.; et al; "Sheep wool (glycine+tyrosine)—rich keratin genes: a family of low sequence homology."; European Journal of Biochemistry; vol. 166, 1987, pp. 79-85.
Kulkarni, V.G.; "Further studies on the microfibrils from wool keratin. Part I: the isolation of microfibrils."; Textile Research Journal; vol. 46, No. 11, 1976, pp. 833-835.
Kurimoto, A.; et al.; "Conjugation of keratin sponge with bioactive substances utilizing free cysteine residues. Conjugation of lysozyme."; Nippon Kagakkai Koen Yokoshu; vol. 7, No. 2, 2001, pp. 818.
Kvedar, J.C.; et al.; "Cytokeratins of the bovine hoof : classification and studies on expression."; Biochimica et Biophysica Acta; vol. 884, 1986, pp. 462-473.
Lambre, C.R.; Alaoui-Slimani, N.; Bignon, J.; "An enzyme immunoassay for the auto-antibodies to keratin in normal human serum and in pleural fluids from patients with various malignant or non-malignant lung diseases."; Journal of Clinical and Laboratory Immunology; vol. 20, 1986, pp. 171-176.
Laplaza, C.E.; et al; "Helix-loop-helix-peptide as scaffolds for the construction of bridged metal assemblies in proteins: The spectroscopic A-cluster structure in carbon monoxide dehydrogenase."; Journal of the American Chemical Society, vol. 123, (42), 2001, pp. 10255-10264.
Lee, K.Y.; "Characterization of Silk Fibroin/S-carboxymethyl kerateine surfaces: Evaluation of the biocompatibility by contact angle measurement."; Fibers and Polymers; vol. 2, No. 2, 2001, pp. 71-74.
Leeder, J.D.; et al; "Readily extracted proteins from Merino wool."; Textile Research Journal; vol. 52, No. 4, 1982, pp. 245-249.
Lennox, F.G.; "Protein fibers. Chemistry."; Review of Textile Progress Journal; vol. 17, 1967, pp. 81-97.
Lennox, F.G.; et al.; "Photochemical degradation of keratins."; Photochemistry and Photobiology; vol. 9, No. 4, 1969, pp. 359-367.
Leon, N.H.; "The chemical reactivity and modification of keratin fibres." Textile Progress vol. 7, No. 1975, pp. 1-81.
Letter,J.E.; Jordan,R.B.; "Complexing of Nickel(II) by cysteine, tyrosine and related ligands and evidence for zwitterion reactivity." Journal of the American Chemical Society; vol. 9, No. 97, 1975, pp. 2381-2390.
Ley, K.; et al; "Release of cuticle from wool by agitation in solutions of detergents."; Australian Journal of Biological Sciences; vol. 41, No. 2, 1988, pp. 163-176.
Ley, K.F.; et al; "Wool cuticle—new approaches to its production and protein characterization."; Proceedings of the Australian Biochemical Society; vol. 14, 1981, pp. 14.
Li, C-X.; et al; "Purification of natural antikeratin autoantibodies from natural human serum and their effect on human keratinocytes cultured in vivo."; British Journal of Dermatology; vol. 145, No. 5, 2001, pp. 737-748.
Lindley, H. et al.; "High-sulfur protein fractions of keratins."; *Applied Polymers Symposium*; vol. 18, No. 1, 1971, pp. 21-35.
Lindley, H.; et al; "The occurance of the Cys-Cys sequence in keratins."; Journal of Molecular Biology; vol. 30, No. 1, 1967, pp. 63-67.
Lindley, H.; et al; "The preparation and properties of a group of proteins from the high sulphur fraction of wool"; Biochemical Journal; vol. 128, No. 4, 1972, pp. 859-867.
Lindley, H.; et al; "The reactivity of the disulphide bonds of wool"; Biochemical Journal; vol. 139, No. 3, 1974, pp. 515-523.
Lindley,, H.; et al; "Disulphide interchange reactions involving cyclosystine and their relevance to problems of α-keratin structure" Biochemical Journal; vol. 108, No. 4, 1968, pp. 701-703.
Lissizin, Th.; "Behavior of keratin sulfur and cystin sulfur, in the oxidation of these proteins by potassium permanganate." Biochemistry Bulletin vol. 4, 1915, pp. 18-23.
Lissizin, Th.; "The oxidation products of keratin by oxidation with permanganate." Z. Physiology Chem. vol. 173, 1928, pp. 309-311.

(56) References Cited

OTHER PUBLICATIONS

Liu, S.M.; et al; "Transsulfuration, protein synthesis rate and follicle mRNA in the skin of young Merino lambs in response to infusions of methionine and serine."; British Journal of Nutrition; vol. 83, No. 4, 2000, pp. 401-409.

Lotay, S.S.; Speakman, P.T.; "Three-chain merokeratin from wool may be a fragment of the microfibril component macromolecule"; Nature; vol. 265, 1977, pp. 274-277.

Lyons, K.M.; et al.; "Patterns of expression of murine Vgr-1 and BMP-2a RNA suggest that transforming growth factor-β-like genes coordinately regulate aspects of embryonic development." Genes & Development; vol. 3, 1989, pp. 1657-1668.

Mack, J.W.; Torchia, D.A.; Steinert, P.M.; "Solid-State NMR Studies of the Dynamics and Stucture of Mouse Keratin Intermediate Filaments."; Biochemistry; vol. 27, No. 15. 1988, pp. 5418-5426.

MacKinnon, P.J.; et al; "An ultrahigh-sulphur keratin gene of the human hair cuticle is located at 11q13 and cross-hybridizes with sequences at 11p15."; Mammalian Genome; vol. 1, 1991 pp. 53-56.

MacLaren, J.A.; "The extent of reduction of wool proteins by thiols." The Australian Journal of Chemistry; vol. 15,No. 4, 1962, pp. 824-831.

Marikovsky, M.; et al.; "Appearance of heparin-binding EGF-like growth factor in wound fluid as a response to injury."; Proceedings of the National Academy of Sciences, USA; vol. 90, 1993, pp. 3889-3893.

Marshall, R.C. et al; "High-sulfur proteins in mammalian keratins: a possible aid in classification."; Australian Journal of Zoology; vol. 25, No. 1, 1977, pp. 121-132.

Marshall, R.C.; "Successful isoelectric-focusing of wool low-sulphur proteins.";Journal of Chromatography; vol. 172, 1979, pp. 351-356.

Marshall, R.C.; "Analysis of the proteins from single wool fibers by two-dimensional polyacrylamide-gel electrophoresis."; Textile Research Journal; vol. 51, No. 2, 1981, pp. 106-108.

Marshall, R.C.; "Changes in wool low-sulphur and high-sulphur protein-components following chemical defleecing."; Textile Research Journal; vol. 51, No. 6, 1981, pp. 384-388.

Marshall, R.C.; "Characterization of the proteins of human hair and nail by electrophoresis."; Journal of Investigative Dermatology; vol. 80, No. 6, 1983, pp. 519-524.

Marshall, R.C.; "Cysteine-rich proteins of mouse hair."; Proceedings of the Australian Biochemical Society; vol. 8, 1975, pp. 4.

Marshall, R.C.; "Forensic identification of hairs by electrophoresis."; Journal of the Forensic Society; vol. 24, No. 4, 1984, pp. 340.

Marshall, R.C.; "Genetic variation in the proteins of human nail."; Journal of Investigative Dermatology; vol. 75, No. 3, 1980, pp. 264-269.

Marshall, R.C.; et al; "An investigation of the relationship of wool textile properties to fiber protein composition."; Proceedings of the International Wool Textile Research Conf.; vol. 1, 1990, pp. 266-275.

Marshall, R.C.; et al; "Examination of proteins of wool cuticle by two-dimensional gel-electrophoresis."; Textile Research Journal; vol. 56, No. 12, 1986, pp. 772-774.

Alexander, P.; Earland, C.; "Structure of wool fibers—Isolation of an α and β-protein in wool." Nature; vol. 166, 1950.

Almog, J.; et al; "Reversible binding of dioxygen to mesoporphyrin IX derivatives at low temperatures."; Journal of the American Chemical Society; vol. 96(17), 1974, pp. 5600-5601.

Almog, J.; et al; "Reversible oxygenation and autoxidation of a capped porphyrin iron (II) complex."; Journal of the American Chemical Society; vol. 97(1), 1975, pp. 227-228.

Amiya, T.; et al; "Conformational studies of the α-helical proteins from wool keratins by c.d." International Journal of Biological Macromolecules; vol. 4, 1982, pp. 165-172.

Ando, H.; et al; "Separation and characterization of keratin components of merino wool. III: Removal of cuticle by ultrasonic irradiation." Bulletin of the Institute for Chemical Research, Kyoto University; vol. 31, No. 3, 1975, pp. 81-85.

Ashkenasy, G.; et al; "Assemblies of "hinged" iron-porphyrins as potential oxygen sensors."; Journal of the American Chemical Society; vol. 122, No. 6, 2000, pp. 1116-1122.

Baldwin, J.E.; et al; "Binding of dioxygen to iron (II), Reversible behavior in solution."; Journal of the American Chemical Society; vol. 95 (17), 1973, pp. 5757-5759.

Barr, M.; "Oxidation, reduction and hydroysis of wool keratin."; Iowa State Coll. Journal of Science, vol. 12, 1937, pp. 106-107.

Bawden, C.S.; et al; "Expression of bacterial cysteine biosynthesis genes in transgenic mice and sheep: toward a new in vivo acid biosynthesis pathway and improved wool growth." Transgenic Research; vol. 4, 1995, pp. 87-104.

Bawden, C.S.; et al; "Expression of wool intermediate filament keratin transgene in sheep fibre alters structure."; Transgenic Research; vol. 7, 1998, pp. 273-287.

Bawden, C.S.; et al; "Improvement of wool quality by transgenesis."; Science Update, Conf: OECD, 2001, pp. 67-76.

Bawden, C.S.; et al; "Sheep transgenesis with keratin and non-keratin genes: expression in the wool follicle for the modified fibre properties and growth rates."; Experimental Dermatology; vol. 8, 1999, pp. 342-343.

Berse, B.; et al.; "Vascular permeability factor (Vascular endothelial growth factor) gene is expressed differentially in normal tissues, macrophages, and tumors." Molecular Biology of the Cell; vol. 3, 1992, pp. 211-220.

Besse, D.; et al; "Synthesis of selenocysteine peptides and their oxidation to diselenide-bridged compounds."; Journal of Peptide Science; vol. 3 (6), 1997, pp. 442-453.

Bettex-Galland, M. et al.; "Advances in Protein Chemistry." Academic Press, vol. 20, 1965.

Bhatnagar, G.M. et al; "Difference sprectra of kerateine-B."; *International Journal of Protein Research*; vol. 1 No. 3, 1969, pp. 213-219.

Bhatnagar, G.M.; et al; "Assessment of confirmational changes in low-sulfur S-(carboxymethyl)keratin from wool."; Australian Journal of Biological Sciences; vol. 20, No. 4, 1967, pp. 827-836.

Bhatnagar, G.M.; et al; "The conformation of the high sulphur proteins of wool. I The preparation and properties of a water soluble metakeratin."; International Journal of Protein Research; vol. 1 (3), 1969, pp. 199-212.

Bhatnagar, G.M.; et al; "The conformation of the high-sulphur proteins of wool. II—Difference spectra of kerateine-B." International Journal of Protein Research I; 1969, pp. 213-219.

Blagrove, R.J.; Frenkel, M.J.; Gillespie, J.M.; "The electrophoresis of the high-tyrosine proteins of keratins on cellulose acetate strips."; Comparative Biochemistry Physiologoly; vol. 50B, 1975, pp. 571-572.

Blessing, M.; et al.; "Transgenic mice as a model to study the role of TGF-β-related molecules in hair follicles." Genes and Development; vol. 7, 1993, pp. 204-215.

Bradbury, J.H.; "The structure and chemistry of keratin fibers." Advanced Protein Chemistry; vol. 27, 1973, pp. 111-211.

Bradbury, J.H.; et al.; "Advances in Protein Chemistry." vol. 27, 1973, pp. 222-375.

Bradbury, J.H.; et al; "Observations by light and electron microscopy on wool cuticle fractions obtained by ultrasonics."; Textile Research Journal; vol. 33, No. 4, 1963, pp. 251-257.

Bradbury, J.H.; et al; "Separation of chemically unmodified histological components of keratin fibers and analyses of cuticles."; Nature; vol. 210, No. 5043, 1966, pp. 1333-1334.

Breinl, F.; et al; "The oxidative breaking up of keratin through treatment with hydrogen peroxide." Z.Physiol. Chemistry; vol. 52, 1907, pp. 158-169.

Broad, A.; Gillespie, J.M., Reis, P.J.; "The influence of sulphur-containing amino acids on the biosynthesis of high-sulphur wool proteins." Australian Journal of Biological Sciences; vol. 23, 1970, pp. 149-164.

Brown, L.F.; et al.; "Expression of vascular permeability factor (Vascular Endothelial Growth Factor) by epidermal keratinocytes during wound healing."; Journal of Experimental Medicine; vol. 176, 1992, pp. 1375-1379.

(56) References Cited

OTHER PUBLICATIONS

Brunner, H.; Brunner, A.; "Fractionation of tyrosine-rich proteins from oxidized wool by ion-exchange chromotography and preparative electrophoresis."; European Journal Biochemistry; vol. 32, 1973, pp. 350-355.
Bryson, W.G.; et al; "The analytical tools of proteomics provide new insights into the expression of the wool genome, keratin chemistry and textile processing."; Wool Tcehnology and Sheep Breeding; vol. 49, No. 4, 2001, pp. 246-260.
Cameron, J.H.; et al; "Nickel (II) and cobalt (II) complexes of potentially quinquedentate macrobicyclic ligands. Reversible binding to dioxygen to a cobalt (II) complex."; Journal of the Chemical Society, Dalton Transactions: Inorganic Chemistry; vol. 3, 1993, pp. 397-402.
Campbell, M.E.; Whiteley, K.J.; Gillespie, J.M.; "Compositional studies of high and low-crimp wools."; Australian Journal of Biological Sciences; vol. 25, 1972, pp. 977-987.
Carey, J.R.; et al; "Design and synthesis of novel metalloproteins through reversible encapsulation of metal complexes by proteins." Abstract of Papers, 222nd ACS National Meeting, 2001.
Chatani, E.; et al; "A film formation technology of wool keratin."; Textile and Fashion; vol. 14(5), 1997, pp. 227-235.
Chatani, E.; et al; "Research on merchandizing technology of wool keratin. Film formation technology of wool keratin."; Owari Textile Research Annual Report No. 93, 1998, pp. 93-101.
Clark, R.A.F. Editor; "The Molecular and Cellular Biology of Wound Repair."; Plenum Press 2nd Edition, 1996, 1988.
Crewther, W.G. et al; "Helix-rich fraction from the low-sulphur proteins of wool."; Nature; vol. 207,(4994), 1965, pp. 295.
Crewther, W.G.; Effect of aftertreatment on the stability of set wool fibers. Comments; Journal of the Society of Dyers and Colourist; vol. 86, No. 5, 1970, pp. 208.
Crewther, W.G.; "The concept of internal pH in wool fibers and the interpretation of data relating to setting."; Journal of the Society of Dyers and Colourist; vol. 81, (4), 1965, pp. 156-158.
Crewther, W.G.; "The viscoelasticity of alpha keratin fibers."; Experimental Dermatology; vol. 8 (4), 1999, pp. 343-344.
Crewther, W.G.; "Preparation and properties of large peptides from the helical regiones of the low-sulfur proteins of wool."; Applied Polymer Symposia; vol. 18, No. 1, 1971, pp. 1-20.
Crewther, W.G.; "Structure of .alpha.-keratin."; Textile Research Journal; vol. 42, No. 4, 1972, pp. 251-252.
Crewther, W.G.; "The stress-strain characteristics of animal fibers after reduction and alkylation."; Textile Research Journal; vol. 35, No. 10, 1965, pp. 867-877.
Crewther, W.G.; "Thiol-disulfide interchange reactions in the setting of single wool fibers." Journal of the Society of Dyers and Colourist; vol. 82, No. 1, 1966, pp. 54-58.
Crewther, W.G.; at al; "Effect of S-carboxymethylation of wool proteins on the iodination of tyrosine residues."; Textile Research Journal; vol. 41, No. 3, 1971, 99.267.
Crewther, W.G.; Dowling, L.M.; "The relation between the disulphide content of wool and the two-stage supercontraction of wool fibers in solution of LiBr."; Biochimica et Biophysica Acta; vol. 46, 1961, pp. 605-606.
Crewther, W.G.; et al; "Amino acid sequences of alpha-helical segments from S-carboxymethylkerateine-A. Complete sequence of a type II segment."; Biochemical Journal; vol. 173 (2), 1978, pp. 365-371.
Crewther, W.G.; et al; "Amino acid sequences of α-helical segments from S-carboxymethlykerateine-A. Tryptic and chymotryptic peptides from a type-II segment."; Biochemistry Journal; vol. 173, 1978 pp. 353-363.
Crewther, W.G.; et al; "Formation of various crosslinkages in wool and their effect on the supercontraction properties of the fibers."; Textile Research Journal; vol. 37, No. 9, 1967, pp. 736-745.
Crewther, W.G.; et al; "Low-sulfur proteins from α-keratins. Interrelationship between their amino acid compositions, α-helix contents, and the supercontraction of the parent keratin." Biopolymers, vol. 4, 1966, pp. 905-916.
Crewther, W.G.; et al; "Reduction of S-carboxymethlycysteine and methionine with sodium in liquid ammonia." Biochimica et Biophysica Acta; vol. 164, 1969, pp. 606-609.
Crewther, W.G.; et al; "Structure of intermediate filaments."; International Journal of Biological Macrmolecules; vol. 5, No. 5, 1983, pp. 267-274.
Crewther, W.G.; et al; "The chemistry of keratins."; Advance Protein Chemistry; vol. 20, 1965 pp. 191-346.
Crewther, W.G.; et al; "The preparation and properties of a helix-rich fraction obtained by partial proteolysis of low sulfur S-Carboxymethylkerateine from wool." The Journal of Biological Chemistry; vol. 242, No. 19, 1967, pp. 4310-4319.
Dale, H.N.; "Keratin and other coatings for pills."; Pharmacology Journal; vol. 129, 1932, pp. 494-495.
Damaglou, A.P.; et al; "The hydrolysis by thermolysin of dipeptide derivatives that contain substituted cysteine" Biochemical Journal; vol. 123, No. 3, 1971, pp. 379-384.
Darskus, R.L.; et al.; "Breed and species differences in the hair proteins of four genera of caprini." Australian Journal of Biological Sciences; vol. 24, 1971, pp. 515-524.
Darskus, R.L.; et al; "The possibility of common amino acid sequences in high sulphur protein fractions from wool." Australian Journal of Biological Sciences; vol. 22, 1969, pp. 1197-1204.
De Sanctis, G.; et al; "Mini-myoglobin—Electron paramagnetic resonance and reversible oxygenation of the cobalt derivative."; Journal of Molecular Biology; vol. 222, 1991, pp. 637-643.
Dedeurwaerder, R.A.; et al; "Selective extraction of protein fraction from wool keratin." Nature vol. 203, 1964, pp. 48,49.
Dobb, M.G.; et al; "Electron microscopy of fibrous keratins."; Symposuim of fibrous protein, Int Conf.; 1967, pp. 267-278.
Dowling, L.M.; Crewther, W.G.; Inglis, A.S.; "The primary structure of component 8c-1, a subunit protein of intermediate filaments in wool keratin."; Biochemistry Journal vol. 236, 1986, pp. 695-703.
Dowling, L.M.; Crewther, W.G.; Parry, D.A.D.; "The secondary structure of component 8c-1, of alpha-keratin."; Biochemistry Journal; vol. 236, 1986, pp. 705-712.
Dowling, L.M.; et al; "Effect of the solvent on the iodanation of a tyrosine derivative and its relation to iodination of wool."; Textile Research Journal; vol. 41, No. 1, 1971, pp. 65-69.
Dowling, L.M.; et al; "Isolation of components from the low sulphur proteins of wool by fractional precipitation."; Preparative Biochemistry, vol. 4(3), 1974, pp. 203-226.
Downes, A.M.; et al; "Evaluation of modified [35S] methionine and [35S] casein preparations as supplements for sheep"; British Journal of Nutrition; vol. 24, No. 4, 1970, pp. 1083-1089.
Downes, A.M.; et al; "Matabolic fate of parenterally administered sulphur containing amino acids in sheep and the effects on growth and composition of wool"; Australian Journal of Biological Sciences; vol. 23, No. 5, 1970, pp. 1077-1088.
Downes, A.M.; Ferguson,K.A.; Gillespie, J.M.; Harrap, B.S.; "A study of the proteins of the wool follicle." Australian Journal of Biological Science; vol. 19. 1966, pp. 319-333.
Dunn, S.M.; et al; "Regulation of hair gene expression."; Experimental Dermatology, vol. 8, 1999, pp. 341-342.
Earland, C.; et al; "Structure of keratin. II. Amino acid content of fractions isolated from oxidized wool."; Biochimica et Biophysica Acta; vol. 22, 1956, pp. 405-411.
Ebright, Y.W.; et al; "N-(Iodoacetyl)-p-phenylenediamine-EDTA: A regent for high-efficiency incorporation of an EDTA-metal complex at a rationally selected site within a protein."; Bioconjugate Chemistry; vol. 4 (3), 1993, pp. 219-225.
Edwards, B.; et al; "Chemical studies on powdered keratins." Journal of Biological Chemistry; vol. 154, 1944, pp. 593-596.
Elleman, T.C.; et al; Amino acid sequences of alpha-helical segments from S-carboxymethylkerateine-A. Statistical analysis; Biochemical Journal; vol. 173 (2), 1978, pp. 387-391.
Elleman, T.C.; et al; "Periodicity in high sulphur proteins from wool"; Nature; vol. 246, 1973, pp. 530-531.
Elod, E.: et al.; "Reactions of wool fiber and alterations in the fine structure."; Melliand Textillber; vol. 21, 1940, pp. 385-388.
Elod, E.; et al.; The nature of the reactivity of wool. Melliand Textilber; vol. 21, 1940, pp. 617-622.

(56) References Cited

OTHER PUBLICATIONS

Elod, E; et al; "The structure and reactivity of the woolen fiber. IX. The effect of H2O2 on wool."; Melliand Textilber; vol. 23, 1942, pp. 313-316.

Elod,E. et al.; "The infiltration of heavy metal sulfides in the keratin fiber." Chem Ber. vol. 74B, 1941, pp. 1759-1762.

Eriksson, A.; et al.; "PDGF α- and β-receptors activate unique and common signal transduction pathaways."; The EMBO Journal; vol. 11, 1992, pp. 543-550.

Filshie, B.K. et al; "The Fine Structure of α-Keratin." Journal of Molecular Biology; vol. 3, 1961, pp. 784-786.

Filshie, B.K.; Rodgers, G.E.; "An electron microscope study of the fine structure of feather keratin."; The Journal of Cell Biology; vol. 13, 1962, pp. 1-12.

Frank, S.; et al.; "Transforming growth factors β1, β2, and β3 and their receptors are differentially regulated during normal and impaired wound healing." The Journal of Biological Chemistry; vol. 271, 1996, pp. 10188-10193.

Frankel, M.J.; Powell, B.C.; Ward, K.A.; Sleigh, M.J., Rodgers, G.E.; "The keratin BIIIB gene family: Isolation of cDNA clones and stucture of a gene and a related pseudogene."; Genomics vol. 4, 1989, pp. 182-191.

Fraser, B.R.D, et al; "Intermediate Filaments in α-keratins." Proceeedings of the National Academy of Sciences, USA.; Biochemistry; vol. 83, 1986, pp. 1179-1183.

Fraser, R.D.B.; et al; "Disulphide bonding in α-keratin."; International Journal of Biological Macromolecules; vol. 10, issue 2, 1988, pp. 106-112.

Fraser, R.D.B.; et al; "Microscopic Observations of the Alkaline-Thioglycollate Extraction of Wool." Short Communications, Wool Textile Research Laboratory; vol. 12, 1953, pp. 484-485.

Fraser, R.D.B.; et al; "Molecular organization in Alpha-Keratin."; Nature; vol. 193, 1962, pp. 1052-1055.

Fraser, R.D.B.; Gillispie, J.M.; "Wool structure and biosysnthesis." Nature vol. 126 1976, pp. 650-654.

Fraser, R.D.B.; Macrae, T.P.; "Helical models of feather keratin structure." Nature; vol. 195, No. 4847, 1962, pp. 1167,1168.

Fraser, R.D.B.; MaCrae, T.P.; Rogers, G.E.; "Structure of Alpha-Keratin." Nature; vol. 183, 1959, pp. 592-594.

Fraser,R.D.B.; Gillespie, J.M.; Macrae,T.P.; "Tyrosine-rich proteins in keratins."; Comparative Biochemistry and Physiology; vol. 44B, 1973, pp. 943-949.

Fratini, A.; et al; "Dietary cysteine regulates the levels of mRNAs encoding a family of cysteine-rich proteins of wool."; Journal of Investigative Dermatology; vol. 102, 1994, pp. 178-185.

Frenkel, M.J. et al.; "Heterogeneity of tyrosine-rich proteins of wool."; Proceedings of the Australian Biochemical Society; vol. 7, 1974, p. 4.

Frenkel, M.J.; "Alkali susceptible amides in tyrosine-rich proteins of wool."; Proceedings of the Australian Biochemical Society; vol. 10, 1977, p. 21.

Frenkel, M.J.; et al.; "Studies of the ribonucleic-acids coding for the keratin complex of hair."; Proceedings of the Australian Biochemical Society; vol. 12, 1979, pp. 87.

Frenkel, M.J.; et al; "Factors influencing biosynthesis of tyrosine-rich proteins of wool."; Australian Journal of Biological Sciences; vol. 27, 1974, pp. 31-38.

Frenkel, M.J.; et al; "The keratin BIIIB gene family: isolation of cDNA clones and structure of a gene and a related pseudogene."; Genomics; vol. 4, No. 2, 1989, pp. 182-191.

Frenkel, M.J.; Gillespie, J.M.; Reis, P.J.; "Studies on the inhibition of synthesis of the tyrosine-rich proteins of wool."; Australian Journal of Biological Sciences; vol. 28, 1975, pp. 331-338.

Frenkel, M.J.; Gillespie, J.M.; Woods, E.F.;"The isolation and properties of a tyrosine-rich protein from wool: component 0.62."; European Journal Biochemistry; vol. 34, 1973, pp. 112-119.

Fujisawa, K.; et al; "Synthesis and characterization of zinc family thiolato complexes.";Abstracts, Symposium on Biofunctional Chemistry, vol. 14, 1999, pp. 52-53.

Gillespie, J.M. et al; "Evidence of homology in a high-sulphur protein fraction (SCMK-B2) of wool and hair α-keratins."; Biochemistry Journal; vol. 110, No. 2, 1968, pp. 193-198.

Gillespie, J.M. et al; "A comparative study of high-sulphur proteins from α-karatins." Comparative Biochemistry and Physiology; vol. 15, 1965, pp. 175-185.

Gillespie, J.M.; "Reaction of Sodium Borohydride with wool." Nature; vol. 183 No. 4657, 1959, pp. 322, 323.

Gillespie, J.M.; "Swelling of keratins in formic acid." Textile Research Journal; vol. 40, No. 9, 1970, pp. 853-855.

Gillespie, J.M.; "The isolation and properties of some soluble proteins from wool. (II) The preferential extracation of high-sulphur proteins."; Australian Journal of Biological Sciences; vol. 15, No. 1, 1962, pp. 262-277.

Gillespie, J.M.; "The isolation from wool of a readily extractable protein of low sulphur content." Biochimica et Biophysica Acta; vol. 27, 1958, pp. 225,226.

Gillespie, J.M.; "The probable role and location of high-glycine-tyrosine proteins in the structure of keratins." Biopolymers, vol. 17, 1978, pp. 2743-2745.

Gillespie, J.M.; "The relation between the crimp of wool and its content of high-sulfur proteins."; Textile Research Journal; vol. 35, No. 12, 1965, pp. 1128-1129.

Gillespie, J.M.; "Keratin structure and changes with copper deficiency."; *Australian Journal of Dermatology*; vol. 14, No. 3, 1973, pp. 127-131.

Gillespie, J.M.; Broad, A.; "A further study on the dietary-regulated biosynthesis of high-sulphur wool proteins." Biochemistry Journal; vol. 112, 1969, pp. 41-49.

Gillespie, J.M.; Darskus, R.L.; "Relation between the tyrosine content of various wools and their content of a class of protiens rich in tyrosine and glycine."; Australian Journal Biological Science; vol. 24, 1971, pp. 1189-1197.

Gillespie, J.M.; et al.; "Changes in the matrix proteins of wool and mouse hair following the administration of depilatory compounds." Australian Journal of Biological Sciences; vol. 33, 1980, pp. 125-136.

Gillespie, J.M.; et al.; "Proteins of the hard keratins of Echidna, Hedgehog, Rabbit, Ox and Man."; Australian Journal of Biological Sciences, vol. 30, 1977, pp. 401-409.

Gillespie, J.M.; et al; "The Diversity of Keratins"; Comparative Biochemistry and Physiology; vol. 47, No. 2,1974, pp. 339-346.

Gillespie, J.M.; et al; "Variable composition of hair and high-sulfur proteins in trichothiodystrophy."; Journal of Applied Cosmetology; vol. 7, No. 2, 1989, pp. 39-48.

Gillespie, J.M.; Frenkel, M.J.; "The macroheterogeneity of type I tyrosine-rich proteins of merino wool."; Australian Journal Biological Science; vol. 27, 1974, pp. 617-627.

Gillespie, J.M.; Inglis, A.S.; "High-sulphur proteins as a major cause of variation in sulphur content between α-keratins." Nature; vol. 207, 1965, pp. 1293,1294.

Gillespie, J.M.; Marshall, R.C.; "A comparision of the proteins of normal and trichothiodystrophic human hair." The Journal of Investigative Dermatology; vol. 80, 1983, pp. 195-202.

Gillespie, J.M.; Marshall, R.C.; Moore, G.P.; Panaretto, B.A.; Robertson, D.M.; "Changes in the proteins of wool following treatment of sheep with epidermal growth factor."; The Journal of Investigative Dermatology; vol. 79, No. 3, 1982, pp. 197-200.

Gillespie, J.M.; Reis, P.J.; "The dietary regulated biosynthesis of high-sulphur wool proteins."; Biochemistry Journal; vol. 98, 1966, pp. 669-677.

Gillespie, J.M.; Simmonds, D.H.; "Amino acid composition of a sulphur-rich protein from wool."; Biochimica et Biophysica Acta; vol. 39, 1960, pp. 538-539.

Gillespie,J.M.; "Proteins rich in glycine and tyrosine from keratins. "; Comparative Biochemistry and Physiology; vol. 41B, 1972, pp. 723-734.

Sizin, T.L.; "the occurance of azelaic acid among the oxidation products of keratin." Z. Physiology Chemistry: vol. 62, 1910, pp. 226-228.

(56) References Cited

OTHER PUBLICATIONS

Skerrow, D.; Skerrow, C.J.; Hunter, I.; "Epidermal alpha-keratin is neutral-buffer-soluable and forms intermediate filaments under physiological conditions in vitro."; Biochimica et Biophysica Acta; vol. 915. 1987, pp. 125-131.
Smith, A.L.; et al; "Oxidation of Wool—The Effect of Hydrogen Peroxide." Rayon Textile Monthly; vol. 39, 1936. pp. 39,40.
Smith, A.L.; et al; "Oxidation of Wool: The lead acetate test for hydrogen peroxide bleached wool." Journal of Research of the National Bureau of Standards, vol. 16, 1936, pp. 309-312.
Sparrow, L.G.; et al; "Further resolution of the low sulphur S-carboxymethylkerateine fraction from wool by acrylamide-gel electrophoresis."; Journal of Textile Institute; vol. 63, No. 11, 1972, pp. 619-621.
Starger, J.M.; Brown, W.E.; Goldman, A.E.; Goldman, R.D.; "Biochemical and immunological analysis of rapidly purified 10-nm filaments from baby hamster kidney (BHK-21) cells." The Journal of Cell Biology, vol. 78, 1978, pp. 93-109.
Stary, Z.; "Brominated keratin and oxykeratin."; Z. Physiology Chemistry; vol. 144, 1925, pp. 147-177.
Stary, Z.; "Solubility and digestibility of the degradation products of albumoids." Z. Physiology Chemistry; vol. 136, 1924, pp. 160-172.
Steinert, P.M.; et al; "In vitro studies on the synthesis of guinea pig hair keratin proteins." Biochimica et Biophysica Acta; vol. 312, 1973, pp. 403-412.
Stenn, K.S.; "The molecular and structural biology of hair, Introduction."; Annals of New York Academy of Sciences; vol. 83, 1959, pp. 359-512.
Stenn, K.S.; et al.; "Controls of hair Follicle cycling . . . "; Physiological Reviews; vol. 81, No. 1, 2001, pp. 449-494.
Stenn, K.S.; et al.; "Hair follicle growth controls." Dermatologic Clinics; vol. 14, No. 4, 1996, pp. 543-558.
Stenn, K.S.; et al.; "Molecules of the cycling hair follicle—a tabulated review." Journal of Dermatalogical Science 7(Suppl.) 1994, pp. 109-124.
Stephenson, N.A.; et al; "Preparation and dioxygen binding properties of a new cobalt (II) complex and the crystal structure of the corresponding copper (II) adduct."; Journal of the Chemical Society, Dalton Transactions: Inorganic Chemistry, 150th Anniv. Celebration issue, 1991, pp. 733-738.
Stokes,G.D.; Dunson, W.A.; "Passage of water and electrolytes through natural and artificial keratin membranes." Desalination; vol. 42, 1982, pp. 321-328.
Struessmann, A.; et al.; "Specific radiolabeling of keratin proteins by amidination."; Journal of Chromatography, vol. 268, 1983, pp. 306-310.
Suzuki, E.; et al; "X-ray diffraction and infrared studies of an α-helical fragment from α-keratin." Journal of Molecular Biology; vol. 73, 1973, pp. 275-278.
Tachibana, A. et al.; "Fabrication of wool keratin sponge scaffolds for long-term cell cultivation." Journal of Biotechnology, vol. 93, 2002 pp. 165-170.
Tanabe, T.; Tachibana, A.; Yamauchi, K.; "Keratins: prospective proteinous biomaterial."; Recent Research Developments in Protein Engineering; vol. 1(Pt.2), 2001, pp. 247-259.
Tazawa, T.; et al; "Anti-hair keratin monoclonal antibody (HKN-2)."; The Journal of Dermatology; vol. 12, 1985, pp. 313-317.
Thomas, H.; et al; "Isolation of the microfibrillar proteins of wool in the disulfide form." Melliand Textilberichte; vol. 65, No. 3, 1984, pp. 208-209.
Tsai, A.G.; et al; "High viscocity plasma expanders: Volume restitution fluids for lowering the transfusion trigger."; Biorheology, vol. 38 (2-3), 2001, pp. 229-237.
Tsai, A.G.; et al; "The unusual properties of effective blood substitutes. "; Keio Journal of Medicine; vol. 51 (1), 2002, pp. 17-20.
Tsuchida, E.; "Oxygen ligation of macromolecule-porphyrin complexes."; Journal of the Chemical Society of Japan; No. 6, 1988, pp. 845-852.
Tsuchida, E.; et al; "Cobalt (II)/poly(ethyleneimine) membrane with oxygen binding ability."; Makromolekulare Chemie; vol. 3 (10), 1982, pp. 693-696.
Tucker, D.J.; et al; "Variations in goat fiber proteins."; Australian Journal of Agriculture Research vol. 40, No. 3, 1989, pp. 675-683.
Ueyama, N.; et al; "A novel method for determining the chelation ability of the cysteine-containing peptides with 3,4-toluenedithiol. Application to .cents .2Fe-2S-ferredoxin model systems."; Bulletin of the Chemical Society of Japan; vol. 60 (1), 1987, pp. 283-287.
Van Neste, D.; "The growth of human hair in nude mice."; Dermatologic Clinics; vol. 14, No. 4, 1996, pp. 609-617.
Vasak, M.; et al; "Metal thiolate clusters in cobalt (II)-metallothionein."; Proceedings of the National Academy of Sciences of the United States of America; vol. 78 (11), 1981, pp. 6709-6713.
Vogeli, G.; et al; "High-Sulfur Protein Gene Expression in a Transgenic Mouse." Annals New York Academy of Sciences; vol. 642, 1991, pp. 21-30.
Ward, K.A.; et al.; "The structure of the wool keratin microfibrillar genes." Proceedings of the Australian Biochemical Society; vol. 15, 1983, pp. 70.
Ward, K.A.; "Changes in wool follicle keratinocyte protein-biosynthesis mediated by inhibitors of follicle bulb cell-proliferation."; Proceedings of the Australian Biochemical Society; vol. 9, 1976, vol. 9, pp. 57.
Ward, K.A.; "Study of keratin biosynthesis in isolated wool follicle cells." Proceedings of the Australian Biochemical Society; vol. 7, 1974, pp. 93.
Weber, K.; Geisler, N.; "The structural relation between intermediate filament proteins in living cells and the alpha-keratins of sheep wool" The EMBO Jjournal; vol. 1 No. 10, 1982, pp. 1155-1160.
Weiss, R.A.; Guilett, Y.A,G.; Freedberg, I.M.; Farmer, E.R.; Small, E.A.; Weiss, M.M.; Sun, T.T; "The use of monoclonal antibody to keratin in human epidermal disease: Alterations in immunohistochemical staining pattern." vol. 81, No. 3, 1983, pp. 224-230.
Werner, S.; et al.; "Large induction of keratinocyte growth factor expression in the dermis during wound healing." Proceedings of the National Academy of Sciences, USA; vol. 89, 1992, pp. 6896-6900.
Whitbread, L.A.; et al; "Expression of the intermediate filament gene, K15, in the basal cell layers of epithelia and the hair follicle."; Experimental Cell Research; vol. 244, 1998, pp. 448-459.
Widra, A.; "Ascoporogenesis by nannizzia grubyia on a soluble fraction of keratin." Mycopathologia et Mycologia Applicata; vol. 30, No. 2, 1966 pp. 141-144.
Wilson, B. W.; et al.; "Complete sequence of a type-I microfibrillar wool keratin gene."; Gene; vol. 73, No. 1, 1988, pp. 21-31.
Wilson, N.; et al; "The role of BMP-2 and BMP-4 in follicle initiation and the murine hair cycle."; Experimental Dermatology; vol. 8, No. 4, 1999, pp. 367-368.
Wolski, T.; Szumilo, H.; "Studies on the kinetics of dissolving feather keratin in the water-urea system." Acta Alimentaria Polinica; vol. 8, (32) No. 1-2, 1982, pp. 102-108.
Wormell, R. L.; "Regenerated fibers from wool." Brit. Rayon Silk Journal; vol. 26, No. 309, pp. 55, 1950.
Wormell, R.L.; "Regenerated protein fibres from wool and casein"; The Journal of the Textile Institute; vol. 39, 1948, T219-T224.
Wormell, R.L.; "Wool, silk and regenerated protein fibers-chemistry. " Rev. Textile Progress; vol. 9, 1957, pp. 51-62.
Wortmann, F.J.; et al.; "A method for isolating the cortex of keratin fibers."; Textile Research Journal; vol. 52, 1982, pp. 479-481.
Yakubovich, T.N.; Teslenko, V.V.; Zub, Y.L; "Carriers of molecular oxygen on the basis of metal complexes incorporated in polyorganosiloxane matrices."; Journal of Inorganic and Organometallic Polymers; vol. 6, No. 1, 1996, pp. 43-49.
Yamamura, T.; et al; "Conformation control of peptides by metal ions. Coordination confirmation correlation observed in a model for Cys-X-Y-Cys/M2+ in proteins."; Inorganic Chemistry; vol. 36 (21), 1997, pp. 4849-4859.
Yamauchi, K. et al.; "Novel proteinous microcapsules from wool keratins." Colloids and Sudaces, B: Biointerfaces; vol. 9, 1997, pp. 117-119.
Yamauchi, K.; "Dissolution of hair and wool. Keratin polymers," Kobunshi Kako; vol. 4i, No. 1, 1994, pp. 14-19.

(56) References Cited

OTHER PUBLICATIONS

Yamauchi, K.; "Perspective in chemistry and applications of keratins." Kobunshi; vol. 50, No. 4, 2001, pp. 240-243.
Yamauchi, K.; "Polymer films fom keratin."; Fragrance Journal; vol. 21 (5), 1993, pp. 62-67.
Yamauchi, K.; "Preparation of stable aqueous solution of keratins, and physicochemical and biochemical properties of films." Polymer Preprints-American Chemical Society, Division of Polymer Chemistry; vol. 39, No. 1, 1998, pp. 357-358.
Yamauchi, K.; et al.; "Cultivation of Mouse L929 Fibroblast Cells on Keratins."; Kobunshi Gakkai Yokoshu (Polymer Preprints), Japan; vol. 44, No. 3,1995, pp. 503.
Yamauchi, K.; et al.; "Preparation of stable aqueous solution of keratins, and physicochemical and biodegradational properties of films." Journal of Biomedical Materials Research; vol. 31, No. 4, 1996, pp. 439-444.
Yamauchi, K.; et al; "Enhanced cell adhesion on RGDS-carrying keratin film."; Material Science & Engineering, C.: Biomimetic and Supermolecular Systems; vol. C23, No. 4, 2003, pp. 467-472.
Yao, X.; et al; "Oxygen carrying porphyrin-protein complexes the effect of iron (II) prophyrin structure on dioxygen binding performance."; Research Communications in Biochemistry and Cell & Molecular Biology; vol. 5 (1&2) 2001, pp. 171-174.
Yoshimizu, H.; et al; "C CP/MAS NMR study of the conformation of stretched or heated low-sulfur keratin protein films." Macromolecules,; vol. 24, 1991, pp. 862-866.
Zackroff, R.V.; Goldman, R.D.; "In vitro assembly of intermediate filaments from baby hamster kidney (BHK-21) cells." Proceedings of the National Academy of Sciences, USA; vol. 76, No. 12, pp. 6226-6230.
Zahn, H. et al.; "Reactivity of amino acid side chains. 18. Reactions of p-fluoro-m,m'-dinitrodiphenyl sulfone and p,p'-difluro-m,m'-dinitrodiphenyl sulfone with wool keratin and silk fibroin."; Kolloid Zeitschrift fuer Polymere; vol. 5, 1973 pp. 289-298.
Zahn, H. et al.; "Wool as a biological composite structure."; Industrial & Engineering Chemistry Product Research and Development; vol. 19, 1980, pp. 496-501.
Zahn, H.; "Progress report on hair keratin research."; International Journal of Cosmetic Science; vol. 24, 2002, pp. 163-169.
Zahn, H.; "Structure and chemistry of wool fibers." Kolloid-Z; vol. 100, 1942, pp. 283-298.
Zahn, H.; "The role of mohair keratin research." Melliand Textilberichte; vol. 72, 1991, pp. 926-931.
Zahn, H.; "Wool research taking part in comtemporary chemistry and physics." Arbeitsgemeinschaft Forsch. Landes Nordheim-Westfalen; vol. 75, 1957, pp. 47-80.
Zahn, H.G.; et al; "2-Dimensional keratin patterns of human hair including cosmetically treated ones."; Journal of Forensic Science Society; vol. 24, No. 4, 1984, pp. 432.
Zahn,H. et al.; "Wool as a biological compounding material." Schriftenreihe des Deautschen Wollforschungsintitutes; vol. 76, 1978, pp. 18-25.
Marshall, R.C.; et al; "High sulphur proteins and α-keratins II.* Isolatioin and partial characterization of purified components from mouse hair,"; Australian Journal of Biological Sciences.; vol. 29, 1976, pp. 11-20.
Marshall, R.C.; et al; "High sulphur proteins from α-keratins I. Heterogeneity of the proteins from mouse hair."; Australian Journal of Biological Sciences; vol, 29, 1976, pp. 1-10.
Marshall, R.C.; et al; "Possible identification of specialty fibers y electrophoresis."; Textile Research Journal; vol. 54, No. 2, 1984, pp. 126-128.
Marshall, R.C.; et al; "Protein changes after short thermal treatments of wool fibrics."; Textile Research Journal; vol. 53, No. 12, 1983, pp. 792-794.
Marshall, R.C.; et al; "Sequence studies of wool proteins rich in glycine and aromatic residues."; Proceedings of the Australian Biochemical Society; vol. 12, 1979, pp. 12.

Marshall, R.C.; Gillespie, J.M.; "The keratin proteins of wool, horn and hoof from sheep." Australian Journal of Biological Sciences; vol. 30, 1977, pp. 389-400.
Marshall, R.C; et al.; "Heterogeneity and incomplete disulfide reduction in the high sulphur proteins of wool." Australian Journal of Biological Sciences; vol. 31, 1978, pp. 219-229.
Martin, P. "Wound Healing-Aiming for Perfect Skin Regeneration,"; Science; vol. 276, 1997, pp. 75-81.
Mason, E.D.; et al.; "Dorsal midline fate in *Drosophila* embryos requires twisted gastrulation, a gene encoding a secreted protein related to human connective tissue growth factor." Genes and Development vol. 8, 1994, pp. 1489-1501.
Matsunaga, A.; et al; "Studies on the chemical property of human hair keratin. Part I. Fractionation and amino acid composition of human hair keratin solubilized by performic acid oxidation."; Hikaku Kagaku; vol. 27(1), 1981, pp. 21-29.
Mazzoni, M.C.; et al; "Blood and plasma viscocity and microvascular function in hemodilution. A perspective from LaJolla, California."; European Surgical Research; vol. 34, (1-2), 2002 Ref. 35.
McCloghry, C.E.; et al; "Wool follicles initiate, develop and produce fibres in ovine foetal skin grafts."; Proceedings of the Australian Society of Animal Production; vol. 18, 1990, pp. 518.
McMillin, D.R.; Holwerda, R.A.; Gray, H.B.; "Preparation and spectroscopic studies of cobalt (II) stellacyanin"; Proceedings of the National Academy of Sciences; vol. 71, No. 4, 1974, pp. 1339-1341.
McMillin, D.R.; Rosenberg, R.C.; Gray, H.B.; "Preparation and spectroscopic studies of cobalt (II) derivatives of blue copper proteins."; Proceedings of the National Academy of Sciences; vol. 71, No. 12, 1974, pp. 4760-4762.
Mies, H.H.; et al.; "Preparation of soluble proteins from wool."; Leder; vol. 39, 1988, pp. 1-9.
Mies, H.H.; Zahn, H.; "Chromatographic and electrophoretic investigations of the properties of unprotected low-sulphur wool keratins."; Journal of Chromatography; vol. 405, 1987, pp. 365-370.
Mitsui, S.; Ohuchi, A; Hotta, M.; Tsuboi, R.; Ogawa, H.; "Genes for a range of growth factors and cyclin-dependent kinase inhibitors are expressed by isolated human hair follicles." British Journal of Dermatology; vol. 137, 1997, pp. 693-698.
Miwa, M.; et al; "Effects of fiber length on the tensile strength of epoxy/glass fiber and polyester/glass fiber composites." Journal of Applied Polymer Science; vol. 25, 1980, pp. 795-807.
Miyamoto, T.: et al; "Sorption Behavior of Heavy Metal Ions on S-Subtituted Kerateine Gels." Institute for Chemical Research; vol. 34, No. 10, 1978, pp. T-447-T-454.
Moll, R.; et al.; "The catalog of humans cytokeratins: Patterns of expression in normal epithelia, tumors and cultured cells." Cell; vol. 31, 1982, pp. 11-24.
Mueller, R.V.; et al.; "The effect of insulinlike growth factor I on wound healing variables and macrophages in rats." Archives of Surgery; vol. 129, 1994, pp. 262-265.
Nakamura, A.; et al; "Cysteine-containing oligopepetide model complexes of iron-sulfur proteins."; Advances in Inorganic Chemistry; vol. 33, 1989, pp. 39-67.
Nakamura, Y.; et al; "Cystine in wool. Relation between sulfhydryl group and supercontraction." Sen-i Gakkaishi, vol. 16, 1960, pp. 852-858.
Nancarrow, M.J. et al; "Expression of ornithine decarboxylase during embryonic development of wool follicles."; Experimental Dermatology; vol. 8, 1999, pp. 362-368.
Noishiki, Y.; et al; "Application of denatured wool keratin derivatives to an antithrombogenic biomaterial. Vascular graft coated with a heparinized keratin derivative."; Kobunshi Ronbunshu; vol. 39(4), 1982, pp. 221-227.
Norman, J.A.T.; et al; "Reversible complexes for the recovery of dioxygen."; Proceedings of the Annual IUCCP Symposium; 1987, pp. 107-125.
Okamoto, S.; "Formation of films from some proteins."; Nippon Shokuhin Kogyo Gakkaishi; vol. 24(1), 1977, pp. 40-50.
O'Shea, J.M.; et al; "The effect of ultrasonic irradiation on proteins." Australian Journal of Biological Sciences; vol. 26,1973, pp. 583-590.

(56) References Cited

OTHER PUBLICATIONS

Osterberg, R.; "Metal complexes of peptides."; Metal Catalog Lipid Oxidation; Sv. Inst. Konserveringsforsk, Symposium, Goteberg Sweden, 1967, pp. 119-127.
Panteleyev, A.A.; et al.; "Hair follicle predetermination."; Journal of Cell Science; vol. 114, 2001, pp. 3419-3431.
Parry, D.A.D.; et al; "Fibrous proteins: Scientific, Industrial and Medical aspects."; An Academic Press Fast Publication; vol. 1, 1979, pp. 1-132.
Parry, D.A.D.; et al; "Structure of α-keratin: Structural implication of the amino acid sequences of the type I and type II chain segments."; Journal of Molecular Biology; vol. 113, 1977, pp. 449-454.
Pauling, L.; Corey, R.B.; "The structure of feather rachis keratin." Proceedings of the National Academy of Sciences; vol. 37, No. 5, 1951, pp. 256-261.
Pauling, L.; Corey, R.B.; "The structure of hair, muscle, and related proteins."; Proceedings of the National Academy of Sciences; vol. 37, No. 5, 1951, pp. 261-271.
Peters, L.; "Affinity of ions for keratin."; Journal of Textile Institute; vol. 58, No. 4, 1967, pp. 179-180.
Peus, D., et al.; "Growth factors in hair organ development and the hair growth cycle." Dermatologic Clinins; vol. 14, No. 4, 1996, pp. 559-572.
Philpott, M.P.; et al.; "Whole hair follicle culture." Dermatologic Clinics; vol. 14, No. 4, 1996, pp. 595-607.
Powell, B.C.; "The keratin proteins and genes of wool and hair."; Wool Technology and Sheep Breeding; vol. 44, No. 2, 1996, pp. 100-118.
Powell, B.C.; et al; "The Notch signalling pathway in hair growth."; Mechanisms of Development; vol. 78, 1988, pp. 189-192.
Powell, B.C.; et al; "Characterization of a gene encoding a cysteine-rich keratin associated protein synthesized late in rabbit hair follicle differentiation."; Differentiation; vol. 58, 1995, pp. 227-232.
Powell, B.C.; et al; "Characterization of hair (wool) keratin intermediate filament gene domain."; Journal of Investigative Dermatology; vol. 102, 1994, pp. 171-177.
Powell, B.C.; et al; "Mammalian keratin gene families: organization of genes coding for the B2 high sulphur proteins of sheep wool."; Nucleic Acids Research; vol. 11, 1983, pp. 5327-5346.
Powell, B.C.; et al; "Regulation of Keratin Gene Expression in Hair Follicle Differentiation." Annals New York Academy of Sciences; vol. 642, 1991, pp. 1-20.
Powell, B.C.; et al; "The role of keratin proteins and their genes in the growth, structure and properties of hair."; EXS; vol. 78, 1997, pp. 59-148 Ref: 284.
Powell, B.C.; et al; "Transgenic sheep and wool growth: possibilities and current status."; Reproduction, Fertility, and Development; vol. 6, 1994, pp. 615-623.
Powell, B.C.; Kemp, D.J.; Partington, G.A.; Gibbs, P.E.M.; Rogers, G.E.; "Control of feather keratin synthesis by the availability of keratin mRNA."; Biochemical and Biophysical research Communications; vol. 68, No. 4, 1976, pp. 1263-1271.
Powell, B.C.; Rodgers, G.E.; "Cyclic hair-loss and regrowth in the transgenic mice overexpressing and intermediate filament gene."; The EMBO Journal vol. 9, No. 5, 1990, pp. 1485-1493.
Rana, T.M.; et al; "Specific cleavage of a protein by an attached iron chelate."; Journal of the American Chemical Society; vol. 112 (6), 1990, pp. 2457-2458.
Randall, V.A.; "The use of dermal papilla cells in studies of normal and abnormal hair follicle biology."; Dermatologic Clinics; vol. 14, No. 4 1996 pp. 585-594.
Ranford, J.D.; et al; "Matallodrugs. The role of thiolate proteins and metal-thiolate complexes."; Metallothioneins, Conference General Review; 1992, pp. 408-435.
Ranshoff, S.; et al; "Synthesis and characterization of new dioxygen carriers: a reexamination of the fly-over ligand system."; Inorganic Chemistry; vol. 29(16), 1990, pp. 2945-2947.
Raphael, K.A.; et al; "Protein and amino acid composition of hair from mice carrying the naked (N) gene."; Genetic Research, vol. 44, No. 1, 1984, pp. 29-38.
Rappolee, D.A.; et al.; "Wound macrophages express TGF-α and other growth factors in vivo: Analysis by mRNA phenotyping."; Science; vol. 241, 1988, pp. 708-712.
Rau, H.K; Snigula, H.; Struck, A.; Robert, B.; Scheer, H.; Haehnel, W.; "Design, synthesis and properties of synthetic chlorophyll proteins."; European Journal of Biochemistry; vol. 268, 2001, pp. 3284-3295.
Reis, P.J.; "Influence of dietary protein and methionine on the sulphur content and growth rate of wool in the millk fed lambs" Australian Journal of Biological Science; vol. 23, No. 1, 1970, pp. 193-200.
Reis, P.J.; "The growth and composition of wool—III. Variations in the sulphur content of wool."; Australian Journal of Biological Sciences; vol. 18, 1965, pp. 671-687.
Reis, P.J.; "The growth and composition of wool. IV. The differential response of growth and of sulphur content of wool to the level of sulphur containing amino acids given per abomasum" Australian Journal of Biological Science; vol. 20, No. 4, 1967, pp. 809-825.
Reis, P.J.; et al; "The utilization of abomasal supplements of proteins and amino acids by sheep with special reference to wool growth"; Australian Journal of Biological Sciences; vol. 25, 1972, pp. 1057-1071.
Reis, P.J.; et al; "The influence of abomasal and intervenous supplements of sulphur containing amino acids on wool growth rate"; Australian Journal of Biological Sciences; vol. 26, No. 1, 1973, pp. 249-258.
Reis, P.J.; et al; "The nutritional control of the growth and properties of mohair and wool fibers: a comparative review"; Journal of Animal Science; vol. 72, No. 7, 1994, pp. 1899-1907.
Reis, P.J.; Tunks, D.A.; Williams, O.B.; Williams, A. J.; "A relationship between sulphur content of wool and wool production by merino sheep."; Australian Journal of Biological Sciences; vol. 20, 1967, pp. 153-163.
Reis, P.J.; Variations in the S content of wool.; Biology Skin Hair Growth, Proceedings Symposium; 1964, pp. 365-375.
Rogers, G.E.; "Some observations on the proteins of the inner root sheath cells of hair follicles." Biochimica et Biophysica Acta; vol. 29. 1958, pp. 33-43.
Rogers, G.E. ; et al; "Keratin protofilaments and ribosomes from hair follicles."; Nature, vol. 205, 1965, pp. 77-78.
Rogers, G.E. et al.; "An approach to the investigation of protein biosynthesis in hair follicles." *Biology of Skin Hair Growth, Proceedings*, 1965, pp. 329-343.
Rogers, G.E.; "Genetic engineering for novel fibres."; Journal of the Textile Institute; vol. 91, part 3, Special Issue, 2000, pp. 24-31.
Rogers, G.E.; "Improvement of wool production through genetic engineering."; Trends in biotechnology (Personnal edition); vol. 8, 1990, pp. 6-11, 32 references.
Rogers, G.E.; "Proteins of the inner-root-sheath cells of hair follicles."; Biochimica et Biophysica Acta; vol. 29, 1958, pp. 33-43.
Rogers, G.E.; "Structural and biochemical features of the hair follicles."; Epidermis; 1964, pp. 179-236.
Rogers, G.E.; "Structure and biochemistry of keratin."; The Biological Basis of Medicine; vol. 6, 1969, pp. 21-57.
Rogers, G.E.; "Synthesis and cross-linking in the structure and growth of hair keratins." Clinics in Dermatology; vol. 6, No. 4, 1988, pp. 26-31.
Rogers, G.E.; et al; "Protein biosynthesis in hair follicles."; Biology of Skin Hair Growth., Proceedings ; 1965, pp. 329-343.
Rogers, G.E.; et al; "A procedure for the culture of hair follicles as functionally intact organoids."; Clinics in Dermatology; vol. 6, No. 4, 1988. pp. 36-41.
Rogers, G.E.; et al; "A sensitive assay for the enzyme activity in hair follicles and epidermis that catalyzes the peptidyl-arginine-citrulline posttranslational modification." Current Problems Dermatology; vol. 11, 1983, pp. 171-184.
Rogers, G.E.; et al; "Organization and expression of hair follicle genes."; Journal of Investigative Dermatology; vol. 101, 1993, pp. 50 S-55 S.

(56) References Cited

OTHER PUBLICATIONS

Rogers, G.E.; et al; "Themes in the molecular structure of hair—discussion." Annals New York Academy Science; vol. 642, 1991, pp. 100-106.
Roop, D.R.; Cheng, C.K.; Titterington, L.; Meyers, C.A.; Stanley, J.R.; Steinert, P.M.; Yuspa, S.H.; "Synthetic peptides corresponding to keratin subunits elicit highly specific antobodies." The Journal of Biological Chemistry; vol. 259, No. 13 1984, pp. 8037-8040.
Ross, S.A.; et al; "Nickel complexes of cysteine- and cystine-containing peptides: Spontaneous formation of disulfide-bridged dimers at neutral pH."; Inorganic Chemistry, vol. 37 (20), 1998, pp. 5358-5363.
Rouse, J.G.; et al; "A review of keratin-based biomaterials for biomedical applications." Materials; vol. 3, 2010, pp. 999-1014.
Rowlands, R.J.; "Periodicity in high-sulphur proteins from wool."; Nature; vol. 246, No. 5434, 1973, pp. 530-531.
Sadova, S. F.; et al; "Grafting of vinyl monomers onto wool keratin in an oxidation-reduction system."; Zh. Vses. Khim. O-va, vol. 12(5), 1967, pp. 596-597.
Sander, G.; et al; "Expresssion of the homeobox gene, Barx2, in wool follicle development."; Journal of Investigative Dermatology; vol. 115, No. 4, 2000, pp. 753-756.
Sauk, J.J. et al: "Reconstitution of cytokeratin filaments in vitro: Further evidence for the role of nonhelical peptides in filament assembly."; The Journal of Cell Biology; vol. 99, 1984, pp. 1590-1597.
Schaller, J.; et al; "Membranes prepared from keratin-polyacrylonitrile graft copolymers." Journal of Applied Polymer Sciences; vol. 25(5), 1980, pp. 783-794.
Schornig, M.; Neumann, R.; Rohrer, H.; "Synthesis of nerve growth factor mRNA in cultures of developing mouse whisker pad, a peripheral target tissue of sensory trigeminal neurons."; The Journal of Cell Biology; vol. 120, No. 6, Mar. 1993, p. 1471-1479.
Schrooyen, P.M.M.; et al; "Biodegrable films from selectively modified feather keratin dispersions."; Polymer Preprints; vol. 39, No. 2, 1998, pp. 160.
Schrooyen, P.M.M.; et al; "Polymer films from chicken feather keratin."; Book of Abstracts, American Chemical Society National Meeting Boston, 1998.
Shah, M.; et al.; "Neutralisation of TGF-$\beta_1$ and TGF-$\beta_2$ or exogenous addition of TGF-$\beta_3$ to cutaneous rat wounds reduces scarring." Journal of Cell Science; vol. 108, 1995, pp. 985-1002.
Extended European Search Report corresponding to European Application No. 11751497.6 dated Apr. 4, 2014.
Wormell RL. Regenerated fibers from wool. Brit. Rayon Silk J. 1950; 26(309): 55 Abstract.
Zackroff RV and Goldman RD. In vitro assembly of intermediate filaments from baby hamster kidney (BHK-21) cells. Proc. Natl. Acad. Sci. USA. Dec. 1979; 76(12): 6226-6230.
Reis PJ nd Gillespie JM. Effects of Phenylalanine and analogues of methionine and phenylalanine on the composition of wool and mouse hair. Australian Journal of Biological Sciences. 1985; 38(1); 151-163.
Nakamura A and Ueyama N. Cysteine-containing oligopeptide model complexes of iron-sulfur proteins. Advances in Inorganic Chemistry. 1989; (33): 39-67. Publisher Summary.
Canadian Intellectual Property Office. Examination Report, Canadian Patent Application No. 2,791,386, dated Mar. 28, 2018. 5 pages.
Canadian Intellectual Property Office. Examination Report, Canadian Patent Application No. 2,791,386, dated Feb. 7, 2019. 7 pages.

\* cited by examiner

CONTROLLED DELIVERY SYSTEM

RELATED APPLICATIONS

This application claims the benefit under 35 U.S.C. § 119(e) of U.S. Provisional Patent Application Ser. No. 61/311,003, filed Mar. 5, 2010, the disclosure of which is incorporated herein by reference in its entirety.

FIELD OF THE INVENTION

The present invention relates to keratin-based biomaterials and the use thereof for controlled delivery of compounds of interest.

BACKGROUND

Site-directed drug delivery systems are greatly needed in several areas of medicine. For example, localized drug delivery is needed in the treatment of local infections, such as in periodontitis, where the systemic administration of antimicrobial agents is ineffective.

The problem after systemic administration usually lies in the low concentration of the antimicrobial agent which can be achieved at the target site. A systemic dose increase may be effective to raise the local concentration, but it also may produce toxicity, microbial resistance and drug incompatibility.

Improved methods are needed for the controlled local delivery of drugs.

SUMMARY

Provided herein are keratin compositions (e.g., keratin gels, hydrogels, sponges, films, scaffolds, particulates, and the like) including a compound of interest, useful for release and/or delivery of the compound of interest (e.g., in vivo or in vitro). In some embodiments, the composition is a composition formulated for controlled release of the compound of interest. In some embodiments, the compound of interest is dispersed in the composition.

In some embodiments, the keratin composition comprises, consists of or consists essentially of a keratose, a kerateine, or combinations thereof. In some embodiments, the keratin composition comprises, consists of or consists essentially of acidic keratose, basic keratose, acidic kerateine, basic kerateine, or combinations thereof In some embodiments, the keratin composition comprises, consists of or consists essentially of α-keratose, γ-keratose, basic α-keratose, acidic α-keratose, basic γ-keratose, acidic γ-keratose, or combinations thereof. In some embodiments, the keratin composition comprises, consists of or consists essentially of α-kerateine, γ-kerateine, basic α-kerateine, acidic α-kerateine, basic γ-kerateine, acidic γ-kerateine, or combinations thereof.

In some embodiments, the keratin composition includes from 0.5, 1, 5, or 10 to 30, 40, 50, 60, 70, 80, 90, 99 or 100% by weight of keratose, kerateine, or combinations thereof. In some embodiments, the keratin composition includes from 0.5, 1, 5, or 10 to 30, 40, 50 or 60% by weight of said compound of interest.

In some embodiments, the invention provides kerateine compositions useful to provide a method of modulating the release of a compound of interest over time. Kerateine compositions may be designed or selected based on varying hydrolysis profiles over time to provide an appropriate release profile for the compound of interest. Such compositions may comprise varying ratios of components, including, but not limited to, alpha-kerateine, gamma-kerateine and keratin associated proteins (KAP). In some embodiments, kerateine compositions of the invention comprise from 45% to about 100% by weight alpha-kerateine. In other embodiments, kerateine compositions of the invention comprise from about 0% to about 55% by weight gamma-kerateine. In yet other embodiments, kerateine compositions may or may not comprise KAP or a substantial amount of KAP (e.g., less than about 5%, 1%, 0.5%, or 0.1% by weight of the composition).

In some embodiments, the compound of interest includes a protein or peptide (e.g., an antibody). In some embodiments, the compound of interest includes a growth factor. In some embodiments, the compound of interest includes an antibiotic (e.g., a fluorinated quinolone antibiotic such as ciprofloxacin).

In some embodiments, the composition is formulated for time release, e.g., over a time of from 1, 2, 4 or 5 to 10, 18, 24, 32 or 48 or more hours; or over a time of from 1, 2, 4 or 5 to 10, 18, 24, 32 or 48 or more days.

Methods of administering a compound of interest to a subject in need thereof (e.g., a human subject) are also provided, including steps of: providing the compositions as described herein; and administering the composition to said subject, wherein said compound of interest is provided in a treatment effective amount.

Also provided is the use of a keratin composition as described herein for release (e.g., controlled release and/or time release) of a compound of interest in vivo in a subject in need thereof (e.g., a human subject).

DETAILED DESCRIPTION OF THE PREFERRED EMBODIMENTS

Figure 1:
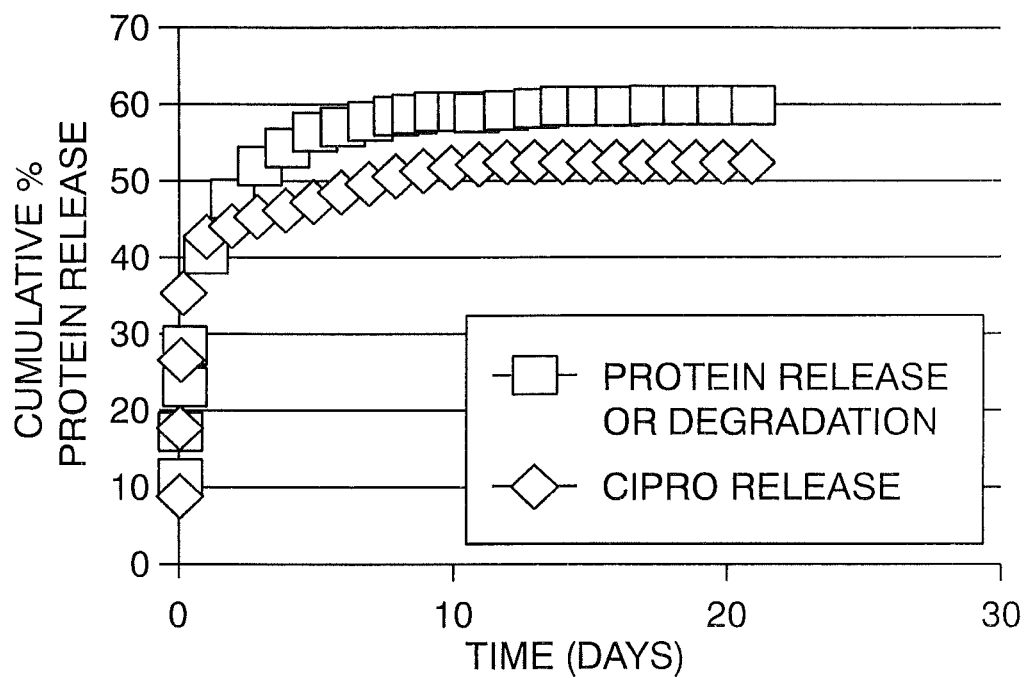
FIG. 1. Release of antibiotic (ciprofloxacin) from keratose gel.

Provided herein according to some embodiments are controlled delivery systems useful for the delivery of compounds of interest such as antibiotics, analgesics, etc. In some embodiments, the systems are particularly useful for the delivery of protein-based therapeutics such as growth factors or antibodies, which are susceptible to proteolytic degradation in vivo.

The disclosures of all cited United States Patent references are hereby incorporated by reference to the extent they are consistent with the disclosure herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

Preferred embodiments make use of keratin-based biomaterials. Other structural proteins such as collagen have known mammalian proteases that facilitate their rapid degradation in vivo. Keratin, in contrast, is the only known human structural protein to which mammalian proteases are not effective.

In one embodiment, keratin-based biomaterials of the invention do not comprise a significant amount of other structural proteins. For example, in some embodiments, keratin-based biomaterials of the invention do not comprise a significant amount of collagen (e.g., less than about 5%, 1%, 0.5%, or 0.1% by weight of the composition). In yet other embodiments, keratin-based biomaterials of the invention do not comprise a significant amount of chitosan (e.g., less than about 5%, 1%, 0.5%, or 0.1% by weight of the composition). In other embodiments, keratin-based biomaterials of the invention do not comprise a significant amount of glycosaminoglycans (e.g., less than about 5%, 1%, 0.5%, or 0.1% by weight of the composition). In yet other embodiments, keratin-based biomaterials of the invention do not comprise a significant amount of collagen and/or glycosaminoglycans.

To produce keratin biomaterials as described herein, subfamilies of keratin proteins may be isolated, and in some embodiments recombined into a reconstituted composition. The keratin compositions described herein according to some embodiments possess properties conducive to gelation and complexation of compounds of interest, which is useful to deliver the compounds of interest in a controlled fashion, e.g., to the cells and/or tissues of a patient in need of administration of the compounds of interest for therapy.

"Reconstituted composition" as used herein means a composition comprising different ratios of independently isolated fractions of keratin materials, including, but not limited to, alpha-keratose, acidic alpha-keratose, basic alpha-keratose, gamma-keratose, acidic gamma-keratose, basic gamma-keratose, alpha-kerateine, acidic alpha-kerateine, basic alpha-kerateine, gamma-kerateine, acidic gamma-kerateine, basic gamma-kerateine, KAPs, alpha-keratose monomers, or alpha-kerateine monomers. The composition is created by mixing together the desired proportions of the isolated fractions in solid, liquid, or hydrogel form. In some preferred embodiments, the reconstituted composition is substantially free of KAPs. In other preferred embodiments, the reconstituted composition is substantially free of alpha-keratose monomers and/or alpha kerateine monomers.

This system allows for the formation of compound-loaded keratin biomaterials, including gels such as hydrogels, scaffolds, particulates, and the like, wherein in some embodiments the delivery of said compounds are controlled by the degradation of the keratin and not by degradation of an exogenous encapsulation system or classical diffusion. This feature allows sustained release of said therapeutic compounds while maintaining high biological and pharmacological availability and activity. If a "burst" release of the therapeutic compound is desired, the keratin can be overloaded so a fraction of unbound compound is released by diffusion.

"Controlled release" as used herein refers to the release of a compound of interest wherein the amount of release over time is not dependent on the concentration of the compounds of interest. In some embodiments, the compounds of interest are bound, complexed to and/or protected by the keratin compositions such that their release rate is controlled by the rate of hydrolysis of the keratin compositions. In some embodiments, the controlled release may have a zero (constant) or substantially zero order release rate of the compounds of interest.

In other embodiments, the keratin composition may be formulated for a first (exponential) or substantially first order release rate of the compounds of interest. That is, the amount released over time is a function of the concentration of the compounds of interest.

In some embodiments, the keratin compositions are formulated for a time release, (release over a predetermined period of time) of compounds of interest, e.g., over a period of 1, 2, or 5 to 8, 10, 15, 20, 24, 36 or 48 or more hours. In some embodiments, the keratin compositions are formulated for a time release of compounds of interest over a period of 1, 2, or 5 to 8, 10, 15, 20 or 30 or more days. In other embodiments, the keratin compositions are formulated for a time release of compounds of interest over a period of 20, 25, 30, 35, 40, 45, 50, 55, 60, 65, 70, 75, 80, 85, 90, 95, 100, 105, 110, 115, or 120 or more days. In yet other embodiments, the keratin compositions are formulated for a time release of compounds of interest over a period of 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or longer. In yet other embodiments, the keratin compositions are formulated for a time release of compounds of interest over a period of 1, 2, 3, 4, 5, or 6 months or longer.

The compound of interest according to some embodiments may be "dispersed" in the keratin biomaterial such that the compound of interest is mixed, contained and/or distributed substantially evenly throughout the keratin composition.

In some embodiments, the composition includes from about 0.01, 0.1, 0.5, 1, or 2% to about 5, 10, 25, 50 or 70% or more by weight of keratin. In other embodiments, the compositions of the invention comprise from about 0.01, 0.1, 0.5, 1, or 2% to about 5, 10, 25, 50 70, 80, 90, 95% or more by weight of keratin.

In some embodiments, the composition includes from 0.01, 0.1, 0.5, 1, or 2% to 5, 10, 25, 50 or 70% by weight of the compound of interest. In yet other embodiments, the compositions of the invention comprise about 0.0001, 0.001, 0.01, 0.1, 0.5, 1, or 2% to 5, 10, 25, 50 or 70% by weight of the compound of interest In some embodiments, the keratin biomaterials are provided in gel form for administration, e.g., hydrogels. Hydrogels degrade by hydrolysis as opposed to proteolysis, which allows the keratin delivery system to preserve the biological or pharmacological activity of the compound prior to and/or during its release from the hydrogel. This may be particularly useful for the delivery of proteins and growth factors, which are notoriously unstable in the proteolytic environments of damaged tissues.

Hydrogel formation may be accomplished by simply by rehydrating the keratin powder e.g., with water or saline. The therapeutic compound can be dissolved in the liquid and readily incorporated into the hydrogel. Alternatively, dry therapeutic compound can be mixed with the powdered keratin and the two hydrated together. Binding of the therapeutic compound can be controlled by the sub-type of keratin employed as keratins with different structures and isoelectric points will bind compounds differently. Binding coefficients for the different keratin sub-types can be determined by techniques known in the art. Once determined, these binding coefficients and hydrogel degradation rates are controllable parameters that can be used to control the release profile of an optimized delivery system. Moreover, once the therapeutic compound(s) is (are) incorporated into the hydrogel, it can be lyophilized for later rehydration to improve shelf life of the product.

Once a particular therapeutic compound has been chosen to be included into a hydrogel, a delivery time frame may be established. From this delivery time frame, the most appropriate hydrogel composition may be selected based on its rate of hydrolysis. Because, as taught herein, the rate of release of the therapeutic compound mimics the rate of hydrolysis of the hydrogel, the user may elect to use a particular hydrogel to achieve the desired delivery rate over time based upon the rate of hydrolysis. For example, the higher the alpha keratose percentage is within a hydrogel, the more prolonged rate of hydrolysis, and thus the release of therapeutic compound with be more prolonged. Thus, the user may select the type and percentage composition of hydrogel to achieve the desired result of controlled release of a therapeutic compound over a pre-determined time window.

In other embodiments, the invention comprises providing the keratin composition together with a compound in interest in a sponge form. In some embodiments, sponges are formed by rapidly freezing and then subsequently lyophilizing the keratin material. In some embodiments, the kerateine sponges are created by freezing the hydrogels at $-80°$ C. for approximately 24 hrs and lyophilizing the resultant material.

In other embodiments, the invention comprises providing the keratin composition together with a compound of interest as a film. In some embodiments, films are formed by dispensing a keratin composition onto a surface or a container and evaporating the excess moisture. In a specific embodiment, films may be formed by adding about 3% (w/v) kerateine solutions to cultureware (e.g., 5 mg/cm$^2$) and evaporating the excess water by exposure to ambient air for an 8-12 hr period (e.g., at 37° C.).

The keratins as described herein can be loaded with many different types of compounds of interest or therapeutic compounds. The keratin biomaterials according to some embodiments preserve the biological activity of these compounds while being able to keep them in the local tissue environment and make them available for uptake and processing by resident cells.

A wide variety of therapeutic compounds may be delivered by the keratin biomaterials and methods of the present invention. "Therapeutic compound" is meant to include, for example, nucleic acids, proteins (e.g., antibodies such as monoclonal antibodies or fragments thereof), peptides, growth factors, oncolytics, anti-infectives, anxiolytics, psychotropics, immunomodulators, ionotropes, toxins such as gelonin and inhibitors of eukaryotic protein synthesis, and the like. Representative therapeutic drugs include prostaglandins, amphotericin B, methotrexate, cis-platin and derivatives, vincristine, vinblastine, progesterone, testosterone, estradiol, doxorubicin, epirubicin, beclomethasone and esters, vitamin E, cortisone, dexamethasone and esters, betamethasone valerete and other steroids, etc.

Therapeutic compounds for use in some embodiments of the present invention also include anti-infectives such as the fluorinated quinolone antibacterial ciprofloxacin and its derivatives, and the alkaloid compounds and their derivatives. Among the alkaloid derivatives are swainsonine and members of the vinca alkaloids and their semisynthetic derivatives, such as, for example, vinblastine, vincristine, vindesin, etoposide, etoposide phosphate, and teniposide. Among this group, vinblastine and vincristine, and swainsonine, are particularly preferred. Swainsonine (Creaven and Mihich, Semin. Oncol. 4:147 (1977)) has the capacity to stimulate bone marrow proliferation (White and Olden, Cancer Commun. 3:83 (1991)). Swainsonine also stimulates the production of multiple cytokines including IL-1, IL-2, TNF, GM-CSF and interferons (Newton, Cancer Commun. 1:373 (1989); Olden, K., J. Natl. Cancer Inst., 83:1149 (1991)). It also reportedly induces B- and T-cell immunity, natural killer T-cell and macrophage-induced destruction of tumor cells in vitro and, when combined with interferon, has direct anti-tumor activity against colon cancer and melanoma cancers in vivo (Dennis, J., Cancer Res., 50:1867 (1990); Olden, K., Pharm. Ther. 44:85 (1989); White and Olden, Anticancer Res., 10:1515 (1990)). Other alkaloids include paclitaxel (taxol) and synthetic derivatives thereof.

"Growth factors" include molecules that promote the regeneration, growth and survival of cells or tissue. Examples of growth factors include, but are not limited to, bone morphogenetic protein 2 (BMP-2), nerve growth factor (NGF) and other neurotrophins, platelet-derived growth factor (PDGF), erythropoietin (EPO), thrombopoietin (TPO), myostatin (GDF-8), growth differentiation factor-9 (GDF9), basic fibroblast growth factor (bFGF or FGF2), epidermal growth factor (EGF), hepatocyte growth factor (HGF), granulocyte-colony stimulating factor (G-CSF), vascular endothelial growth factor (VEGF), insulin-like growth factor (IGF), and granulocyte-macrophage colony stimulating factor (GM-CSF). There are many structurally and evolutionarily related proteins that make up large families of growth factors, and there are numerous growth factor families, e.g., the neurotrophins (NGF, BDNF, and NT3).

Keratins are a family of proteins found in the hair, skin, and other tissues of vertebrates. Hair is a unique source of human keratins because it is one of the few human tissues that is readily available and inexpensive. Although other sources of keratins are acceptable feedstocks for the present invention, (e.g., wool, fur, horns, hooves, beaks, feathers, scales, and the like), human hair is preferred for use with human subjects because of its biocompatibility. The human hair can be end-cut, as one would typically find in a barber shop or salon.

"Keratin derivative" as used herein refers to any keratin fractionation, derivative, subfamily, etc., or mixtures thereof, alone or in combination with other keratin derivatives or other ingredients, including, but not limited to, alpha keratose, gamma keratose, alpha kerateine, gamma kerateine, meta keratin, keratin intermediate filaments, and combinations thereof, including the acidic and basic constituents thereof unless specified otherwise, along with variations thereof that will be apparent to persons skilled in the art in view of the present disclosure.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

Subjects also include animal subjects, particularly mammalian subjects such as canines, felines, bovines, caprins, equines, ovines, porcines, rodents (e.g., rats and mice), lagomorphs, non-human primates, etc., for, e.g., veterinary medicine, laboratory research and/or pharmaceutical drug development purposes.

"Treat" refers to any type of treatment that imparts a benefit to a patient, e.g., a patient who is injured (e.g., a bone injury) or who is afflicted with or at risk for developing a disease (e.g., a peridontal disease). Treating includes actions taken and actions refrained from being taken for the purpose of improving the condition of the patient (e.g., the relief of one or more symptoms), delay in the onset or progression of the disease, etc.

Extracted keratin solutions are known to spontaneously self-assemble at the micron scale (see, e.g., Thomas et al., Int J Biol Macromol 1986; 8:258-64; van de Locht, Melliand Textilberichte 1987; 10:780-6). Self-assembly results in a highly regular structure with reproducible architectures, dimensionality, and porosity. When the keratin is processed correctly, this ability to self-assemble can be preserved and used to create regular architectures on a size scale conducive to molecular infiltration and/or attachment. When keratins are hydrolyzed (e.g., with acids or bases), their molecular weight is reduced, and they lose the ability to self-assemble. Therefore, processing conditions that minimize hydrolysis are preferred.

Soluble keratins can be extracted from human hair fibers by oxidation or reduction using methods known in the art (see, for example, Rouse J G, Van Dyke M E. A review of keratin-based biomaterials for biomedical applications. Materials 2010; 3:999-1014). These methods typically employ a two-step process whereby the crosslinked structure of keratins is broken down by either oxidation or reduction. In these reactions, the disulfide bonds in cystine amino acid residues are cleaved, rendering the keratins soluble. The cuticle is essentially unaffected by this treatment, so the majority of the keratins remain trapped within the cuticle's protective structure. In order to extract these keratins, a second step using a denaturing solution is employed. Alternatively, in the case of reduction reactions, these steps can be combined. Denaturing solutions known in the art include urea, transition metal hydroxides, surfactant solutions, and combinations thereof. Preferred methods use aqueous solutions of tris base (2-Amino-2-(hydroxymethyl)-1,3-propanediol) in concentrations between 0.1 and 1.0 M, and urea solutions between 0.1 and 10M, for oxidation and reduction reactions, respectively.

If one employs an oxidative treatment, the resulting keratins are referred to as "keratoses." If a reductive treatment is used, the resulting keratins are referred to as "kerateines" (See Scheme 1).

Scheme 1. General representations of (a) oxidation and (b) reduction disulfide crosslinks in keratin. These reactions cleave the sulfur-sulfur bond in cystine residues, thereby destroying the superstructure and rendering the keratins soluble in the reaction media. The resultant fractions are keratose (a) and kerateine (b).

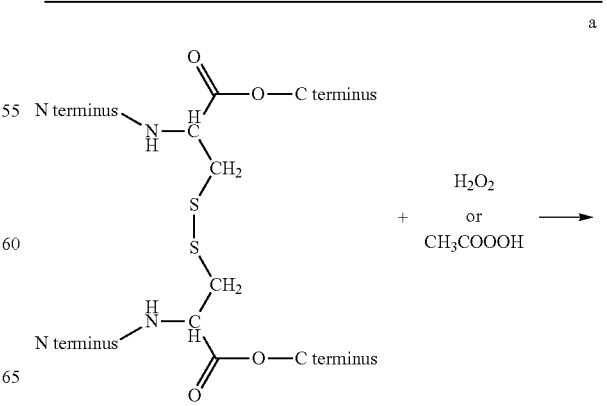

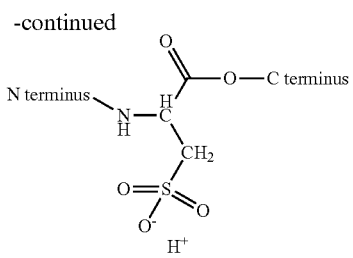

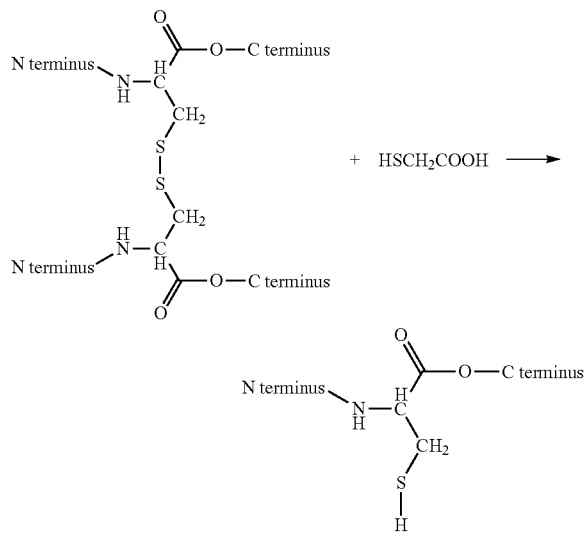

Crude (unfractionated) extracts of keratins, regardless of redox state, can be further refined into matrix (KAP and gamma), alpha, and/or charged (acidic or basic) fractions by a variety of methods such as isoelectric precipitation, dialysis, or high performance liquid chromatography (HPLC), as desired. In a crude extract, the alpha fraction begins to precipitate below pH 6 and is essentially completely precipitated by pH 4.2.

In some embodiments, KAP co-precipitate with the alpha fraction, thereby producing an alpha/KAP mixture. See Rogers et al., "Human Hair Keratin-Associated Proteins (KAPs)," Int'l ref. cytol. 251:209-263 (2006).

High molecular weight keratins, or "alpha keratins," (alpha helical), are thought to originate from the microfibrillar regions of the hair follicle, and monomers of alpha keratins typically range in molecular weight from about 40-85 kiloDaltons. They may also exist as higher-ordered structures, i.e., complexed into multimeric forms with each other or other keratins. Low molecular weight keratins, or "gamma keratins," or keratin-associated proteins (globular), are thought to originate from the matrix regions of the hair follicle, and typically range in molecular weight from about 3-30 kiloDaltons for KAP and 10-15 kiloDaltons for gamma keratins (see Rouse J G, Van Dyke M E. A review of keratin-based biomaterials for biomedical applications. Materials 2010; 3:999-1014).

In some embodiments, the keratin preparations (particularly alpha and/or gamma kerateine and alpha and/or gamma keratose) have an average molecular weight of from about 10 to 70 or 85 or 100 kiloDaltons. Other keratin derivatives, particularly meta-keratins, may have higher average molecular weights, e.g., up to 200 or 300 kiloDaltons.

Even though alpha and gamma keratins possess unique properties, the properties of subfamilies of both alpha and gamma keratins can only be revealed through more sophisticated means of purification and separation. Additional properties that are beneficial emerge and can be optimized upon further separation and purification of crude keratin extracts. Many protein purification techniques are known in the art, and range from the most simplistic, such as fractional precipitation, to the more complex, such as immunoaffinity chromatography. For extensive treatment of this subject, see Scopes R K (editor) Protein Purification: Principles and Practice (3rd ed. Springer, New York 1993); Roe S, Protein Purification Techniques: A Practical Approach (2nd ed. Oxford University Press, New York 2001); Hatti-Kaul R and Mattiasson B, Isomation and Purification of Proteins (Marcel Dekker AG, New York 2003). For example, sub-families of acidic and basic keratin are separable by moving boundary electrophoresis. A preferred method of fractionation is ion exchange chromatography. We have discovered that these fractions possess unique properties, such as their differential effects on blood cell aggregation (see, e.g., U.S. Pat. No. 7,439,012 to Van Dyke).

In some embodiments, the keratin derivative comprises, consists or consists essentially of a particular fraction or subfraction of keratin. The derivative in some embodiments may comprise, consist or consist essentially of at least 80, 90, 95 or 99 percent by weight of said fraction or subfraction (or more).

In some embodiments, the keratin derivative comprises, consists of or consists essentially of acidic and/or basic, alpha and/or gamma keratose, where the keratose comprises, consists of or consists essentially of at least 80, 90, 95 or 99 percent by weight of acidic and/or basic, alpha and/or gamma keratose (or more).

Keratose Production. A preferred method for the production of keratoses is by oxidation with hydrogen peroxide, peracetic acid, or performic acid. A most preferred oxidant is peracetic acid. Preferred concentrations range from 1 to 10 weight/volume percent, the most preferred being approximately 2 w/v %. Those skilled in the art will recognize that slight modifications to the concentration can be made to affect varying degrees of oxidation, with concomitant alterations in reaction time, temperature, and liquid to solid ratio. It has also been discussed by Crewther et al. that performic acid offers the advantage of minimal peptide bond cleavage compared to peracetic acid. However, peracetic acid offers the advantages of cost and availability. A preferred oxidation temperature is between 0 and 100 degrees Celsius. A most preferred oxidation temperature is 37° C. A preferred oxidation time is between 0.5 and 24 hours. A most preferred oxidation time is 10 hours. A preferred liquid to solid ratio is from 5 to 100:1. A most preferred ratio is 20:1. After oxidation, the hair can be rinsed free of residual oxidant using a copious amounts of purified water.

The keratoses may be extracted from the oxidized hair using an aqueous solution of a denaturing agent. Protein denaturants are well known in the art, but preferred solutions include urea, transition metal hydroxides (e.g. sodium and potassium hydroxide), ammonium hydroxide, and tris(hydroxymethyl)aminomethane (Trizma® base). A preferred solution is Trizma base in the concentration range from 0.01 to 1M. A most preferred concentration is 0.1M. Those skilled in the art will recognize that slight modifications to the concentration can be made to effect varying degrees of extraction, with concomitant alterations in reaction time, temperature, and liquid to solid ratio. A preferred extraction temperature is between 0 and 100 degrees Celsius. A most preferred extraction temperature is 37° C. A preferred extraction time is between 0.5 and 24 hours. A most preferred extraction time is 2 hours. A preferred liquid to solid ratio is from 5 to 100:1. A most preferred ratio is 40:1. Additional yield can be achieved with subsequent extractions with dilute solutions of Trizma base or purified water. After extraction, the residual solids can be removed from solution by centrifugation and/or filtration.

Residual denaturing agent may be removed by dialysis against purified water or buffer solution. Concentration of the dialysis retentate may be followed by lyophilization or spray drying, resulting in a dry powder mixture of gamma and alpha keratoses as well as KAP. Alternately, an alpha/KAP mixture may be isolated from the crude extract solution by dropwise addition of acid until the pH of the solution reaches approximately 4.2. Preferred acids include sulfuric, hydrochloric, and acetic. A most preferred acid is concentrated hydrochloric acid. Precipitation of the alpha/KAP fraction begins at around pH 6.0 and continues until approximately 4.2. Fractional precipitation can be utilized to isolate different ranges of protein with different isoelectric properties. Precipitated alpha/KAP can be recovered by centrifugation, filtration, or the like. The alpha/KAP mixture is further purified by re-dissolving the solids in a denaturing solution. The same denaturing solutions as those utilized for extraction can be used. However, a preferred denaturing solution is Trizma base. Ethylene diamine tetraacetic acid (EDTA) can be added to complex and remove trace metals found in hair. A preferred denaturing solution is 100 mM tris base with 20 mM EDTA or DI water with 20 mM EDTA, if desired. If the presence of trace metals is not detrimental to the intended application, the EDTA step may be omitted. The alpha/KAP mixture can be re-precipitated from this solution by dropwise addition of hydrochloric acid to a final pH of 4.2, Isolation of the solid may be done by centrifugation, filtration or the like. This process can be repeated several times to further purify the alpha/KAP mixture, if desired, although significant destruction of amide bonds should be avoided according to some embodiments. In another preferred embodiment, the alpha/KAP fraction can be isolated from gamma-keratose by dialysis. Providing a high nominal low molecular weight cutoff membrane such that the gamma passes through the membrane and the alpha/KAP is retained can effect such separation. Preferred membranes are those having nominal low molecular weight cutoffs of 15,000 to 100,000 Da. Most preferred membranes are those having nominal low molecular weight cutoffs of 30,000 and 100,000 Da.

The gamma keratose fraction can be isolated by addition to a water-miscible non-solvent. Suitable non-solvents include ethanol, methanol, acetone, and the like. A most preferred non-solvent is ethanol. To effect precipitation, the gamma keratose solution can be concentrated by removal of excess water. This can be done using vacuum distillation, falling film evaporation, microfiltration, etc. After concentration, the gamma keratose solution is added dropwise to an excess of cold non-solvent. A most preferred method is to concentrate the gamma keratose solution to approximately 10 weight/volume (w/v) % protein and add it dropwise to an 8-fold excess of cold ethanol. The precipitated gamma keratose can be isolated by centrifugation or filtration and dried. Suitable methods for drying include freeze drying (lyophilization), air drying, vacuum drying, or spray drying. A most preferred method is freeze drying. Alternately, the gamma keratose can be isolated by dialysis against purified water or buffer solution. Preferred membranes for dialysis are those having nominal low molecular weight cutoffs between 1,000 and 5,000 Da. Most preferred membranes for dialysis are those having nominal low molecular weight cutoffs of 3,000 and 5,000 Da. This solution can be concentrated by additional dialysis and reduced to a dry powder by lyophilization or spray drying.

Several different approaches to further purification can be employed to keratose solutions (e.g., crude, alpha or gamma keratose). Care must be taken, however, to choose techniques that lend themselves to keratin's unique solubility characteristics. One of the most simple separation technologies is isoelectric precipitation. Another general method for separating keratins is by chromatography. Several types of chromatography can be employed to fractionate keratin solutions including size exclusion or gel filtration chromatography, affinity chromatography, isoelectric focusing, gel electrophoresis, ion exchange chromatography, and immunoaffinity chromatography. These techniques are well known in the art and are capable of separating compounds, including proteins, by the characteristics of molecular weight, chemical functionality, isoelectric point, charge, or interactions with specific antibodies, and can be used alone or in any combination to affect high degrees of separation and resulting purity.

A preferred purification method is ion exchange (IEx) chromatography. IEx chromatography is particularly suited to protein separation owning to the amphiphilic nature of proteins in general and keratins in particular. Depending on the starting pH of the solution, and the desired fraction slated for retention, either cationic or anionic IEx (CIEx or AIEx, respectively) techniques can be used. For example, at a pH of 7 and above, both gamma and alpha/KAP keratose fractions are soluble and above their isoelectric points. As such, they are anionic and can be bound to an anionic exchange resin. However, if the pH is below approximately 6, the alpha in the alpha/KAP fraction will not bind to the resin and instead passes through a column packed with such resin. A preferred solution for AIEx chromatography is alpha/KAP solution, isolated as described previously, in weak buffer solution at a concentration between 0 and 5 weight/volume %. A preferred concentration is approximately 2 w/v %. It is preferred to keep the ionic strength of said solution initially quite low to facilitate binding to the AIEx column. This is achieved by using a minimal amount of acid to titrate a purified water solution of the keratin to between pH 5.3 and 6. A most preferred pH is 5.3. This solution can be loaded onto an AIEx column such as DEAE-Sepharose or Q-Sepharose, or processed in bulk without the use of a column. The solution that passes through the column can be collected and further processed as described previously to isolate a fraction of alpha powder.

The basic fraction (including KAP) binds readily due to its lower isoelectric point, and can be washed off the column using salting techniques known in the art. A preferred elution medium is sodium chloride solution. A preferred concentration of sodium chloride is between 0.1 and 2M. A most preferred concentration is 2M. The pH of the solution is preferred to be between 6 and 12. A most preferred pH is 11. In order to maintain stable pH during the elution process, a buffer salt can be added. A preferred buffer salt is Trizma base. A preferred concentration of Trizma base is 100mM. Those skilled in the art will recognize that slight modifications to the salt concentration and pH can be made to affect the elution of keratin fractions with differing properties. It is also possible to use different salt concentrations and pH's in sequence, or employ the use of salt and/or pH gradients to produce different fractions. Regardless of the approach taken, however, the column eluent can be collected and further processed as described previously to isolate purified fractions of alpha-keratose powders.

A complimentary procedure is also feasible using CIEx techniques. Namely, the alpha/KAP solution can be added to a cation exchange resin such as SP Sepharose (strongly cationic) or CM Sepharose (weakly cationic), and the basic (KAP) fraction collected with the pass through. The retained alpha fraction can be isolated by salting as previously described.

Kerateine Production. Similar to the methods described above for extraction and purification of keratoses, kerateines can be produced by reduction of hair fibers with thioglycolic acid or beta-mercaptoethanol. A most preferred reductant is thioglycolic acid (TGA). Preferred concentrations range from 0.1 to 10M, the most preferred being approximately 1.0M or 0.5M. Those skilled in the art will recognize that slight modifications to the concentration can be made to effect varying degrees of reduction, with concomitant alterations in pH, reaction time, temperature, and liquid to solid ratio. A preferred pH is between 9 and 11. A most preferred pH is 10.2. The pH of the reduction solution is altered by addition of base. Preferred bases include transition metal hydroxides and ammonium hydroxide. A most preferred base is sodium hydroxide. The pH adjustment is affected by dropwise addition of a saturated solution of sodium hydroxide in water to the reductant solution. A preferred reduction temperature is between 0 and 100 degrees Celsius. A most preferred reduction temperature is 37° C. A preferred reduction time is between 0.5 and 24 hours. A most preferred reduction time is 12 hours. A preferred liquid to solid ratio is from 5 to 100:1. A most preferred ratio is 20:1. Unlike the previously described oxidation reaction, reduction is carried out at basic pH. That being the case, keratins are highly soluble in the reduction media and are expected to be extracted. The reduction solution may therefore be combined with the subsequent extraction solutions and processed accordingly.

Reduced keratins are not as hydrophilic as their oxidized counterparts. As such, reduced hair fibers will not swell and split open as will oxidized hair, resulting in relatively lower yields. Another factor affecting the kinetics of the reduction/extraction process is the relative solubility of kerateines. The relative solubility rankings in water, from most to least soluble, is gamma-keratose>alpha-keratose>gamma-kerateine>alpha-kerateine. Consequently, extraction yields from reduced hair fibers are not as high. This being the case, subsequent extractions are conducted with additional reductant plus denaturing agent solutions. Typical solutions for subsequent extractions include TGA plus urea, TGA plus Trizma base, or TGA plus sodium hydroxide. After extraction, crude fractions of alpha/KAP and gamma kerateine can be isolated using the procedures described for keratoses. However, precipitates of gamma and alpha/KAP kerateine re-form their cystine crosslinks upon exposure to oxygen. Precipitates should, therefore, preferably be re-dissolved quickly so as to avoid insolubility during the purification stages, or precipitated in the absence of oxygen.

Purification of kerateine solutions can be conducted similar to those described for keratoses. Those skilled in the art will recognize that the chemical nature of kerateines varies from that of keratoses, primarily in the fate of pendant sulfur groups that will alter chemical properties such as isoelectric points. As such, modifications in the conditions for separation techniques such as ion exchange chromatography are needed for optimization.

In some embodiments, the keratin derivative comprises, consists or consists essentially of a particular fraction or subfraction of keratin. The derivative in some embodiments may comprise, consist or consist essentially of at least 80, 90, 95 or 99 percent by weight of said fraction or subfraction (or more).

In some embodiments, the keratin derivative comprises, consists of, or consists essentially of acidic and/or basic, alpha and/or gamma keratose, where the keratose comprises, consists of or consists essentially of at least 80, 90, 95 or 99 percent by weight of acidic and/or basic, alpha and/or gamma keratose (or more).

In some embodiments, the keratin derivative comprises, consists of, or consists essentially of acidic and/or basic, alpha and/or gamma keratose, where the keratose comprises, consists of, or consists essentially of at least 80, 90, 95 or 99 percent by weight of acidic and/or basic, alpha and/or gamma keratose (or more). In other embodiments, the keratin derivative comprises, consists of, or consists essentially of alpha/KAP keratose, where the keratose comprises, consist of, or consists essentially of at least 80, 90, 95 or 99 percent by weight of alpha/KAP keratose (or more).

In some embodiments, the keratin derivative comprises, consists of, or consists essentially of acidic and/or basic, alpha and/or gamma kerateine, where the kerateine comprises, consists of or consists essentially of at least 80, 90, 95 or 99 percent by weight of acidic and/or basic, alpha and/or gamma kerateine (or more). In other embodiments, the keratin derivative comprises, consists of, or consists essentially of alpha/KAP kerateine, where the kerateine comprises, consist of, or consists essentially of at least 80, 90, 95 or 99 percent by weight of alpha/KAP keratose (or more).

The basic alpha keratose is preferably produced by separating basic alpha keratose from a mixture comprising acidic and basic alpha keratose, e.g., by ion exchange chromatography, and optionally the basic alpha keratose has an average molecular weight of from 10 to 100 or 200 kiloDaltons. More preferably, the average molecular weight is from 30 or 40 to 90 or 100 kiloDaltons. Optionally, but in some embodiments preferably, the process further comprises the steps of re-dissolving said basic alpha-keratose in a denaturing and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of acidic alpha keratose, or less.

The acidic alpha keratose may be produced by a reciprocal of the foregoing technique: that is, by separating and retaining acidic alpha keratose from a mixture of acidic and basic alpha keratose, e.g., by ion exchange chromatography, and optionally the acidic alpha keratose has an average molecular weight of from 10 to 100 or 200 kiloDaltons. More preferably, the average molecular weight is from 30 or 40 to 90 or 100 kiloDaltons. Optionally, but in some embodiments preferably, the process further comprises the steps of re-dissolving said acidic alpha-keratose in a denaturing solution and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of basic alpha keratose, or less.

Basic and acidic fractions of other keratoses (e.g., KAP and gamma keratose) can be prepared in like manner as described above for basic and acidic alpha keratose.

Basic alpha kerateine is preferably produced by separating basic alpha kerateine from a mixture of acidic and basic alpha kerateine, e.g., by ion exchange chromatography, and optionally the basic alpha kerateine has an average molecular weight of from 10 to 100 or 200 kiloDaltons. More preferably, the average molecular weight is from 30 or 40 to 90 or 100 kiloDaltons. Optionally, but preferably, the process further includes the steps of re-dissolving said basic alpha-kerateine in a denaturing and/or buffering solution, optionally in the presence of a chelating agent to complex trace metals, and then re-precipitating the basic alpha kerateine from the denaturing solution. It will be appreciated by those of skill in the art that the composition preferably contains not more than 5, 2, 1, or 0.1 percent by weight of acidic alpha kerateine, or less.

The acidic alpha kerateine may be produced by a reciprocal of the foregoing technique; that is, by separating and retaining acidic alpha kerateine from a mixture of acidic and basic alpha kerateine, e.g., by ion exchange chromatography, and optionally the acidic alpha kerateine has an average molecular weight of from 5 or 10 to 100 or 200 kiloDaltons. Optionally, but preferably, the process further comprises the steps of re-dissolving said acidic alpha-kerateine in a denaturing and/or buffering solution), optionally in the presence of a chelating agent to complex trace metals, and then re-precipitating the basic alpha kerateine from the denaturing solution. It will be appreciated that the composition preferably contains not more than 5, 2, 1, or 0.1 percent by weight of basic alpha kerateine, or less.

Basic and acidic fractions of other kerateines (e.g., KAP and gamma kerateine) can be prepared in like manner as described above for basic and acidic alpha kerateine. Gamma keratins are typically precipitated in a non-solvent such as ethanol.

As used herein, "acidic" keratins are those keratins that are protonated at a predetermined pH such that they carry a net positive charge; "basic" keratins are those keratins that are de-protonated at a predetermined pH such that they carry a net negative charge. The Keratin Associated Proteins (KAP) as used herein carry a negative charge at the predetermined pH and bind to an anionic exchange resin, and thus in some embodiments is included in the basic keratin fractions taught herein. In some embodiments, the predetermined pH is between 5 and 7. In some embodiments, the pH is 6. For example, in some embodiments, keratose or kerateine is separated into acidic and basic fractions (e.g., by ion exchange chromatography) performed at a solution pH of 6, with the resulting acidic fraction including those keratins having a net positive charge at pH 6, and the basic fraction including those keratins having a net negative charge at pH 6. Likewise, for separation at a predetermined pH of 5.3, the acidic fraction will include those keratins having a net positive charge at pH 5.3 and the basic fraction will include those keratins having a net negative charge at pH 5.3.

Those skilled in the art will recognize that the predetermined pH is selected to effect the best separation between acidic and basic proteins based upon their isoelectric points (see, e.g., Table 1), though solubility at that pH should also be considered. When the pH of the solution is between the isoelectric point of these acidic and basic keratin fractions, basic keratin proteins will be de-protonated to have a net negative charge and bind to an anionic media (e.g., DEAE-Sepharose or Q-Sepharose (anion exchange)), while the acidic proteins will be protonated to have a net positive charge and pass through the column, thereby effecting separation.

Residual reductant and denaturing agents can be removed from solution by dialysis. Typical dialysis conditions are 1 to 2% solution of kerateines dialyzed against purified water. Those skilled in the art will recognize that other methods exist for the removal of low molecular weight contaminants in addition to dialysis (e.g. microfiltration, chromatography, and the like). The use of Trizma base is only required for initial solubilization of the kerateines. Once dissolved, the kerateines are stable in solution without the denaturing agent for finite periods. Therefore, the denaturing agent can be removed without the resultant precipitation of kerateines. Regardless of the fractionation/purification process, the resulting kerateines can be concentrated and lyophilized, similar to keratoses.

Meta kerateines. Kerateines have labile sulfur residues. During the creation of the kerateines, cystine is converted to cysteine, which can be a source of further chemical modifications. One such useful reaction is oxidative sulfur-sulfur coupling. This reaction simply converts the cysteine back to cystine and reforms the crosslinks between proteins. Crosslinking gamma or alpha kerateine fractions, or a combination of both, produces meta-kerateines. This is a useful reaction to increase the molecular weight of kerateines, which in turn will modify their bulk properties. Increasing molecular weight influences material properties such a viscosity, dry film strength, gel strength, etc. Additionally, water solubility can be modified through the production of meta kerateines. The high crosslink density of meta kerateines renders these biomaterials essentially insoluble in aqueous media, making them amenable to applications where preservation of material integrity in such media is preferred.

Meta keratins can be derived from the gamma or alpha fractions, or a combination of both. Oxidative re-crosslinking of the kerateines is affected by addition of an oxidizing agent such as peracetic acid or hydrogen peroxide to initiate oxidative coupling reactions of cysteine groups. A preferred oxidizing agent is oxygen. This reaction can be accomplished simply by bubbling oxygen through the kerateine solution or by otherwise exposing the sample to air. Optimizing the molecular weight through the use of meta keratins allows formulations to be optimized for a variety of properties including viscosity, film strength and elasticity, fiber strength, and hydrolytic susceptibility. Crosslinking in air works to improve biocompatibility by providing biomaterial with a minimum of foreign ingredients.

Basically, in some embodiments the kerateine is dissolved in a denaturing solution such as 7M urea, aqueous ammonium hydroxide solution, or 20 mM tris buffer solution. The progress of the reaction is monitored by an increase in molecular weight as measured using SDS-PAGE. Oxygen is continually bubbled through the reaction solution until a doubling or tripling of molecular weight is achieved. The pH of the denaturing solution can be adjusted to neutrality to avoid hydrolysis of the proteins by addition of mineral acid.

Optimizing the molecular weight through the use of meta-keratins allows formulations to be optimized for a variety of properties including viscosity, film strength and elasticity, fiber strength, and hydrolytic susceptibility. In some embodiments, crosslinking in air may improve biocompatibility by providing biomaterials with a minimum of foreign ingredients.

Keratin intermediate filaments. IFs of human hair fibers are obtained using the method of Thomas and coworkers (H. Thomas et al., Int. J, Biol. Macromol. 8, 258-64 (1986)). This is essentially a chemical etching method that reacts away the keratin matrix that serves to "glue" the IFs in place, thereby leaving the IFs behind. In a typical extraction process, swelling of the cuticle and sulfitolysis of matrix proteins is achieved using 0.2M $Na_2SO_3$, 0.1M $Na_2O_6S_4$ in 8M urea and 0.1M Tris-HCl buffer at pH 9. The extraction proceeds at room temperature for 24 hours. After concentrating, the dissolved matrix keratins and IFs are precipitated by addition of zinc acetate solution to a pH of approximately 6. The IFs are then separated from the matrix keratins by dialysis against 0.05M tetraborate solution. Increased purity is obtained by precipitating the dialyzed solution with zinc acetate, redissolving the IFs in sodium citrate, dialyzing against distilled water, and then freeze drying the sample.

Further discussion of keratin preparations are found in U.S. Patent Application Publication 2009/0004242 (Van Dyke), which is incorporated by reference herein.

The keratose and kerateine sub-fractions of keratin, in particular, have demonstrated interesting characteristics such as improved gelation, viscosity and hydrolytic stability, as well as an ability to bind therapeutic agents such as antibiotic drugs and growth factors. Using the different fractions of keratins as described above, either alone or in combination, the compound binding and material properties of the keratin biomaterials can be controlled. Unique features of some embodiments of this system include:

An ability to re-combine keratin fractions into keratin biomaterials that have controllable properties;

An ability to bind therapeutic agents to the keratin such that they are not appreciably released except upon degradation of the keratin; and An ability to control the degradation of the keratin by crosslinking and other means, primarily because there are no keratinases in mammals so keratin biomaterials degrade primarily through a hydrolytic mechanism.

In some embodiments, drug release can be controlled by taking into account the degradation rate of the keratin biomaterial as taught herein. In some embodiments, release may also be influenced by how strongly a compound binds to the keratin composition, which can be determined using techniques known in the art. In general, sub-types with high net negative charge strongly bind positively-charged drugs (e.g., quaternary ammonium salts). Keratins with the highest net negative charge at physiological pH are those with sulfonic acid residues (i.e. keratoses). Within the keratoses, those with the most sulfonic acid are expected to bind the strongest (i.e., ultra high sulfur KAP and gamma). However, all keratins have relatively high sulfur content, so all are expected to bind positively charged drugs to some degree. Within the kerateines, these compounds can also acquire a net negative charge at physiological pH because they have an isoelectric point below pH 7.4 (i.e. around pH 4.6). Kerateines may be particularly useful for binding growth factors and other protein-based therapeutics, especially when the compound of interest has an isoelectric point above pH 7.4. Recombinant human BMP-2, for example, has an isoelectric point of 9 (see Geiger M, Li R H, Friess W. Collagen sponges for bone regeneration with rhBMP-2. Adv Drug Deliv Rev 2003; 55(12):1613-29). At physiologic pH, the kerateine carries a net negative charge and the rhBMP-2 a net positive charge, thereby facilitation binding. Bioavailability is influenced by these binding energies to some degree, but release from the keratin biomaterial construct is dictated by the overall stability of the keratin network.

As taught herein, drug release from keratin biomaterials is dependent on the degradation rate. It then follows that parameters and characteristics of the hydrogel that control degradation rate will thereby control drug release. That is, characteristics that decrease degradation rate will decrease drug release rate and prolong release. In the keratin system, parameters that can decrease degradation rate include increased total protein content, increased crosslink density, and increased resistance to hydrolysis. Since binding between keratin and the compound of interest is an intrinsic property of the two materials, degradation rate is the more flexible characteristic of the system as the parameters stated above can be more easily manipulated. For example, a compound with high binding affinity for keratose can be released over long time periods by decreasing the degradation rate of the keratose by introducing exogenous cross-linking using techniques known in the art (e.g. chemical crosslinking using glutaraldehyde or EDC; UV crosslinking using the method of Sando et al. [see Sando L, Kim M, Colgrave M L, Ramshaw J A, Werkmeister J A, Elvin C M. Photochemical crosslinking of soluble wool keratins produces a mechanically stable biomaterial that supports cell adhesion and proliferation. J Biomed Mater Res A 2010; 95(3):901-11]. Conversely, a compound that has high binding affinity for kerateine can be released over shorter time periods by decreasing crosslinking density using thiol capping techniques known in the art (see Schrooyen P M, Dijkstra P J, Oberthiir R C, Bantjes A, Feijen J. Partially carboxymethylated feather keratins 2: Thermal and mechanical properties of films. J Agric Food Chem 2001; 49(1):221-30).

Increasing resistance to hydrolysis can be achieved by the choice of keratin derivative. Since keratoses are more hygroscopic, and contain a sulfonic acid residue that occupies a position that is one carbon atom removed from the main polypeptide chain, the amide bond can become polarized and thus more susceptible to hydrolytic attack. If high hydrolytic resistance is desired, a kerateine biomaterial is a better choice as its degradation rate will be slower. This is exemplified by the fact that a crude keratose (i.e., alpha+ KAP+gamma) implant typically degrades in vivo over the course of 8 weeks, while a crude kerateine implant typically degrades in vivo over the course of 6 months (see Hill et al. Some properties of keratin biomaterials: Kerateines. Biomaterials 2010:31(4) :585-93).

In some embodiments, additional control over the degradation rate of keratin biomaterials (and consequently, drug release) can be obtained by controlling the protein composition. Manipulating the relative amounts of alpha, KAP, and gamma can alter the stability of the hydrogels and hence their susceptibility to hydrolysis. Another example of this level of control is evident in the purification of crude keratose. Crude keratose contains alpha keratin proteins, KAP, and gamma proteins. The KAP and gamma proteins are low molecular weight, globular in nature, and do not contribute appreciably to mechanical properties. Moreover, as gamma content in this system increases, hydrolytic stability typically decreases. This suggests that viscoelastic properties can be improved by removing KAP and gamma proteins (i.e. purifying the alpha keratins) and can be demonstrated in the keratose system through various stages of alpha purification.

In particular, the manipulation of the percentage of the components of a keratose or kerateine hydrogel may affect properties such as viscosity, film strength and elasticity, fiber strength, and hydrolytic susceptibility. The higher the percentage of alpha keratose or alpha kerateine in the composition leads to decreased hydrolytic susceptibility. Conversely, lowering the percentage of alpha keratose or alpha kerateine in the composition leads to increased hydrolytic susceptibility. Further, hydrolysis of a hydrogel may be measured to determine the effective compound of interest release window.

In some embodiments, the keratose or kerateine compositions of the invention comprise alpha keratose or alpha kerateine, gamma keratose or gamma kerateine, or a mixture thereof.

Thus, in some embodiments, compositions of the invention comprise about 40%, about 50%, about 60%, about 70%, about 80%, about 90%, or about 100% by weight alpha keratose or alpha keratiene. In yet other embodiments, compositions of the invention comprise about or equal to 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94, 95%, 96%, 97%, 98%, 99%, or 100% by weight alpha keratose or alpha kerateine. In yet other embodiments, compositions of the invention comprise about 50% to about 60%, about 60% to about 70%, about 70% to about 80%, about 80% to about 90%, about 90% to about 100% by weight alpha keratose or alpha kerateine.

In other embodiments, compositions of the invention comprise about 60%, about 50%, about 40%, about 30%, about 20%, about 10%, or about 0% by weight gamma keratose or gamma kerateine.

In specific embodiments, compositions of the invention comprise about 50% alpha-keratose and about 50% gamma-keratose, about 60% alpha-keratose and about 40% gamma-keratose, about 70% alpha-keratose and about 30% gamma-keratose, about 80% alpha-keratose and about 20% gamma-keratose, about 90% alpha-keratose and about 10% gamma-keratose, or about 100% alpha-keratose and about 0% by weight gamma-keratose.

In specific embodiments, compositions of the invention comprise about 50% alpha-kerateine and about 50% gamma-kerateine, about 60% alpha-kerateine and about 40% gamma-kerateine, about 70% alpha-kerateine and about 30% gamma-kerateine, about 80% alpha-kerateine and about 20% gamma-kerateine, about 90% alpha-kerateine and about 10% gamma-kerateine, or about 100% alpha-kerateine and about 0% by weight gamma-kerateine.

Exemplary Keratin Preparations for Extended Delivery of Therapeutic Agents.

7-day release: Approximately 20-30% gamma keratose+70-80% alpha+KAP keratose (20% total protein in saline).

10-day release: Approximately 10-20% gamma keratose+80-90% alpha+KAP keratose (20% total protein in saline).

30-day release: Approximately 0-10% gamma keratose+90-100% alpha+KAP keratose (20% total protein in saline).

60-day release: Approximately 100% acidic alpha keratose (20% total protein in saline)

180-day release: Approximately 10-20% gamma kerateine+80-90% alpha+KAP kerateine (20% total protein in saline).

>180-day release: Approximately 100% acidic alpha kerateine (20% total protein in saline).

Formulations. Dry powders may be formed of keratin preparations described above in accordance with known techniques such as freeze drying (lyophilization). In some embodiments, hydrogel compositions of the invention may be produced by mixing such a dry powder composition form with an aqueous solution to produce a composition having an electrolyte solution with a keratin solubilized therein. The mixing step can be carried out at any suitable temperature, typically room temperature, and can be carried out by any suitable technique such as stirring, shaking, agitation, etc. The salts and other constituent ingredients of the electrolyte solution (e.g., all ingredients except the keratin derivative and the water) may be contained entirely in the dry powder, entirely within the aqueous composition, or may be distributed between the dry powder and the aqueous composition. For example, in some embodiments, at least a portion of the constituents of the electrolyte solution is contained in the dry powder.

In some embodiments, the compositions are sterile. In some embodiments, keratin solutions are sterile filtered and processed aseptically, or terminally sterilized using ethylene oxide, e-beam, gamma, or other low temperature method (i.e. <50° C.).

The keratin composition may be provided preformed and aseptically packaged in a suitable container, such as a flexible polymeric bag or bottle, or a foil container, or may be provided as a kit of sterile dry powder in one container and sterile aqueous solution in a separate container for mixing just prior to use. When provided pre-formed and packaged in a sterile container the composition preferably has a shelf life of at least 4 or 6 months (up to 2 or 3 years or more) at room temperature, prior to substantial loss of viscosity (e.g., more than 10 or 20 percent) and/or structural integrity of the keratin gel or hydrogel.

The composition may be provided in a precursor solution aseptically packaged in a suitable container. For example, a gel precursor solution can be provided in a glass ampule ready to use directly or after dilution by the user. In the case of kerateine compositions, which can re-crosslink in the presence of oxygen in air, a sterile precursor solution in a sealed ampule under an inert atmosphere (e.g. nitrogen) can be provided. A user would simply break open the ampule, mix in a compound of interest and use the solution directly or after dilution for producing the gel containing the compounds of interest dispersed therein.

In some embodiments, keratin biomaterial compositions including compounds of interest can be formulated for an injection or as a surface treatment (e.g., for skin wounds). Formulations of the invention include those for parenteral administration (e.g., subcutaneous, intramuscular, intradermal, intravenous, intra-arterial, intraperitoneal injection) or implantation. In one embodiment, administration is carried out intravascularly, either by simple injection, or by injection through a catheter positioned in a suitable blood vessel, such as a renal artery.

In some embodiments, compounds of interest are administered in a therapeutically effective amount. The therapeutically effective dosage can be determined in accordance with procedures known to those skilled in the art.

In some embodiments, the invention provides for the release of a compound of interest that is active. The bioactivity of the released compound of interest can be measured in a number of assays, both in vitro or in vivo. Such assays are well known in the art. In some embodiments, the invention provides for the release of a compound of interest wherein the activity of the compound of interest is unchanged due to being complexed with the hydrogels described herein. In other embodiments, the activity of the compound of interest retains greater than 50%, 60%, 70%, 80%, 90%, 95%, 99% or more activity as compared to the compound of interest not complexed in a hydrogel.

Kits are also provided, where the compositions described herein are provided in a suitable container (e.g. a plastic or glass bottle, sterile ampule, etc.), optionally packaged in sterile form. The compositions may be provided as a powder, or in an aqueous liquid, and may be provided in different volumes.

Embodiments of the present invention are further detailed in the following non-limiting examples.

EXAMPLES

Example 1

Release of antibiotic (ciprofloxacin) from keratose gel. Keratose gels consisting of both alpha/KAP and gamma fractions were used to assess rate of antibiotic release. Release profiles of drug mimic the keratose gel degradation profile (FIG. 1). Although there is some simple diffusion in early time points, protein release correlates with the degradation of the keratose gel.

Example 2

Figure 2:
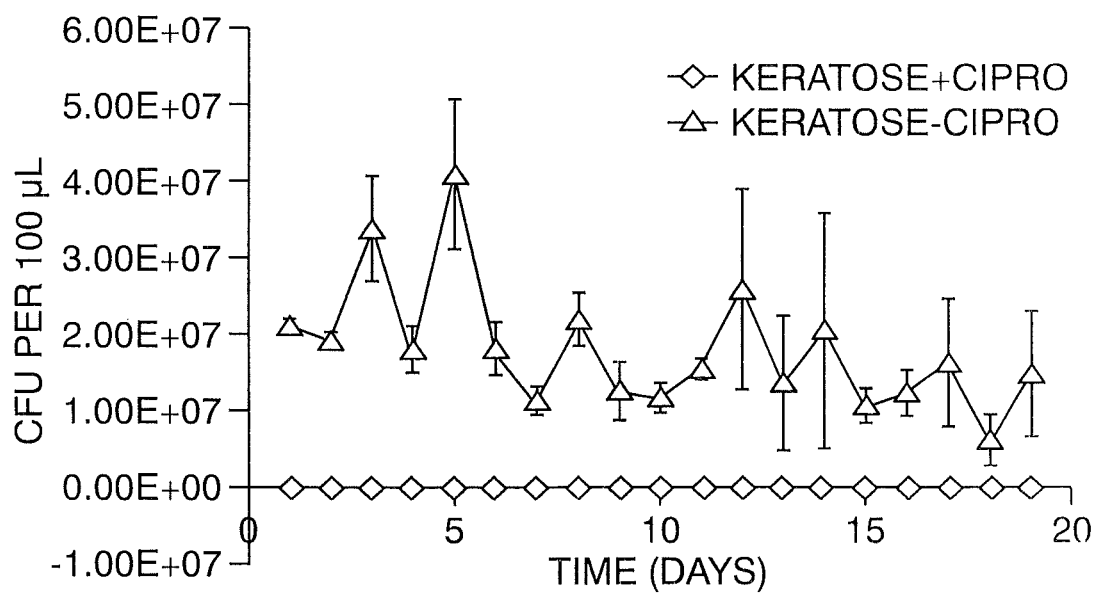
FIG. 2. Inhibition of bacteria (*Staphylococcus aureus* strain 29213) with ciprofloxacin in keratose hydrogels. Keratose gels loaded with antibiotic (Keratose+Cipro) inhibited bacterial growth through 19 days compared to unloaded controls (Keratose−Cipro).

Inhibition of bacteria (Staphylococcus aureus strain 29213) with ciprofloxacin in keratose hydrogels. The bioactivity of ciprofloxacin released from keratose gels was assessed by a broth inhibition assay. $10^5$ colony forming units/mL (cfu/mL) in broth were added to keratose gels with or without antibiotic (ciprofloxacin) daily. The number of colonies present in the broth were determined 24 hours later by plating on sheep blood agar plates. Keratose gels loaded with antibiotic (Keratose+Cipro) inhibited bacterial growth through 19 days compared to unloaded controls (Keratose−Cipro) (FIG. 2). These data demonstrate that antibiotic released from keratose gels remains bioactive through its ability to inhibit bacterial growth.

Example 3

Figure 3:
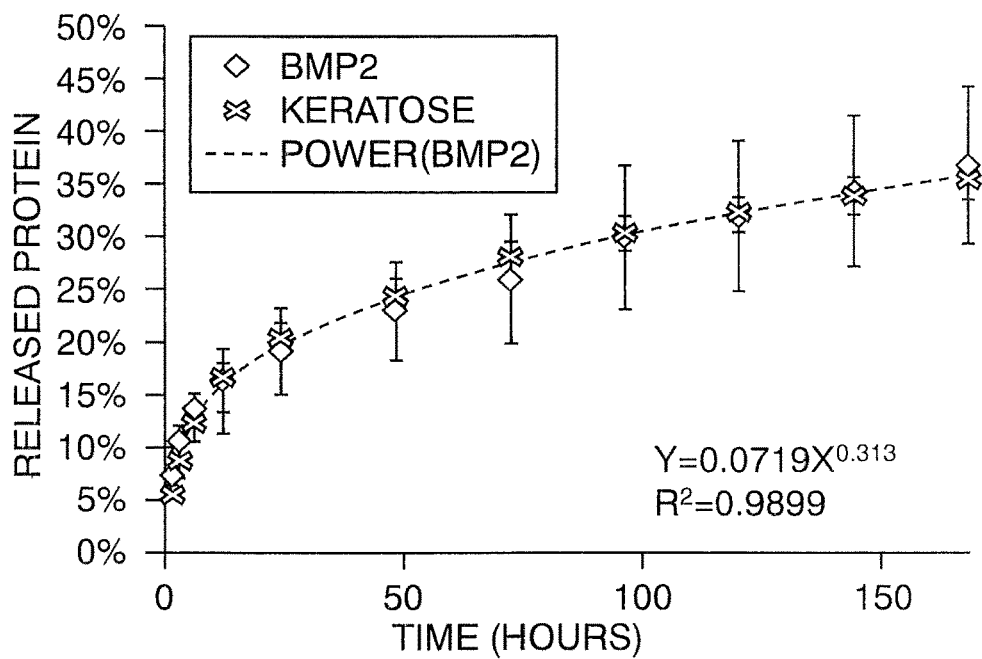
FIG. 3. Release of growth factor (bone morphogenetic protein 2; BMP-2) from keratose gel.
Figure 4A:
FIG. 4. Bioactivity of released growth factor from keratin biomaterials. A) BMP2 was loaded into 20% w/v keratin gels and scaffold and implanted in a critical-size rat femur defect model using an internal fixator stabilizer as described by Oest et al. (Journal of Orthopedic Research, 25(7): 941-950, 2007. B) Keratose gel alone did not induce bone regeneration. B) Minute dose of BMP2 (2 μg) produced a small amount of new bone formation, while a C) normal dose of BMP2 (200 μg) in keratose gel enabled the complete bridging of the bone stumps.
Figure 4B:
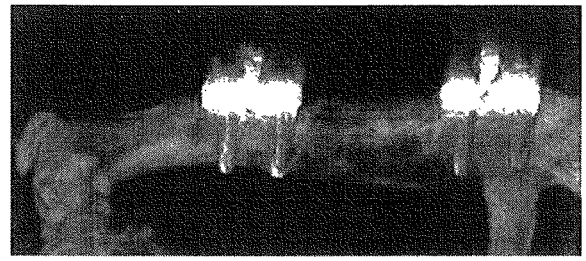
Figure 4C:

Release of growth factor (bone morphogenetic protein 2; BMP-2) from keratose gel. Keratose gels consisting of both alpha/KAP and gamma fractions were used to assess rate of growth factor release. Release profiles of BMP-2 correlate strongly with the keratose gel degradation profile, demonstrating that hydrolysis of the gel determines the release rate of the growth factor (FIG. 3).

Example 4

Bioactivity of released growth factor from keratin biomaterials. BMP2 was loaded into 20% w/v keratin gels and scaffold and implanted in a critical-size rat femur defect model using an internal fixator stabilizer as described by Oest et al. (Journal of Orthopedic Research, 25(7): 941-950, 2007. B) Keratose gel alone did not induce bone regeneration. A minute dose of BMP2 (2 µg) produced a small amount of new bone formation, while a normal dose of BMP2 (200 µg) in keratose gel enabled the complete bridging of the bone stumps. The scaffold form of BMP2-loaded keratose also produced significant bone formation. Additionally, the reduced extract of keratin, kerateine, that was carrying a smaller level of BMP2 (20 µg) regenerated new bone tissue similar to keratose with 200 µg BMP2 preparation. These results demonstrate the ability of keratin gels (keratose and kerateine) to maintain the bioactivity and achieve healing of a load-bearing bone defect.

Example 5

Sustained Release of Bioactive Ciprofloxacin from Keratin Hydrogel

Keratin was extracted from Chinese human hair obtained from a commercial vendor (World Response Group). Ciprofloxacin-HCl used for release and bioactivity experiments was obtained from Sigma (Fluka, St. Louis, Mo.). Ultrapure agarose for control hydrogels was obtained from Invitrogen (Gibco BRL, Carlsbad, Calif.). Keratin protein concentrations in release experiments were determined by Lowry protein assay with the DC Protein assay (Bio-Rad, Hercules, Calif.). Size exclusion chromatography was performed with Sephadex G-25 resin (Sigma-Aldrich, St. Louis, Mo.). For microbiology, Columbia agar with 5% sheep blood plates and Mueller-Hinton broth were obtained from BD Biosciences (Bedford, Mass.) and PBS was from Thermo Scientific (HyClone, Rockford, Ill.). Staphylococcus aureus (S. aureus) strain 29213 was obtained from American Type Culture Collection (Manassas, Va.).

Keratin was extracted from end-cut human hair fibers by an oxidative method previously described (Sierpinski et al., Biomaterials 2008; 29(1):118-28). Briefly, a 20-fold excess of peracetic acid was added to clean, dry hair cut into short pieces. Oxidation was allowed to proceed for 12 hours at 37° C. with gentle shaking. The solution was then passed through a 500 µm sieve and the hair was collected and washed extensively with deionized water before extraction with 100 mM Tris base (40-fold excess volume to starting hair weight) for two hours at 37° C. The solution of extracted keratins was then collected by passing over a sieve. A second extraction with deionized water was performed at 37° C. for two hours to increase the yield of extracted keratin. The collected keratins were then dialyzed extensively against deionized water to pH<7 and negligible ionic strength. After dialysis, the keratin proteins were frozen in liquid nitrogen bath (while in glass containers), lyophilized, aliquoted into sterile plastic vials, gamma irradiated at 800 kRad in a JL Shepherd 484 self-shield irradiator, and stored at −80° C. until use.

For these studies, keratose was obtained through an oxidative extraction from end-cut human hair fibers. Through this extraction process, cystine residues are converted to unreactive sulfonic acid as disulfide crosslinks are oxidized. Therefore, these hydrogels are not covalently crosslinked. The keratins extracted by this technique contain high molecular weight (~40-60 kDa), low-sulfur content alpha keratins; low molecular weight (~10-15 kDa) high-sulfur content gamma keratins; and high sulfur content keratin associated proteins (KAP). KAP are of similar molecular weight to the gamma fraction. In these studies, keratoses were not further purified to remove any components such as KAP or peptides produced by the hydrolysis side-reaction.

These extracted proteins have been subjected to several characterizations including sodium dodecyl sulfate-polyacrylamide gel electrophoresis (SDS-PAGE) followed by mass spectroscopy and found that the resulting extracts contain keratin 81, 31, and 33a proteins (data not shown). The proteins are found on SDS-PAGE as monomers (molecular weight ~40-60 kDa), obligate heterodimers (K31/K81 or K33a/K81; Mw ~110 kDa) as well as higher order multimers that cannot be reduced by SDS. In addition, lower molecular weight gamma keratins and keratin associated proteins that appear on SDS-PAGE at molecular weight ~14 kDa were found.

20% (weight per volume, w/v) hydrogels were formed by adding phosphate-buffered saline (PBS) with or without ciprofloxacin-HCl (ciprofloxacin) at pH 5.2 to dry powder of keratin proteins followed by agitation (150 RPM on laboratory shaker) and warming overnight at 37° C. Ciprofloxacin was dissolved in 0.1M HCl in PBS and the pH is corrected to 5.2 prior to hydrogel formation in order to prevent precipitation of keratin proteins at very low pH that would be expected due to the acidity of 0.1M HCl in water.

Lyophilized keratin powder is subjected to 800 kRad gamma irradiation to prevent contamination with environmental bacteria and fungus. In a typical hydrogel preparation, PBS or water at or near neutral pH is added to the keratin powder. The sample is then mixed and allowed to gel overnight. However, for these studies in which ciprofloxacin release was studied, the aqueous buffer used to form the keratin hydrogels required a modification to a pH of 5.2 to keep ciprofloxacin in solution. Because keratins are known to undergo isoelectric precipitation near this pH, we characterized the resulting hydrogels to ensure (1) that keratin precipitation had not occurred and (2) that ciprofloxacin had not precipitated within the keratin hydrogels. All lyophilized hydrogels showed similar pore structures, indicating that the keratin has not precipitated. This matches our observation of the gelation process in which no precipitates were observed to form at the macroscopic level. There were no particulate aggregates that would be indicative of ciprofloxacin precipitation. These results indicate that ciprofloxacin was successfully and stably loaded into the keratin hydrogels.

The architecture of the resulting hydrogels was characterized by scanning electron microscopy (SEM). In brief, keratin hydrogels were formed as above and then lyophilized (Labconco Shell Freeze System, Kansas City, Mo.). The samples were sputter coated in gold-palladium with a Cold Cathode Sputter Coater (Desk-1 Model, Denton Vacuum, Moorestown, N.J.) and imaged on a Hitachi 2600N environmental SEM (Hitachi High Technologies, Pleasanton, Calif.) at 25 kV and working distance of approximately 10 mm.

Hydrogels with or without ciprofloxacin were formed as described above at a volume of 350 µL. 500 µL of PBS was placed on top of the hydrogel and the samples incubated at 37° C. At specified times (1, 2, 4, 6, 12, 24 hours then daily through 21 days), the PBS was removed and replaced with fresh PBS. The concentration of ciprofloxacin in the collected samples was determined fluorescently at 340 nm/450 nm excitation/emission on a SpectraMax M5 plate reader (Sunnyvale, Calif.) through the inherent fluorescence properties of ciprofloxacin with comparison to a standard curve.

In some experiments, samples were incubated with 1M NaCl or 8M urea and released ciprofloxacin was collected at 24 hours for fluorescence analysis as above. These experiments were conducted to determine whether interaction between ciprofloxacin and keratin was based on electrostatic or hydrophobic interactions.

Samples used for fluorescence measurements of ciprofloxacin were also analyzed for keratin protein concentration corresponding to the hydrolytic degradation and/or chain untangling of the hydrogels with time. The Bio-Rad DC Protein Assay was used as recommended by the manufacturer and comparison to a standard curve of keratin. Absorbance of the samples was read at 750 nm on the SpectraMax MS plate reader.

For size exclusion chromatography experiments, 350 µL keratin hydrogel samples were prepared either with or without ciprofloxacin as described above. Samples were incubated with PBS for 24 hours, at which time the PBS was removed. The collected PBS, containing ciprofloxacin and keratin, was then passed through a Sephadex G-25 column (1 cm column inner diameter, 28 cm bed height) pre-equilibrated with PBS. PBS was used for the liquid phase of the column. 1 mL fractions were collected in a Bio-Rad Fraction collector. Ciprofloxacin elution was determined by fluorescence (340 nm/450 nm excitation/emission) and keratin elution was determined by DC Protein Assay (750 nm absorbance) as described above. Ciprofloxacin only (not incorporated into hydrogel) and keratin (not formed into hydrogel) were run as standards to calibrate the column for elution peaks of these components.

In order to determine the rate and nature of ciprofloxacin release from keratin gels, we conducted release studies and subjected collected samples to several quantitative outcomes. In particular, we investigated ciprofloxacin release as well as the amount of keratin found in these collected samples. Data presented are results of single representative experiments run in triplicate (n=3) except where noted in figures and results.

Figure 5A:
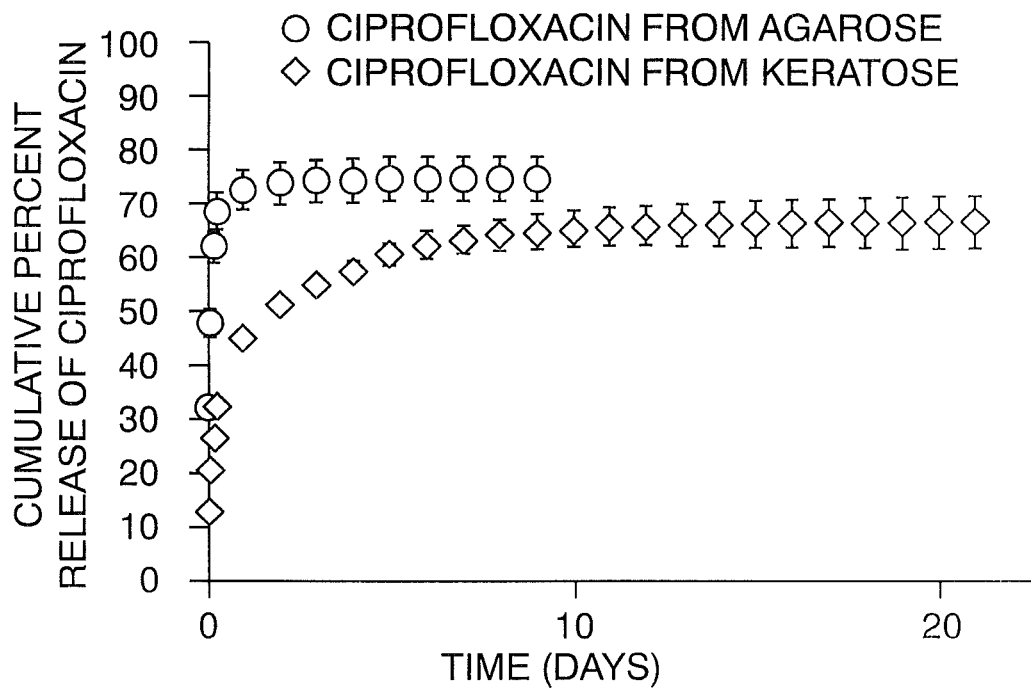
FIG. 5. Ciprofloxacin release from keratin hydrogels. (A) Percentage of total loaded ciprofloxacin released over the course of time from keratin hydrogels. An agarose hydrogel (diffusion-mediated) control is shown for reference. Inset shows release over the first 24 hours. (B) Percentage of total release of ciprofloxacin from keratin hydrogels (same data as (A)) compared to the percentage of total keratin released from the keratin hydrogels. Correlation between keratin release and ciprofloxacin released is greater than 0.99. n=3 for each data point (single reading taken from different samples). Error bars indicate standard deviation.

FIG. 5 shows the release profile of ciprofloxacin from keratin hydrogels at a loading level sufficient to achieve the desired effects of bacterial inhibition, but below levels toxic to most mammalian cells (see below for in vitro and in vivo bioactivity assays). As shown in FIG. 5, 40% of the ciprofloxacin is released over the course of the first 24 hours. Interestingly, nearly zero-order release from 1-6 days was observed. A control of agarose gel was run (FIG. 5A) loaded with ciprofloxacin to show an example of a diffusion-mediated release profile. Ciprofloxacin release from agarose hydrogel was much more rapid than release from keratin hydrogels. Attempts to use a collagen hydrogel led to rapid dissolution of the gel and were unsuccessful.

Figure 5B:
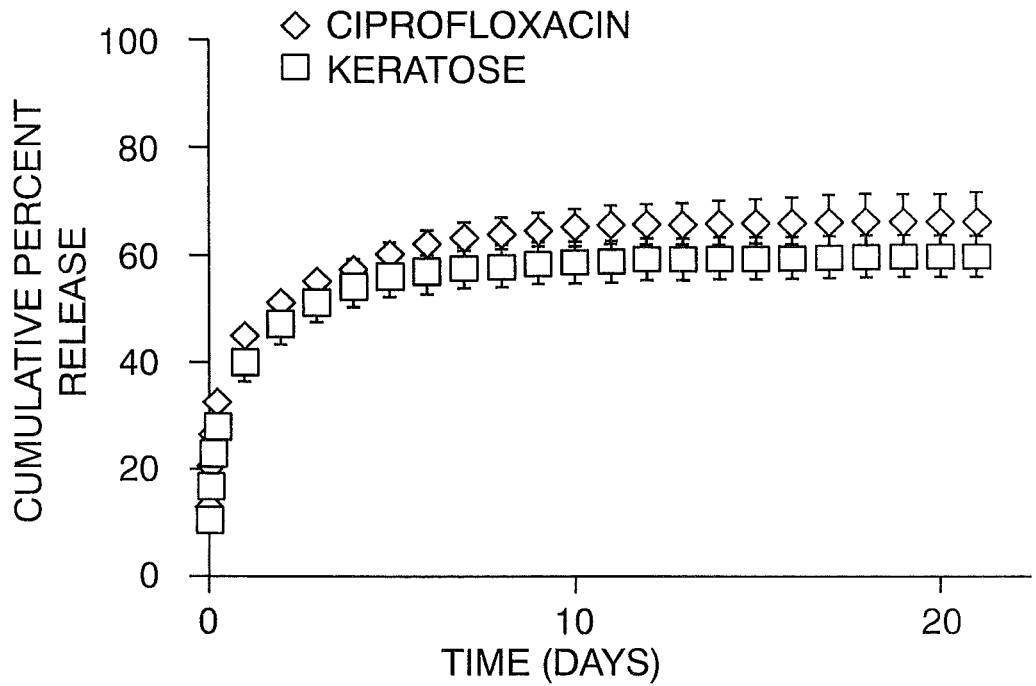

The keratin hydrogels degraded over the course of the experiments. Therefore, the amount of keratin protein that released with the ciprofloxacin was assayed. FIG. 5B shows that the keratin degradation overlaps nearly completely with ciprofloxacin release (correlation=0.99), thus indicating that ciprofloxacin is not released in a diffusion-mediated fashion, but that it is released through a mechanism consistent with the degradation of the keratin hydrogel matrix.

Figure 6:
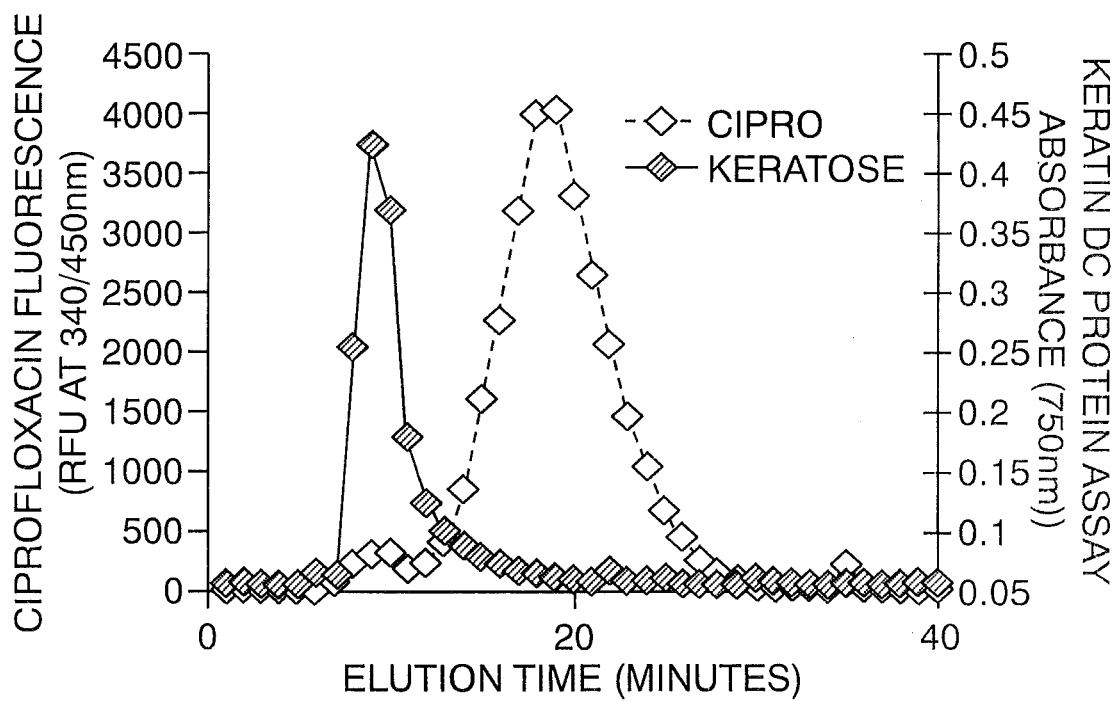
FIG. 6. The material eluting from keratin hydrogels consists of both keratin and ciprofloxacin. To determine if the ciprofloxacin was binding to keratin in the released samples, we subjected the samples to size exclusion chromatography. Distinct peaks were detected for keratin (by protein assay absorbance reading, right axis) and ciprofloxacin (by fluorescence, left axis). The peaks are consistent with standard of keratin only or ciprofloxacin only (not shown). Traces are for a single representative experiment.

To investigate whether the released ciprofloxacin was associated with the keratin proteins following release from the hydrogel, samples from ciprofloxacin and keratin release experiments were subjected to size exclusion chromatography because release studies demonstrated that both of these components were being released from the hydrogel. FIG. 6 shows the traces of samples collected from the ciprofloxacin release experiments after passage over a Sephadex column. There is clear peak-to-peak resolution for keratin and ciprofloxacin that is consistent with elution profiles of keratin or ciprofloxacin standard run alone (data not shown). These data show that none of the detectable ciprofloxacin co-eluted with the keratin, suggesting that keratin and ciprofloxacin are not strongly associated after release from the hydrogel. It should be noted that the slight area of increased fluorescence on the ciprofloxacin trace is due to autofluorescence of the keratin and not with any co-elution of ciprofloxacin.

Figure 7:
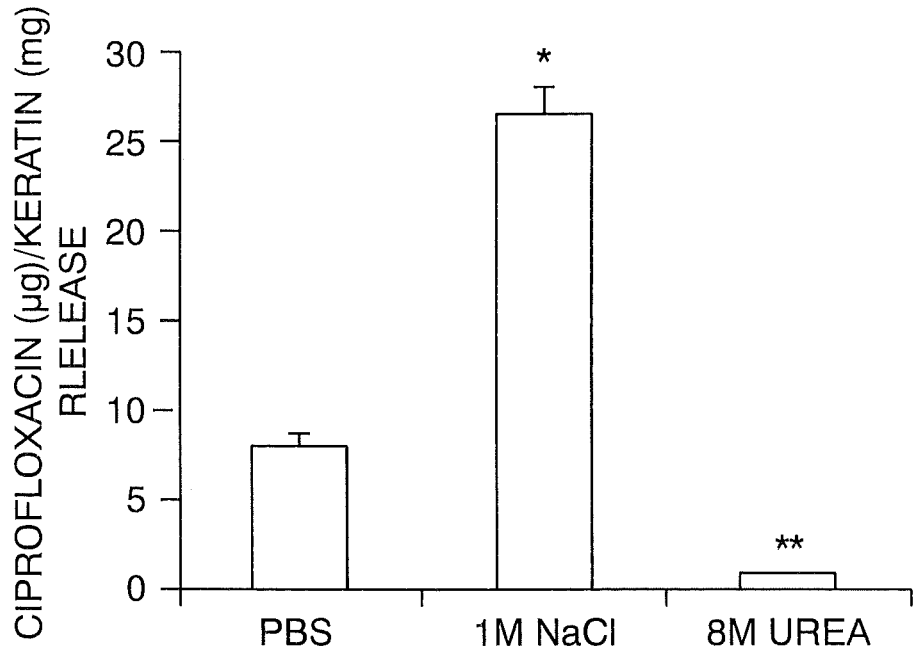
FIG. 7. Nature of ciprofloxacin-keratin interactions in the gel state. The amount of ciprofloxacin released from keratin hydrogels at 24 hours was determined by fluorescence and normalized to the amount of keratin release for each condition. Gels were incubated in PBS, 1M NaCl or 8M urea. * Indicates release significantly greater than in PBS ($p<0.01$) and ** indicates release significantly less than in PBS ($p<0.01$). Error bars indicate standard deviation from three separate samples.

To investigate if other interactions contribute to the release profile of ciprofloxacin from keratin hydrogels, the relative contributions of electrostatic and hydrophobic interactions in the gel state were studied. To disrupt electrostatic interactions, ciprofloxacin-loaded hydrogels were incubated with 1M NaCl, and to disrupt hydrophobic interactions, keratin-loaded hydrogels were incubated with 8M urea. As shown in FIG. 7, the application of 1M NaCl led to a significant increase (p<0.01) in release compared to PBS, suggesting that electrostatic interactions play a role in the binding of ciprofloxacin to keratin. In contrast, the release of ciprofloxacin in 8M urea was significantly less (p<0.01) than in PBS, indicating that hydrophobic interactions do not dictate the release. Due to differences in the rate of keratin release in these studies, data were normalized to the amount of keratin protein release measured by the DC protein assay.

Bioactivity of released ciprofloxacin by broth inhibition assay. A broth inhibition assay was used to determine the biological activity of released ciprofloxacin and determine the time course over which ciprofloxacin released from keratin hydrogels could suppress bacterial growth. This is a robust assay due to a daily reinoculation and is better suited to the hydrogel nature of this material than zone of inhibition assays. An agarose hydrogel control was used in these studies as an indicator of the inhibition that would be achieved by a material that did not degrade (over the course of the experiment), but released ciprofloxacin via a diffusion-mediated mechanism.

Keratin hydrogels with or without ciprofloxacin were formed as described above, but with a 1 mL total volume. S. aureus 29213 was streaked onto a sheep blood agar plate and grown overnight. One colony was selected and diluted to a concentration of $10^5$ colony forming units (cfu) per mL in Mueller-Hinton broth as determined by McFarland standard. A colony count plate was made for each day's experiment in order to normalize minor variability in the number of bacterial colonies. 10 mL of this $10^5$ cfu/mL suspension was added to each gel. Gels were then incubated for 22-24 hours at 37° C. in the broth medium containing $10^5$ cfu. After incubation, broth samples from the gel were serially diluted at 1:10 ratios. These dilutions were then streaked onto sheep blood agar plates and incubated overnight at 37° C. The next day, the number of colony forming units was determined by counting each plate. This process was repeated for each day of the experiment, with 10 mL of fresh broth containing $10^5$ cfu/mL of S. aureus 29213 added daily.

Figure 8:
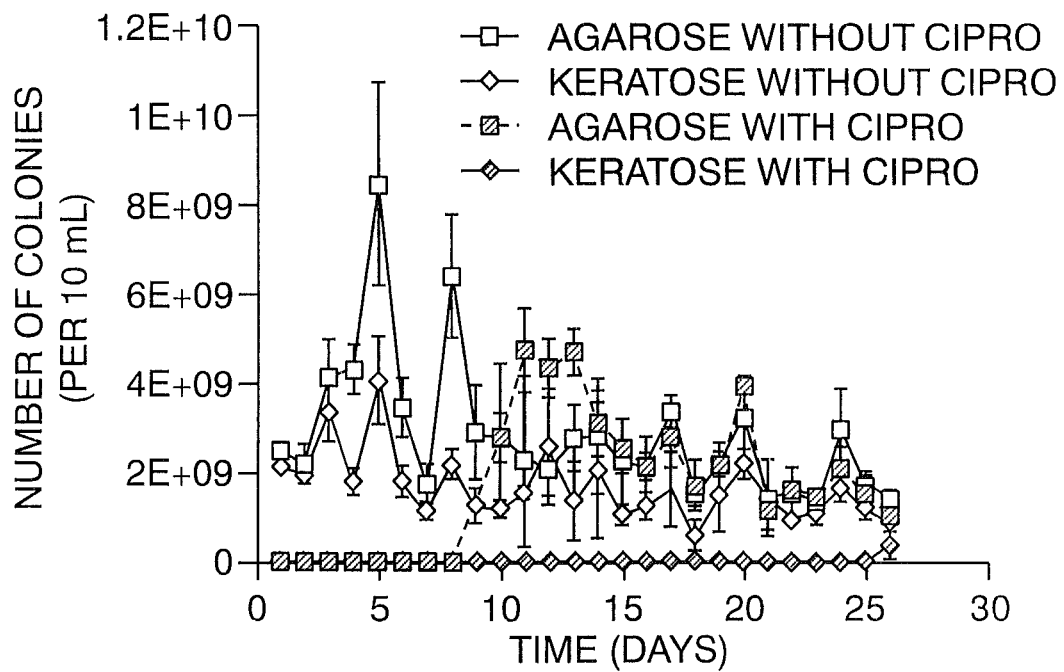
FIG. 8. In vitro bioactivity. Number of colonies in 10 mL of broth after overnight incubation as determined by bacterial plate counts. Error bars denote standard deviation and data points are the average of 3 separate cultures from a representative experiment. Release of ciprofloxacin from keratin hydrogels inhibited bacterial growth for 23 days. This was statistically significant compared to agarose and keratin gels not loaded with ciprofloxacin at all time points and relative to agarose loaded with ciprofloxacin at times beyond 8 days ($p<0.05$). Data points are from three separate samples and error bars denote standard deviation.

As shown in FIG. 8, the release of ciprofloxacin from keratin hydrogels was sufficient to achieve inhibition of bacterial growth over the course of 23 days. This inhibition was clearly prolonged compared to the inhibition through release from agarose (8 days). The levels of bacterial growth in ciprofloxacin-loaded keratin hydrogels was significantly less ($p<0.05$) than keratin and agarose hydrogels without ciprofloxacin at all time points and significantly less than agarose hydrogels with ciprofloxacin at all time points greater than 9 days.

Bioactivity of released ciprofloxacin in mouse model. A subcutaneous mouse model was used with 4-week-old C57/BL6J mice in order to determine if the effects observed in vitro could be translated in vivo. A high bacterial load was placed at the site of implantation ($10^8$ cfu of S. aureus). Keratin without ciprofloxacin did not clear the infection indicating minimal anti-bacterial properties of the keratin. However, keratin with ciprofloxacin release significantly reduced the bacterial load at both 1 and 2 weeks, completely clearing the infection by 2 weeks. Later time points were not possible with this model as the mice spontaneously cleared the infection at 3 weeks and later.

Keratin proteins extracted by the oxidative extraction technique used for these studies do not contain disulfide linkages because they are broken and converted to sulfonic acid. Therefore, the hydrogels are likely held together through hydrophobic interactions and chain entanglement but not through covalent disulfide cross-linking. These keratose proteins spontaneously form hydrogels at approximately 15% weight/volume and 20% (weight per volume) hydrogels were used in these studies.

The ciprofloxacin used in these studies is an antibiotic indicated in some cases for bone, joint, and soft tissue infections. It is not typically a first-line treatment because it is a broadly active agent. However, ciprofloxacin is inherently fluorescent, allowing us to track its release without modification of the antibiotic molecule by fluorescent compounds that could alter its physiochemical properties and without the use of radiolabels. Inherent fluorescence of keratin was subtracted for all release studies, but the fluorescence of ciprofloxacin typically gave signal to noise ratios of 5-30 times that of the keratin autofluorescence.

The use of ciprofloxacin required a slight modification to the fabrication of keratin hydrogels by lowering the pH to 5.2. To ensure that keratin proteins or ciprofloxacin did not precipitate under the gelation conditions, we imaged the scaffolds by SEM. It was noted that the pore architectures of all scaffolds were nearly identical, with pores of approximately 50 μm after lyophilization. The processing conditions for SEM imaging would allow precipitates of either the keratin or ciprofloxacin to be observed, but no precipitates were found on any of the scaffolds imaged, indicating the ability to effectively load keratin gels.

The release characteristics of ciprofloxacin from the keratin hydrogels were particularly interesting. A comparison of the rate of ciprofloxacin release to keratin release indicated an overlap of the release profiles and a very high correlation (0.99). Although approximately 40% of the loaded ciprofloxacin was released in the first 24 hours, there was not a rapid burst release in the first several hours (see FIG. 5A insert). It was noted from SDS-PAGE that protein released from the hydrogels during the ciprofloxacin release experiment contained some enrichment of the low molecular weight gamma keratins at early time points (data not shown). It is therefore possible that ciprofloxacin is released through interaction with gamma keratins, but it is also possible that ciprofloxacin and gamma keratin are simply being released from the hydrogels at the same time without any specific interaction. After the initial 24 hours, a more linear release profile was observed through 6 days. Release remained detectable through 21 days. An agarose control group was used simply as a means to demonstrate the effect of diffusion-mediated release. Different hydrogel systems will have different diffusion coefficients, thereby affecting the rate of antibiotic release that occurs. The use of another protein-based hydrogel (collagen) was unsuccessful due to degradation of the gel, though others have reported release of ciprofloxacin from collagen in a sponge form that is structurally different than the hydrogels used in our studies. The results clearly demonstrate that the release of ciprofloxacin from keratin hydrogels did not occur by diffusion, but depended on the rate of keratin degradation.

The release profiles correlate well with results of the broth inhibition assays as ciprofloxacin maintained significant inhibition of bacterial growth for over 3 weeks (23 days). The amount of ciprofloxacin release from the gels achieved a value above the reported minimum inhibitory concentration (MIC) for S. aureus 29213 of 0.25 μg/mL under the broth inhibition assay conditions for approximately 16 days. Therefore, the observation that keratin achieved inhibition of S. aureus over the course of 23 days may reflect some synergy with anti-bacterial properties of keratin or slight differences in the culture conditions between the experiments. In either case, it is clear that the results of the ciprofloxacin release and the bacterial inhibition are well correlated.

The overlap between ciprofloxacin and keratin release indicated the presence of interactive forces binding the ciprofloxacin to keratin that were explored further, first looking at the ciprofloxacin and keratin that had released from the gel. Through size exclusion chromatography it was deduced that, after release, the ciprofloxacin and keratin were not associated, as indicated by the distinct peaks from the size exclusion column. Therefore, it is not likely that keratin directly transports ciprofloxacin into bacteria. Although the size exclusion data indicate that keratin and ciprofloxacin do not remain associated after release, the correlation of the release profiles for keratin and ciprofloxacin indicate an interaction in the three-dimensional hydrogel state. If this were not the case, diffusion-mediated release should be observed given the porous nature of the hydrogel demonstrated in our SEM images.

Two predominant types of interactions that could contribute to this association in the three-dimensional hydrogel state are electrostatic and/or hydrophobic interactions. To explore if either of these interactions were present, the ciprofloxacin-loaded keratin was incubated with either 1M NaCl or 8M urea to disrupt electrostatic or hydrophobic interactions, respectively. The use of a 1M NaCl buffer in place of PBS led to a significant increase in the release of ciprofloxacin at 24 hours, whereas use of 8M urea led to a significant reduction in the release. These results strongly suggest that electrostatic interactions play a dominant role in retaining ciprofloxacin within the three-dimensional hydrogel. In contrast, hydrophobic interactions do not appear to play a significant role in maintaining the interaction between ciprofloxacin and keratin in the gel state. It should be noted that the application of 1M NaCl slowed the rate of keratin release while application of 8M urea increased the rate of keratin release from the hydrogels as measured by DC protein assay, indicating the role of hydrophobic interactions in maintaining the assembly of keratin proteins necessary for gel formation. Ciprofloxacin is a polar molecule and has been reported to bind with the phosphate groups of DNA. Because keratin has an isoelectric range (due to the presence of multiple proteins) of 4-6, it is reasonable to expect that ciprofloxacin would also be capable of interacting with keratin in a similar fashion. It is also possible that the presence of the sulfonic acid groups on keratin could facilitate additional interactions. The relatively weak nature of these interactions could also explain why, upon release, ciprofloxacin and keratin are no longer associated, as shown in the size exclusion chromatography data.

A useful feature of keratin hydrogels for biomedical applications is that humans are not known to express keratinase enzymes that would lead to their rapid degradation. In our in vivo mouse study, it was observed that, at the two-week time point, keratin was no longer present at the site of implantation. This is not consistent with other studies conducted in which keratose implants remain in the subcutaneous pocket for up to 4 months (data not shown). Although we are not aware of any reports of keratinase production by *Staphylococcus aureus*, numerous bacterial strains, including opportunistic pathogens such as *Pseudomonas aeruginosa*, are known to express keratinases. It is, therefore, possible that the low levels of keratinase production were present due to the high bacterial load, thereby leading to a more rapid degradation of the gels in our in vivo subcutaneous model. This suggests an interesting possibility that, with a higher bacterial load, more rapid degradation of the keratin and subsequent release of the antibiotic could occur, providing a type of on-demand release from keratin biomaterials depending on the bacterial load. The in vivo results of significant reduction in bacterial load at one week and removal of the infection at two weeks with ciprofloxacin-loaded keratin is consistent with the in vitro broth inhibition assay and demonstrates the ability of keratin hydrogels to inhibit infection in a local fashion.

Example 6

Properties of kerateines derived from human hair. Kerateines were extracted from commercially available Chinese hair using a modified protocol from Goddard and Michaelis (Goddard, D. R.; Michaelis, L. J. Biol. Chem. 1935, 112, 361-371). Proteins within the hair fibers were first solubilized through the reduction of cystine bonds by means of a 15 hr treatment with 0.5 M thioglycolic acid (TGA) titrated to pH 11.0 using sodium hydroxide. The reduction solution was retained, and additional proteins were extracted from the reduced hair fibers using a 2 hr treatment with 100 mM tris base solution, followed by another 2 hr extraction with deionized (DI) water. All extractions took place at 37° C. while vigorously shaking, and two complete extraction cycles (i.e. TGA, tris, and DI water) were completed over a 48 hr period.

Separation of α- and γ-kerateine fractions. Following the extractions, all solutions were combined and isoelectric precipitation was used to separate the higher molecular weight α-kerateine fraction from the lower molecular weight γ-kerateine fraction. Concentrated hydrochloric acid was added dropwise to the crude kerateine solution until a pH of 4.2 was achieved. At this point, the insoluble α-kerateines were separated from the soluble γ-kerateines using centrifugation (1500 rpm for 15 min). After neutralization to pH 7.4, the γ-kerateines were dialyzed against DI water using a 3 kDa nominal low molecular weight cutoff, tangential flow, spiral wound cartridge (Millipore, Billerica, Mass.) connected to a gear pump operating at a flow rate of about 1.5 L/min and a back pressure of 10 psi. Sodium hydroxide solution was used to re-dissolve the precipitated α-kerateine, after which it was loaded onto an identical dialysis system with a 30 kDa nominal low molecular weight cutoff cartridge. The protein solutions were dialyzed separately until five complete system washes were achieved while monitoring pH and electrical conductivity. Following dialysis, the kerateine solutions were shell frozen in liquid nitrogen and then lyophilized. The lyophilized protein was ground into a fine powder and stored under dry conditions at −80° C. until use.

Protein Characterization. For all characterization techniques, lyophilized kerateine powder was dissolved in ultrapure water. Electrophoretic separation of the α- and γ-kerateine fractions was done using the NuPAGE Pre-Cast Gel System (Invitrogen Corporation, Carlsbad, Calif.). Prior to loading, samples were mixed with 4×SDS loading buffer and reduced with 500 mM DTT while heating at 70° C. for 10 min. Approximately 45 µg of protein was applied to each lane of a 4-12% NuPAGE Bis-Tris gradient gel. NuPAGE 1×MES electrophoresis buffer was used and NuPAGE antioxidant was added to the upper buffer chamber to prevent re-oxidation of the reduced proteins during electrophoresis. Following separation, gels were stained with Coomassie Blue.

For mass spectrometry (MS) analysis, protein bands were extracted from the gels and washed in 50% methanol and 25 mM ammonium bicarbonate for 2 hrs followed by a brief wash in water. The isolated bands were then dehydrated in 100% acetonitrile for 15 min and dried in a vacuum centrifuge. Protein digestion was performed overnight at room temperature using 10 ng/µl trypsin (Promega Corporation, Madison, Wis.) in 25 mM ammonium bicarbonate. Peptides were extracted twice with 100 µl and 50 µl of 75% acetonitrile and 0.1% trifluoracetic acid solutions. Solutions for each sample were combined and dried in a vacuum centrifuge. Mass spectrometry analysis was performed using the ESIFTICR method (electrospray ionization coupled with Fourier transform ion cyclotron resonance) (LTQ Orbitrap XL ETD, Thermo Fisher Scientific, Waltham, Mass.). Mascot server 2.2.07 (Matrix Science, UK) was used for protein identification. The UniProtKB/Swiss-Prot database was searched for human proteins. The number of possible missed cleavage sites was set to 2, fixed modification was carboxymethyl, peptide mass tolerance was 20 ppm, and fragments mass tolerance was 0.5 Da. The amount of free cysteine present in the kerateine extracts was quantified using an Ellman's reagent (5,5'-dithiobis(2-nitrobenzoic acid); DTNB) assay (Thermo Fisher Scientific). In this colorimetric assay, free thiols present within the protein samples react with DTNB to produce 2-nitro-5-thiobenzoic acid (TNB), which was quantified by measuring the absorbance at 412 nm. A cysteine-HCl standard was used to determine the moles of cysteine per moles of kerateine for both the α- and γ-kerateine fractions.

Preparation of Kerateine Hydrogels, Sponges and Films. Kerateine materials were formed by mixing together α- and γ-kerateine dry powders at ratios of 100/0, 90/10, 80/20, 70/30, 60/40 and 50/50 (% α/γ). Hydrogels were created by dissolving the powder in ultrapure water at a total protein concentration of 20% (w/v), followed by an overnight incubation at 37° C. to allow for oxidative crosslinking of the cysteine residues. To create kerateine sponges, the hydrogels were frozen at −80° C. for 24 hrs and lyophilized. Films were formed by adding 3% (w/v) kerateine solutions to cultureware (5 mg/cm$^2$) and evaporating the excess water by exposure to ambient air for an 8-12 hr period at 37° C.

Hydrolytic Stability of Hydrogels and Sponges. To assess the effect of α:γ ratio on hydrolytic degradation, kerateine hydrogels and sponges were created as described above and then sterilized using a 1 Mrad dose of γ-irradiation. Following sterilization, the initial weight of each hydrogel and sponge was recorded and each sample placed in 10 mL of sterile PBS and stored at 37° C. The amount of protein released into solution was measured at 1 and 3 days, 1 and 2 weeks, and 1-4 months. At each time point, 1 mL of PBS was removed aseptically from each tube and a DC Protein assay used to measure the amount of protein released into solution. The percent degradation of the samples was calculated as the amount of protein released in relation to the initial mass of the samples.

Characterization of Kerateine Extracts. Electrophoretic separation of the α- and γ-kerateine fractions confirmed differences in molecular weights of the two protein subtypes. Consistent with the reported characteristics of hair keratins, the α-fraction was shown to contain proteins of approximately 50 and 57 kDa and mass spectrometry data confirmed these proteins to be specific type I and type II keratins, respectively, as listed in Table 1.

| Protein ID | Acc. No. | Protein Score | Total Peptides | % Seq. Cover | MW (kg/mol) | ID Band |
|---|---|---|---|---|---|---|
| K31 | Q15323 | 2796 | 1024 | 62.0 | 48.7 | + |
| K33b | Q14525 | 2740 | 796 | 63.9 | 47.3 | + |
| K33a | O76009 | 2448 | 808 | 63.9 | 47.2 | + |
| K34 | O76011 | 2024 | 558 | 57.6 | 50.8 | + |
| K86 | O43790 | 2805 | 890 | 53.5 | 55.1 | * |
| K81 | Q14533 | 2796 | 896 | 48.5 | 56.9 | * |
| K83 | P78385 | 2663 | 806 | 44.2 | 55.9 | * |
| K85 | P78386 | 2434 | 612 | 47.5 | 57.3 | * |
| KAP1-5 | Q9BYS1 | 357, 60 | 11, 2 | 9.8, 13.2 | 20.4 | •, † |
| KAP1-3 | Q8IUG1 | 281, 51 | 11, 1 | 9.6, 11.3 | 20.9 | •, † |
| KAP1-1 | Q07627 | 281, 51 | 11, 1 | 9.6, 11.3 | 20.8 | •, † |

Figure 9:
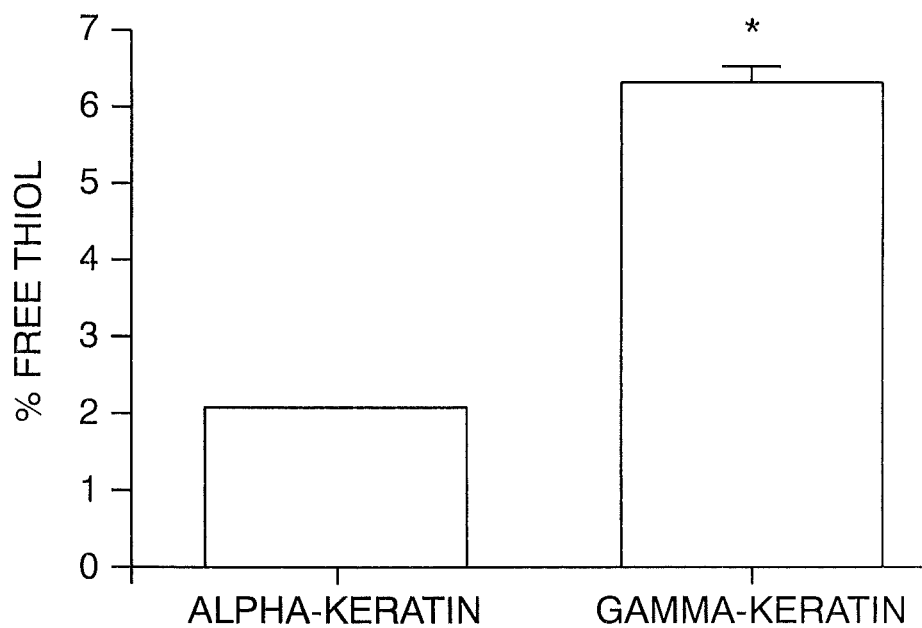
FIG. 9. Molar percent of free thiol present within the α- and γ-kerateine fractions as measured with the Ellman's reagent assay. (* $p<0.001$, n=6 replicates)

Bands present around 100 kDa in the α-fraction were shown to contain both type I and type II keratins, suggesting that the proteins within our extract solutions most likely exist in heterodimeric form, as opposed to monomeric form as would be expected from the reduced and denatured conditions of SDS-PAGE. The γ-kerateine fraction contained proteins of much lower molecular weight, around 10-28 kDa. Three proteins of the KAP1 family were identified by MS, which are the high sulfur matrix proteins found predominantly within the hair cortex. In addition, the γ-fraction contained low molecular weight fragments of the keratins identified in the α-fraction, which suggests that the chemical procedures used to extract and separate the hair proteins resulted in hydrolysis and fragmentation, the product of which is readily disassociated from the α-kerateine dimers. The reductive chemistry used to extract kerateines preserves the sulfhydryl groups within cysteine amino acids, which allows for the creation of stabile, highly crosslinked structures through reformation of intermolecular disulfide bonds. Following extraction, the sulfhydryl content of the α- and γ-kerateine fractions was measured using the Ellman's reagent. Results showed that the γ-fraction had a significantly greater amount of available thiol as compared to the α-fraction (FIG. 9).

An important point of clarification regarding the identity of protein bands by MS analysis is the distinction between what past keratin literature has referred to as the "γ-fraction" and "matrix proteins", two terms used synonymously throughout decades of trichocytic keratin literature. Subsequent research into hair matrix proteins led to the classifications of keratin associated proteins, and thus the common consensus among keratin researchers has been that the so-called γ-fraction is composed primarily of KAPs. The mass spectral data from this study, however, show that the γ-fraction, as isolated by isoelectric precipitation, contains very little KAPs. To the contrary, these data suggest that the majority of the γ-fraction is instead fragments of the α-fraction.

Figure 10A:
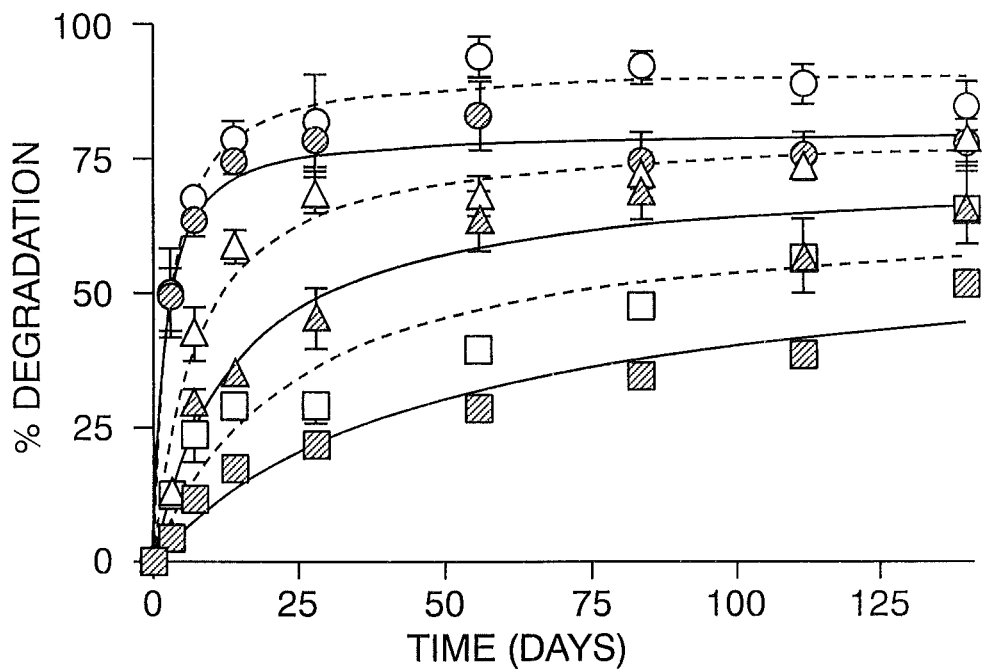
FIG. 10. Hydrolytic stability of meta-kerateine (A) hydrogels and (B) sponges over a 4 month time period. (filled square) 100/0; (open square) 90/10; (filled triangle) 80/20; (open triangle) 70/30; (filled circle) 60/40; (open circle) 50/50.
Figure 10B:
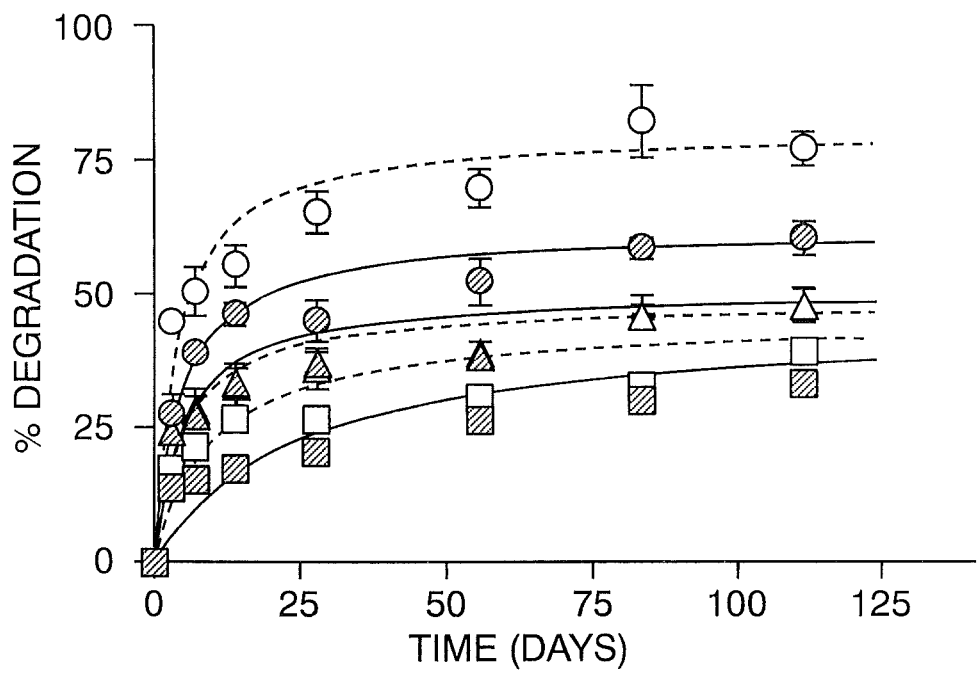
Figure 11:
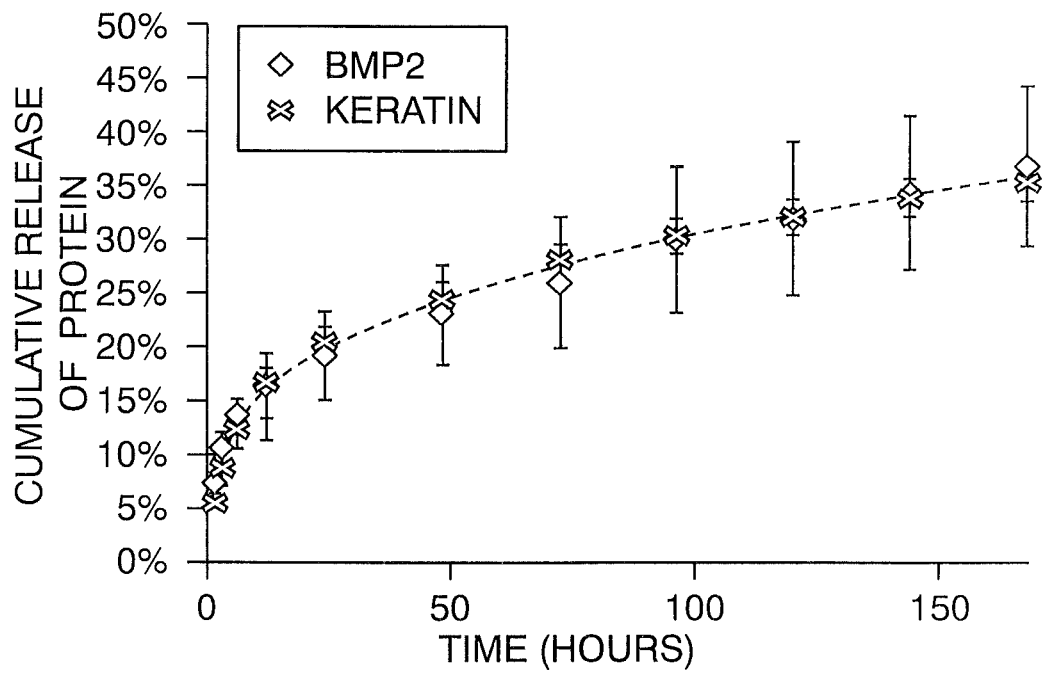
FIG. 11. Release profile of BMP-2 from a 20 weight % crude (unfractionated) keratose hydrogel (alpha+KAP+gamma), confirming the lack of burst release. Also note the near zero-order release from keratin between 24 and 168 hours.

Hydrolytic Stability of Meta-Kerateine Hydrogels. Results of the in vitro degradation study of the meta-kerateine hydrogels and sponges are shown in FIG. 10. For both hydrogels and sponges, the rate and extent of degradation was dependent on α:γ composition such that those materials with higher amounts of α-kerateines were slower to degrade and had significantly less total degradation over the 4 month time period. As reported here, degradation is the result of protein hydrolysis since no keratinases were present to enzymatically digest the samples and they were kept under sterile conditions. Therefore, the slower degradation of kerateine compositions with higher α-kerateine content is attributed to the greater amount of chemical crosslinks (i.e. disulfide bonds), which are less susceptible to hydrolysis and, thus, degradation. In addition, the total degradation of each kerateine sponge after 4 months was significantly less than the degradation of its corresponding hydrogel (p<0.01 for all groups, n=6). This finding is most likely due to the decreased water content and swelling properties of the dried sponges, which preserves the crosslinked structure and leads to more stable materials. In a similar model of hydrolytic stability, kerateine hydrogels made from unfractionated, crude extracts were shown to degrade at a rapid rate within the first 7 days followed by a plateau in total protein release after the first month and a total degradation of 66% at 6 months. These results compare well with the degradation profiles for kerateine hydrogel compositions containing an α:γ composition of 80:20, which corresponds to the approximate native ratio of keratins and matrix proteins present within the hair fiber and the approximate yields of α- and γ-kerateines from the extraction process.

Keratin-based biomaterials have increasingly become the focus of biomedical research efforts due in part to their excellent biocompatibility and propensity to self assemble into ordered network structures. Essentially all of the keratin biomaterials developed thus far, however, have been created using poorly purified, crude hair/wool extracts. In this work, it was shown that these crude extracts can be further fractionated into their structural (KIF) and matrix (KAPs) constituents and recombined to allow control of the overall physical and degradation characteristics on the protein composition of hydrogels and sponges.

Example 7

Figure 12:
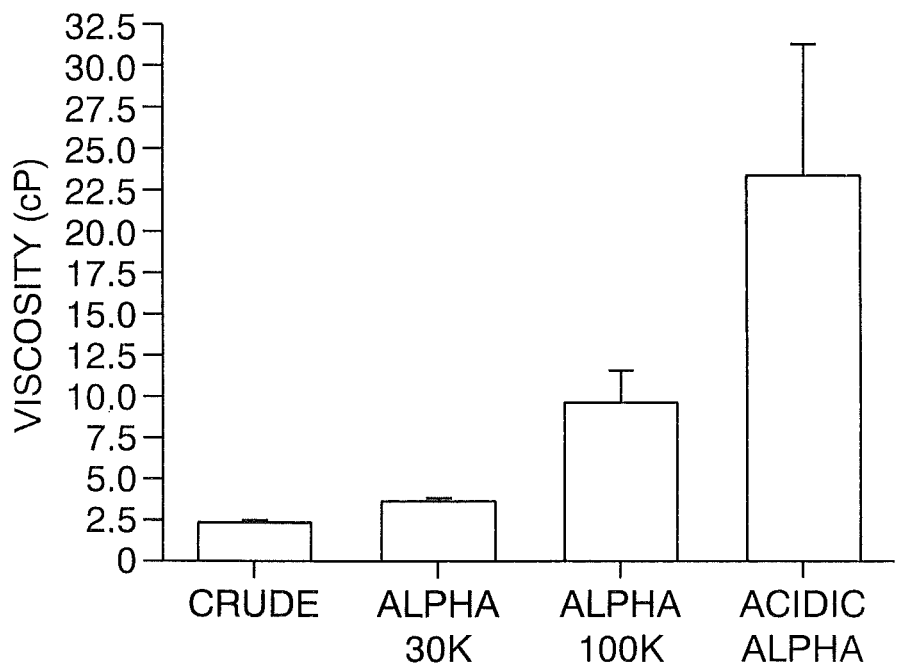
FIG. 12. Viscosity of keratose solutions of increasing acidic alpha purity.

Prolonging degradation rate by increasing viscosity. Crude keratose is a heterogeneous mixture of alpha, KAP, and gamma fractions. A crude keratose sample, prepared as described previously, was dialyzed using a 30K Da nominal low molecular weight cutoff (NLMWCO) membrane. This results in removal of the gamma fraction and retention of an alpha+KAP fraction wherein the alpha component is in the form of monomers, dimers, and higher molecular weight oligomers (this is true of both keratose and kerateine). When a 100K Da NLMWCO membrane was used, this resulted in retention of dimers and higher molecular weight oligomers. This sample was further purified by ion exchange chromatography to remove the KAP component as previously described and dialyzed again at 100 K Da, which resulted in the isolation of acidic alpha keratose. Each keratose sample was dissolved at 4 weight percent in saline and analyzed for viscosity. As can be seen from these data, as the acidic alpha content becomes higher (i.e. increased purity), the viscosity increases. This increase in viscoelastic characteristics will lead to an increase in hydrolytic stability and thus, a prolonged degradation rate. (FIG. 12)

Example 8

Injectable keratin hydrogel with growth factors. After sterilization of lyophilized keratin (kerateine, keratose, including alpha+KAP, and alpha, acidic alpha, and basic alpha sub-fractions), the appropriate concentration and amount of growth factor is dissolved in a specific volume of PBS and added to the appropriate amount of keratin. The keratin is allowed to equilibrate overnight at 37° C. and spontaneously forms a gel. The hydrogel is formed under aseptic conditions and is loaded into a sterile syringe for injection.

The specific concentration and amounts of each growth factor may vary based on the literature and previous research. For example, samples loaded with BMP-2 are obtained by dissolving 10 µg of BMP-2 in 100 µL of PBS and added to 8 mg of keratin. Release kinetics are measured with a small amount of growth factor-loaded hydrogel (e.g. 100 µL) placed at the bottom of a sterile microfuge tube and 1 mL of sterile PBS placed on top. The samples are kept at 37° C. and every 3-5 days a small aliquot is taken and replaced with fresh PBS, and the aliquot is analyzed for both growth factor and keratin using an enzyme-linked immunosorbant assay kit (ELISA; R&D Systems, Minneapolis, Minn.) and total protein assay (Bio-Rad, Hercules, Calif.), respectively. Samples are run in triplicate and reported as mean± standard error of the mean (SEM).

Binding of the growth factors to keratin are investigated using surface plasmon resonance (SPR). For this technique, keratin is deposited onto a gold-coated substrate and a solution of the growth factor of interest is flowed across. Growth factor binding to the keratin is sensed as a shift in the angle required for resonance of an incident light beam with the electrons in the gold substrate. A plot of the angle of incidence as a function of time represents the amplitude and kinetics of growth factor binding in real time. Uncoated and collagen coated substrates will serve as controls. Similarly, a buffer solution without growth factor can then be flowed over the substrate and the dissociation curve determined. From these data, the binding coefficient for each growth factor can be calculated. Samples are run in triplicate and reported as mean± SEM.

Loading efficiency for each growth factor is determined using the release kinetics method as described above. In these experiments, however, hydrogels are loaded with increasing levels of growth factor and the release determined at 37° C. at several time points. The saturation limit is defined as the concentration at which a burst release is noted. This is determined by comparing the initial slope at each concentration. The lowest concentration at which the slope is determined to be statistically different by a single-factor analysis of variance (ANOVA; $p>0.05$) from the lower concentrations will be designated the saturation limit.

Preservation of biological activity is determined by cell culture assay. BMP-2 will be tested with MC3T3-E1 cells (ATCC, Mananssas, Va.), VEGF is tested with human umbilical cord endothelial cells (HUVEC; ATCC), and IGF-I and FGF is tested with mouse MPCs. Bioactivity is determined by calcium deposition (alizarin red staining), tubule formation, and myotube formation assay, respectively.

The bioactivity of each keratin hydrogel formulation is tested by storing sterile, growth factor-loaded gel in syringes at 4° C., room temperature, and 37° C. Collagen gel and saline solutions serve as controls. At pre-determined time points, an aliquot of the gel will be expelled from the syringe and extracted with culture media. The concentration of growth factor in this extract will be verified using an ELISA kit as previously described and then it will be used to culture the target cell type. Bioactivity will be determined for each cell type using its respective assay and compared to fresh growth factor. Bioactivity will be considered to have been preserved when there is no statistically significant difference (i.e. $p>0.05$) between the extracted growth factor and fresh growth factor as determined by a Student's t-test.

The foregoing is illustrative of the present invention, and is not to be construed as limiting thereof. The invention is defined by the following claims, with equivalents of the claims to be included therein.

That which is claimed is:

1. A hydrogel composition for controlled release of a compound of interest, comprising:
   a keratin composition selected from the group consisting of: keratose, kerateine, and combinations thereof; and
   said compound of interest dispersed in said keratin composition and retained within said keratin composition through electrostatic interactions;
   wherein said hydrogel composition has a pH of from 4 to 6 and said hydrogel composition is formed from said keratin composition, and the hydrogel composition at said pH does not precipitate the keratin composition and said compound of interest does not precipitate within the hydrogel composition,
   wherein the controlled release of said compound of interest from said hydrogel composition is controlled by degradation of said keratin composition.

2. The hydrogel composition of claim 1, wherein said keratin composition is selected from the group consisting of: acidic keratose, basic keratose, acidic kerateine, basic kerateine, and combinations thereof.

3. The hydrogel composition of claim 1, wherein said keratin composition is selected from the group consisting of: α-keratose, γ-keratose, basic α-keratose, acidic α-keratose, basic γ-keratose, acidic γ-keratose, and combinations thereof.

4. The hydrogel composition of claim 1, wherein said keratin composition is selected from the group consisting of: α-kerateine, γ-kerateine, basic α-kerateine, acidic α-kerateine, basic γ-kerateine, acidic γ-kerateine, and combinations thereof.

5. The hydrogel composition of claim 1, wherein said hydrogel composition comprises from 0.5 to 50% by weight of said keratin composition selected from keratose, kerateine, and combinations thereof, and from 0.5 to 50% by weight of said compound of interest.

6. The hydrogel composition of claim 1, wherein said compound of interest comprises a protein or peptide.

7. The hydrogel composition of claim 1, wherein said compound of interest comprises an antibody or a fragment thereof.

8. The hydrogel composition of claim 1, wherein said compound of interest comprises a growth factor.

9. The hydrogel composition of claim 1, wherein said compound of interest comprises an antibiotic.

10. The hydrogel composition of claim 1, wherein said compound of interest is ciprofloxacin or a derivative thereof.

11. The hydrogel composition of claim 1 formulated for topical administration.

12. The hydrogel composition of claim 1 formulated for parenteral administration.

13. The hydrogel composition of claim 1 formulated for release of said compound of interest over a time of from 1 to 48 hours.

14. The hydrogel composition of claim 1 formulated for release of said compound of interest over a time of from 1 to 180 days.

15. The hydrogel composition of claim 1, wherein said keratin composition is a mixture of alpha and gamma kerateine.

16. The hydrogel composition of claim 15, wherein said mixture of alpha kerateine and gamma kerateine is selected from the group consisting of: about 50% alpha-kerateine and about 50% gamma-kerateine, about 60% alpha-kerateine and about 40% gamma-kerateine, about 70% alpha-kerateine and about 30% gamma-kerateine, about 80% alpha-kerateine and about 20% gamma-kerateine, and about 90% alpha-kerateine and about 10% gamma-kerateine.

17. The hydrogel composition of claim 1, wherein said compound of interest comprises a fluorinated quinoline antibiotic.

18. A method of administering a compound of interest to a subject in need thereof, said method comprising the steps of:
providing the hydrogel composition of claim 1; and
administering said hydrogel composition to said subject in a treatment effective amount.

19. The method of claim 18, wherein said subject is a human subject.

20. A hydrogel composition comprising a reconstituted mixture of alpha kerateine and gamma kerateine and at least one compound of interest;
wherein said alpha kerateine comprises 45% to about 99% of the mixture;
wherein said hydrogel composition is formed from said mixture of alpha kerateine and gamma kerateine;
wherein said at least one compound of interest is retained within said mixture of alpha kerateine and gamma kerateine through electrostatic interactions;
wherein said hydrogel composition is formulated for controlled release of said at least one compound of interest over 1 to 180 days; and
wherein the controlled release of said at least one compound of interest from said hydrogel composition is controlled by degradation of the hydrogel composition formed from said mixture of alpha kerateine and gamma kerateine.

21. The hydrogel composition of claim 20, wherein said mixture of alpha kerateine and gamma kerateine is selected from the group consisting of: about 50% alpha-kerateine and about 50% gamma-kerateine, about 60% alpha-kerateine and about 40% gamma-kerateine, about 70% alpha-kerateine and about 30% gamma-kerateine, about 80% alpha-kerateine and about 20% gamma-kerateine, and about 90% alpha-kerateine and about 10% gamma-kerateine.

22. The hydrogel composition of claim 20, wherein said hydrogel composition is formulated as a sponge.

23. The hydrogel composition of claim 20, wherein said hydrogel composition is formulated as a film.

24. A hydrogel composition for controlled release of a compound of interest, comprising:
a keratin composition comprising keratose; and
said compound of interest dispersed in said keratin composition and retained within said keratin composition through electrostatic interactions;
wherein said hydrogel composition has a pH of from 4 to 6 and said hydrogel composition is formed from said keratose, and the hydrogel composition at said pH does not precipitate the keratin composition and said compound of interest does not precipitate within the hydrogel composition,
wherein the controlled release of said compound of interest from said hydrogel composition is controlled by degradation of the keratose.

25. The hydrogel composition of claim 24, wherein said keratose is alpha keratose.

* * * * *